(12) United States Patent
Marasco et al.

(10) Patent No.: US 9,951,122 B2
(45) Date of Patent: Apr. 24, 2018

(54) ANTIBODIES AGAINST INFLUENZA VIRUS AND METHODS OF USE THEREOF

(71) Applicants: Dana-Farber Cancer Institute, Inc., Boston, MA (US); Burnham Institute for Medical Research, La Jolla, CA (US)

(72) Inventors: Wayne A. Marasco, Wellesley, MA (US); Jianhua Sui, Waltham, MA (US); Robert C. Liddington, La Jolla, CA (US)

(73) Assignees: DANA-FARBER CANCER INSTITUTE, INC., Boston, MA (US); BURNHAM INSTITUTE FOR MEDICAL RESEARCH, La Jolla, CA (US)

( * ) Notice: Subject to any disclaimer, the term of this patent is extended or adjusted under 35 U.S.C. 154(b) by 60 days.

(21) Appl. No.: 13/965,092

(22) Filed: Aug. 12, 2013

(65) Prior Publication Data
US 2014/0011982 A1 Jan. 9, 2014

Related U.S. Application Data

(63) Continuation of application No. 12/746,622, filed as application No. PCT/US2008/085876 on Dec. 8, 2008, now abandoned.

(60) Provisional application No. 61/005,725, filed on Dec. 6, 2007, provisional application No. 61/091,599, filed on Aug. 25, 2008.

(51) Int. Cl.
*C07K 16/10* (2006.01)
*C07K 14/005* (2006.01)
*A61K 39/00* (2006.01)

(52) U.S. Cl.
CPC ........ *C07K 16/1018* (2013.01); *C07K 14/005* (2013.01); *A61K 2039/505* (2013.01); *C07K 2317/21* (2013.01); *C07K 2317/52* (2013.01); *C07K 2317/565* (2013.01); *C07K 2317/622* (2013.01); *C07K 2317/76* (2013.01); *C07K 2317/92* (2013.01); *C07K 2319/00* (2013.01); *C07K 2319/40* (2013.01); *C12N 2760/16122* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,522,811 A | 6/1985 | Eppstein et al. |
| 4,544,545 A | 10/1985 | Ryan et al. |
| 4,676,980 A | 6/1987 | Segal et al. |
| 4,816,567 A | 3/1989 | Cabilly et al. |
| 4,946,778 A | 8/1990 | Ladner et al. |
| 5,013,556 A | 5/1991 | Woodle et al. |
| 5,030,719 A | 7/1991 | Umemoto et al. |
| 5,091,513 A | 2/1992 | Huston et al. |
| 5,132,405 A | 7/1992 | Huston et al. |
| 5,233,409 A | 8/1993 | Schwab |
| 5,545,806 A | 8/1996 | Lonberg et al. |
| 5,545,807 A | 8/1996 | Surani et al. |
| 5,569,825 A | 10/1996 | Lonberg et al. |
| 5,589,174 A | 12/1996 | Okuno et al. |
| 5,625,126 A | 4/1997 | Lonberg et al. |
| 5,631,350 A | 5/1997 | Okuno et al. |
| 5,633,425 A | 5/1997 | Lonberg et al. |
| 5,661,016 A | 8/1997 | Lonberg et al. |
| 5,916,771 A | 6/1999 | Hori et al. |
| 5,939,598 A | 8/1999 | Kucherlapati et al. |
| 2009/0092620 A1 | 4/2009 | Moste et al. |
| 2009/0311265 A1 | 12/2009 | Van Den Brink et al. |

FOREIGN PATENT DOCUMENTS

| | | |
|---|---|---|
| JP | H06100594 A | 4/1994 |
| JP | 2005-170945 | 6/2005 |
| JP | 2005-523946 | 8/2005 |
| JP | 2007000141 A | 1/2007 |
| WO | WO-9100360 A1 | 1/1991 |
| WO | WO-9220373 A1 | 11/1992 |
| WO | WO-93012232 A1 | 6/1993 |
| WO | WO-9402602 A1 | 2/1994 |
| WO | WO-94002610 A1 | 2/1994 |
| WO | WO-9409136 A1 | 4/1994 |
| WO | WO-9411026 A2 | 5/1994 |
| WO | WO-95022618 A1 | 8/1995 |
| WO | WO-9633735 A1 | 10/1996 |
| WO | WO-9634096 A1 | 10/1996 |
| WO | WO-97014809 A2 | 4/1997 |

(Continued)

OTHER PUBLICATIONS

Baras et al. "Cross-Protection Against Lethal H5N1 Challenge in Ferrets with an Adjuvanted Pandemic Influenza Vaccine." *PLoS One*. 3.1(2008):e1401:1-4.

Barbas et al. "Recombinant Human Fab Fragments Neutralize Human Type 1 Immunodeficiency Virus in vitro." *PNAS*. 89.19(1992):9339-9343.

Bobo et al. "Convection-Enhanced Delivery of Macromolecules in the Brain." *PNAS*. 91(1994):2076-2080.

(Continued)

*Primary Examiner* — Benjamin P Blumel
(74) *Attorney, Agent, or Firm* — Baker Donelson

(57) ABSTRACT

The invention provides human scFv antibodies and monoclonal antibodies that neutralize influenza virus. Also provided are methods of treating and/or preventing a influenza related disease or disorder such bird flu The invention also provides methods of vaccinating a patient against influenza. Also provided are methods of diagnosing influenza-related diseases or disorders and methods of detecting the presence of a influenza in a sample.

9 Claims, 19 Drawing Sheets

(56) References Cited

FOREIGN PATENT DOCUMENTS

| WO | WO-99014353 A2 | 3/1999 |
|---|---|---|
| WO | WO-99045959 A1 | 9/1999 |
| WO | WO-9953049 A1 | 10/1999 |
| WO | WO-00055335 A1 | 9/2000 |
| WO | WO-00055378 A1 | 9/2000 |
| WO | WO-02000914 A2 | 1/2002 |
| WO | WO-0246235 A1 | 6/2002 |
| WO | WO-03048337 A2 | 6/2003 |
| WO | WO 2004/004633 | 1/2004 |
| WO | WO-04004633 A2 | 1/2004 |
| WO | WO-05005615 A2 | 1/2005 |
| WO | WO-05060520 A2 | 7/2005 |
| WO | WO-05123774 A2 | 12/2005 |
| WO | WO-06022944 A2 | 3/2006 |
| WO | WO-06082406 A2 | 8/2006 |
| WO | WO-06089141 A2 | 8/2006 |
| WO | WO-06107617 A2 | 10/2006 |
| WO | WO-07044695 A2 | 4/2007 |
| WO | WO-07065027 A2 | 6/2007 |
| WO | WO-07089753 A2 | 8/2007 |
| WO | WO-07134327 A2 | 11/2007 |
| WO | WO-07146432 A2 | 12/2007 |
| WO | WO-08028946 A2 | 3/2008 |
| WO | WO-09059032 A2 | 5/2009 |
| WO | WO-09079259 A2 | 6/2009 |
| WO | WO-09086514 A1 | 7/2009 |
| WO | WO-09115972 A1 | 9/2009 |
| WO | WO-10010466 A2 | 1/2010 |
| WO | WO-10010467 A2 | 1/2010 |
| WO | WO-10027818 A2 | 3/2010 |
| WO | WO-10130636 A1 | 11/2010 |

OTHER PUBLICATIONS

Bona et al. "Towards Development of T-Cell Vaccines." *Immunol. Today.* 19.3(1998):126-133.

Bresson et al. "Safety and Immunogenicity of an Inactivated Split-Virion Influenza A/Vietnam/1194/2004 (H5N1) Vaccine: Phase 1 Randomised Trial." *Lancet.* 367(2006):1657-1664.

Brodeur et al. "Mouse-Human Myeloma Partners for the Production of Heterohybridomas." *Monoclonal Antibody Production Techniques and Applications.* New York: Marcel Dekker, Inc. Schook, ed. (1987):51-63.

Bullough et al. "Structure of Influenza Haemagglutinin at the pH of Membrane Fusion." *Nature.* 371(1994):37-43.

Burton. "Antibodies, Viruses and Vaccines." *Nat. Rev. Immunol.* 2(2002):706-713.

Carell et al. "A Novel Procedure for the Synthesis of Libraries Containing Small Organic Molecules." *Angew. Chem. Int. Ed. Engl.* 33(1994):2059-2061.

Carell et al. "A Solution-Phase Screening Procedure for the Isolation of Active Compounds from a Library of Molecules." *Angew. Chem. Int. Ed. Engl.* 33.20(1994):2061-2064.

Caron et al. "Engineered Humanized Dimeric Forms of IgG are More Effective Antibodies." *J. Exp. Med.* 176(1992):1191-1195.

Carrat et al. "Influenza Vaccine: The Challenge of Antigenic Drift." *Vaccine.* 25(2007):6852-6862.

Casadevall. "Antibodies for Defense Against Biological Attack." *Nat. Biotechnol.* 20(2002):114.

Casares et al. "Protective Immunity Elicited by Vaccination with DNA Encoding for a B Cell and a T Cell Epitope of the A/PR/8/34 Influenza Virus." *Viral Immunol.* 10.3(1997):129-136.

Cho et al. "An Unnatural Biopolymer." *Science.* 261(1993):1303-1305.

Cinatl et al. "The Threat of Avian Influenza A (H5N1). Part IV: Development of Vaccines." *Med. Microbiol. Immunol.* 196(2007):213-225.

Cole et al. "The EBV-Hybridoma Technique and its Application to Human Lung Cancer." *Monoclonal Antibodies and Cancer Therapy.* (1985):77-96.

Cote et al. "Generation of Human Monoclonal Antibodies Reactive with Cellular Antigens." *PNAS.* 80(1983):2026-2030.

Cull et al. "Screening for Receptor Ligands Using Large Libraries of Peptides Linked to the C Terminus of the *lac* Repressor." *PNAS.* 89(1992):1865-1869.

Cwirla et al. "Peptides on Phage: A Vast Library of Peptides for Identifying Ligands." *PNAS.* 87(1990):6378-6382.

Daniels et al. "Fusion Mutants of the Influenza Virus Hemagglutinin Glycoprotein." *Cell.* 40(1985):431-439.

Davidson et al. "A Model System for in vivo Gene Transfer into the Central Nervous System Using an Adenoviral Vector." *Nat. Genet.* 3.3(1993):219-223.

Davies et al. "Antibody-Antigen Complexes." *Annu. Rev. Biochem.* 59(1990):439-473.

De Jong et al. "A Pandemic Warning?" *Nature.* 389. 6651(1997):554.

De Wit et al. "Emerging Influenza." *J. Clin. Virol.* 41(2008):1-6.

Devlin et al. "Random Peptide Libraries: A Source of Specific Protein Binding Molecules." *Science.* 249(1990):404-406.

DeWitt et al. "'Diversomers': An Approach to Nonpeptide, Nonoligomeric Chemical Diversity." *PNAS.* 90(1993):6909-6913.

Earp et al. "The Many Mechanisms of Viral Membrane Fusion Proteins." *Curr. Top. Microbiol. Immunol.* 285(2004):25-66.

Eppstein et al. "Biological Activity of Liposome-Encapsulated Murine Interferon γ is Mediated by a Cell Membrane Receptor." *PNAS.* 82(1985):3688-3692.

Erb et al. "Recursive Deconvolution of Combinatorial Chemical Libraries." *PNAS.* 91(1994):11422-14426.

Fauci. "Pandemic Influenza Threat and Preparedness." *Emerg. Infect. Dis.* 12(2006):73-77.

Felici et al. "Selection of Antibody Ligands from a Large Library of Oligopeptides Expressed on a Multivalent Exposition Vector." *J. Mol. Biol.* 222(1991):301-310.

Fishwild et al. "High-Avidity Human IgGκ Monoclonal Antibodies from a Novel Strain of Minilocus Transgenic Mice." *Nat. Biotechnol.* 14.7(1996):845-851.

Fodor et al. "Multiplexed Biochemical Assays with Biological Chips." *Nature.* 364(1993):555-556.

Fouchier et al. "Characterization of a Novel Influenza A Virus Hemagglutinin Subtype (H16) Obtained from Black-Headed Gulls." *J. Virol.* 79(2005):2814-2822.

Gallop et al. "Applications of Combinatorial Technologies to Drug Discovery." *J. Med. Chem.* 37.9(1994):1233-1251.

Garrity et al. "Refocusing Neutralizing Antibody Response by Targeted Dampening of an Immunodominant Epitope." *J. Immunol.* 159(1997):279-289.

Geller et al. "An HSV-1 Vector Expressing Tyrosine Hydroxylase Causes Production and Release of L-DOPA from Cultured Rat Striatal Cells." *J. Neurochem.* 64.2(1995):487-496.

Geller et al. "Infection of Cultured Central Nervous System Neurons with a Defective Simplex Virus 1 Vector Results in Stable Expression of *Escherichia coli* β-Galactosidase." *PNAS.* 87.3(1990):1149-1153.

Geller et al. "Long-Term Increases in Neurotransmitter Release from Neuronal Cells Expressing a Constitutively Active Adenylate Cyclase from a Herpes Simplex Virus Type 1 Vector." *PNAS.* 90.16(1993):7603-7607.

Gerloni et al. "Immunity to *Plasmodium falciparum* Malaria Sporozoites by Somatic Transgene Immunization." *Nat. Biotechnol.* 15.9(1997):876-881.

Gerloni et al. "Somatic Transgene Immunization with DNA Encoding an Immunoglobulin Heavy Chain." *DNA Cell Biol.* 16.5(1997):611-625.

Glaser et al. "A Single Amino Acid Substitution in 1918 Influenza Virus Hemagglutinin Changes Receptor Binding Specificity." *J. Virol.* 79(2005):11533-11536.
Goding. "Production of Monoclonal Antibodies." *Monoclonal Antibodies: Principles and Practice.* London: Academic Press. (1986):59-103.
Godley et al. "Introduction of Intersubunit Disulfide Bonds in the Membrane-Distal Region of the Influenza Hemagglutinin Abolishes Membrane Fusion Activity." *Cell.* 68(1992):635-645.

(56) References Cited

OTHER PUBLICATIONS

Ha et al. "H5 Avian and H9 Swine Influenza Virus Haemagglutinin Structures: Possible Origin of Influenza Subtypes." *Embo. J.* 21(2002):865-875.
Ha et al. "X-Ray Structure of the Hemagglutinin of a Potential H3 Avian Progenitor of the 1968 Hong Kong Pandemic Influenza Virus." *Virology.* 309(2003):209-218.
Ha et al. "X-Ray Structures of H5 Avian and H9 Swine Influenza Virus Hemagglutinins Bound to Avian and Human Receptor Analogs." *PNAS.* 98.20(2001):11181-11186.
Hoogenboom et al. "By-Passing Immunisation: Human Antibodies from Synthetic Repertoires of Germline VH Gene Segments Rearranged in vitro." *J. Mol. Biol.* 227.2(1992):381-388.
Houghten et al. "The Use of Synthetic Peptide Combinatorial Libraries for the Identification of Bioactive Peptides." *BioTechniques.* 13.3(1992):412-421.
Huang et al. "Influenza A Virus Neuraminidase Limits Viral Superinfection." *J. Virol.* 82(2008):4834-4843.
Huang et al. "Structural Basis of Tyrosine Sulfation and VH-Gene Usage in Antibodies that Recognize the HIV Type 1 Coreceptor-Binding Site on gp120." *PNAS.* 101(2004):2706-2711.
Huse et al. "Generation of a Large Combinatorial Library of the Immunoglobulin Repertoire in Phage Lambda." *Science.* 146(1989):1275-1281.
Huston et al. "Protein Engineering of Antibody Binding Sites: Recovery of Specific Activity in an Anti-Digoxin Single-Chain Fv Analogue Produced in *Escherichia coli.*" *PNAS.* 85(1988):5879-5883.
Hwang et al. "Hepatic Uptake and Degradation of Unilamellar Sphingomylin/Cholesterol Liposomes: A Kinetic Study." *PNAS.* 77.7(1980):4030-4034.
Igarashi et al. "Human Immunodeficiency Virus Type 1 Neutralizing Antibodies Accelerate Clearance of Cell-Free Virions from Blood Plasma." *Nat. Med.* 5(1999):211-216.
Jansen et al. "Immunotoxins: Hybrid Molecules Combining High Specificity and Potent Cytotoxicity." *Immunological Rev.* 62(1982):185-216.
Kaplitt et al. "Long-Term Gene Expression and Phenotypic Correction Using Adeno-Associated Virus Vectors in the Mammalian Brain." *Nat. Genet.* 8.2(1994):148-154.
Kashyap et al. "Combinatorial Antibody Libraries From Survivors of the Turkish H5N1 Avian Influenza Outbreak Reveal Virus Neutralization Strategies." *PNAS.* 105(2008):5986-5991.
Keller et al. "Passive Immunity in Prevention and Treatment of Infectious Diseases." *Clin. Microbiol. Rev.* 13.4(2000):602-614.
Kida et al. "Interference with a Conformational Change in the Haemagglutinin Molecule of Influenza Virus by Antibodies as a Possible Neutralization Mechanism." *Vaccine.* 3(1985):219-222.
Killen et al. "Specific Killing of Lymphocytes that Cause Experimental Autoimmune Myasthenia Gravis by Ricin Toxin-Acetylcholine Receptor Conjugates." *J. Immunol.* 133.5(1984):2549-2553.
Kozbor et al. "A Human Hybrid Myeloma for Production of Human Monoclonal Antibodies." *J. Immunol.* 133.6(1984):3001-3005.
Kozbor et al. "The Production of Monoclonal Antibodies from Human Lymphocytes." *Immunol. Today.* 4.3(1983):72-79.
Krause et al. "An Insertion Mutation that Distorts Antibody Binding Site Architecture Enhances Function of a Human Antibody." *mBio.* 2.1(2011):1-8.
Köhler et al. "Continuous Cultures of Fused Cells Secreting Antibody of Predefined Specificity." *Nature.* 256(1975):495-497.
Lam et al. "A New Type of Synthetic Peptide Library for Identifying Ligand-Binding Activity." *Nature.* 354.6348(1991):82-84.
Lam. "Application of Combinatorial Library Methods in Cancer Research and Drug Discovery." *Anti-Cancer Drug Design.* 12(1997):145-167.
Lanza et al. "Active Immunity Against the CD4 Receptor by Using an Antibody Antigenized with Residues 41-55 of the First Extracellular Domain." *Proc. Natl. Acad. Sci. USA.* 90.24(1993):11683-11687.
Le Ga La Salle et al. "An Adenovirus Vector for Gene Transfer into Neurons and Glia in the Brain." *Science.* 259.5097(1993):988-990.
Leroux-Roels et al. "Broad Clade 2 Cross-Reactive Immunity Induced by an Adjuvanted Clade 1 rH5N1 Pandemic Influenza Vaccine." *PLoS ONE.* 3(2008):e1665.
Lin et al. "Safety and Immunogenicity of an Inactivated Adjuvanted Whole-Virion Influenza A (H5N1) Vaccine: A Phase 1 Randomised Controlled Trial." *Lancet.* 368.9540(2006):991-997.
Lonberg et al. "Antigen-Specific Human Antibodies from Mice Comprising Four Distinct Genetic Modifications." *Nature.* 368.6474(1994):856-859.
Lonberg et al. "Human Antibodies from Transgenic Mice." *Int. Rev. Immunol.* 13.1(1995):65-93.
Lunde et al. "Troybodies and Pepbodies." *Biochem. Soc. Trans.* 30.4(2002):500-506.
Malmqvist. "Biospecific Interaction Analysis Using Biosensor Technology." *Nature.* 361(1993):186-187.
Marasco et al. "Design, Intracellular Expression, and Activity of a Human Anti-Human Immunodeficiency Virus Type 1 gp120 Single-Chain Antibody." *PNAS.* 90.16(1993):7889-7893.
Marasco et al. "The Growth and Potential of Human Antiviral Monoclonal Antibody Therapeutics." *Nat. Biotechnol.* 25(2007):1421-1434.
Marks et al. "By-Passing Immunization: Building High Affinity Human Antibodies by Chain Shuffling." *Biotechnol.* 10.7(1992):779-783.
Marks et al. "By-Passing Immunization: Human Antibodies from V-Gene Libraries Displayed on Phage." *J. Mol. Biol.* 222(1991):581-597.
Martin et al. "Irreversible Coupling of Immunoglobulin Fragments to Preformed Vesicles." *J. Biol. Chem.* 257.1(1982):286-288.
Matthews et al. "Immunogenically Fit Subunit Vaccine Components Via Epitope Discovery from Natural Peptide Ligands." *J. Immunol.* 169.2(2002):837-846.
Morrison et al. "High-Flow Microinfusion: Tissue Penetration and Pharmacodynamics." *Am. J. Physiol.* 266(1994):R292-R305.
Morrison. "Success in Specification." *Nature.* 368(1994):812-813.
Mount et al. "Microcomputer Programs for Back Translation of Protein to DNA Sequences and Analysis of Ambiguous DNA Sequences." *Nucleic Acids Res.* 12.1(1984):819-823.
Munson et al. "Ligand: A Versatile Computerized Approach for Characterization of Ligand-Binding Systems." *Anal. Biochem.* 107(1980):220-239.
Naldini et al. "Efficient Transfer, Integration, and Sustained Long-Term Expression of the Transgene in Adult Rat Brains Injected with a Lentiviral Vector." *PNAS.* 93(1996):11382-11388.
Neuberger. "Generating High-Avidity Human Mabs in Mice." *Nat. Biotechnol.* 14.7(1996):826.
Nicholson et al. "Safety and Antigenicity of Non-Adjuvanted and MF59-Adjuvanted Influenza A/Duck/Singapore/97 (H5N3) Vaccine: A Randomised Trial of Two Potential Vaccines Against H5N1 Influenza." *Lancet.* 357(2001):1937-1943.
Okuno et al. "A Common Neutralizing Epitope Conserved Between the Hemagglutinins of Influenza A Virus H1 and H2 Strains." *J. Virol.* 61.5(1993): 2552-2558.
Parren et al. "The Antiviral Activity of Antibodies in Vitro and in Vivo." *Adv. Immunol.* 77(2001):195-262.
Ramakrishnan et al. "Comparison of the Selective Cytotoxic Effects of Immunotoxins Containing Ricin A Chain or Pokeweed Antiviral Protein and Anti-Thy 1.1 Monoclonal Antibodies." *Cancer Res.* 44(1984):201-208.
Rowe et al. "Detection of Antibody to Avian Influenza A (H5N1) Virus in Human Serum by Using a Combination of Serologic Assays." *J. Clin. Microbiol.* 37(1999):937-943.
Russell et al. "H1 and H7 Influenza Haemagglutinin Structures Extend a Structural Classification of Haemagglutintin Subtypes." *Virology.* 325(2004):287-296.
Scott et al. "Searching for Peptide Ligands with an Epitope Library." *Science.* 249(1990):386-390.
Shibata et al. "Neutralizing Antibody Directed Against the HIV-1 Envelope Glycoprotein Can Completely Block HIV-1/SIV Chimeric Virus Infections of Macaque Monkeys." *Nat. Med.* 5(1999):204-210.

(56) References Cited

OTHER PUBLICATIONS

Shopes et al. "A Genetically Engineered Human IgG Mutant with Enhanced Cytolytic Activity." *J. Immunol.* 148.9(1992):2918-2922.
Skehel et al. "Receptor Binding and Membrane Fusion in Virus Entry: The Influenza Hemagglutinin." *Annu. Rev. Biochem.* 69(2000):531-569.
Smirnov et al. "Prevention and Treatment of Bronchopneumonia in Mice caused by Mouse-Adapted Variant of Avian H5N2 Influzena A Virus Using Monoclonal Antibody Against Conserved Epitope in the HA Stem Region." *Arch. Virol.* 145.8(2000):1733-1741.
Stephenson et al. "Boosting Immunity to Influenza H5N1 with MF59-Adjuvanted H5N3 A/Duck/Singapore/97 Vaccine in a Primed Human Population." *Vaccine.* 21(2003):1687-1693.
Stephenson et al. "Cross-Reactivity to Highly Pathogenic Avian Influenza H5N1 Viruses After Vaccinating with Nonadjuvanted and MF59-Adjuvanted Influenza/A/Duck/Singapore/97 (h5N3) Vaccine: A Potential Priming Strategy." *J. Infect. Dis.* 191.8(2005):1210-1215.
Stevens et al. "Structure and Receptor Specificity of the Hemagglutinin from an H5N1 Influenza Virus." *Science.* 312(2006):404-410.
Stevens et al. "Structure of the Uncleaved Human H1 Hemagglutinin from the Extinct 1918 Influenza Virus." *Science.* 303(2004):1866-1870.
Stevenson et al. "A Chimeric Antibody with Dual Fc Regions (bisFabFc) Prepared by Manipulations at the IgG Hinge." *Anti-Cancer Drug Design.* 3(1989):219-230.
Steward et al. "A Mimotope from a Solid-Phase Peptide Library Induces a Measles Virus-Neutralizing and Protective Antibody Response." *J. Virol.* 69.12(1995):7668-7673.
Su et al. "Evaluation of Glu11 and Gly8 of the H5N1 Influenza Hemagglutinin Fusion Peptide in Membrane Fusion Using Pseudotype Virus and Reverse Genetics." *Acta Virol.* 153(2008):247-257.
Subbarao et al. "H5N1 Viruses and Vaccines." *PLoS Pathog.* 3(2007):e40.
Subbaro et al. "Characterization of an Avian Influence A (H5N1) Virus Isolated from a Child with a Fatal Respiratory Illness." *Science.* 279.5349(1998):393-396.
Sui et al. "Potent Neutralization of Severe Acute Respiratory Syndrome (SARS) Coronavirus by a Human mAb to S1 Protein that Blocks Receptor Association." *PNAS.* 101.8(2004):2536-2541.
Sui et al. "Structural and Functional Bases for Broad-Spectrum Neutralization of Avian and Human Influenza A Viruses." *Nat. Struct. Mol. Biol.* 16.3(2009):265-273.
Suzuki et al. "Origin and Evolution of Influenza Virus Hemagglutinin Genes." *Mol. Biol. Evol.* 19.4(2002):501-509.
Thoennes et al. "Analysis of Residues Near the Fusion Peptide in the Influenza Hemagglutinin Structure for Roles in Triggering Membrane Fusion." *Virology.* 370(2008):403-414.
Treanor et al. "Safety and Immunogenicity of a Recombinant Hemagglutinin Vaccine for H5 Influenza in Humans." *Vaccine.* 19(2001):1732-1737.
Treanor et al. "Safety and Immunogenicity of an Inacticated Subviron Influenza A (H5N1) Vaccine." *N. Eng. J. Med.* 354(2006):1343-1351.
Vajdos et al. "Comprehensive Functional Maps of the Antigen Binding Site of an Anti-ErbB2 Antibody Obtained with Shotgun Scanning Mutagenesis." *J. Mol. Biol.* 320(2002):415-428.
Vanlandschoot et al. "An Antibody Which Binds to the Membrane-Proximal End of Influenza Virus Haemagglutinin (H3 Subtype) Inhibits the Low-pH-Induced Conformational Change and Cell-Cell Fusion but Does not Neutralize Virus." *J. Gen. Virol.* 79(1998):1781-1791.
Vitetta et al. "Redesigning Nature's Poisons to Create Anti-Tumor Reagents." *Science.* 238(1987):1098-1104.
W.H.O. "Antigenic and Genetic Characteristics of H5N1 Viruses and Candidate H5N1 Vaccine Viruses Developed for Potential Use as Pre-Pandemic Vaccines." (Mar. 2007). who.int/csr/disease/avian_influenza/guidelines/summaryH520070403.pdf.
W.H.O. "Avian Influenza." (2008).
W.H.O. "Evolution of H5N1 Avian Influenza Viruses in Asia." *Emerg. Infect. Dis.* 11(2005):1515-1521.
W.H.O. "Global Influenza Virological Surveillance." (2008). http://who.int/csr/disease/influenza/influenzanetwork/en/index.html.
W.H.O. factsheet 211: Influenza (2003). who.int/mediacentre/factsheet/2003/fs211/en.
Webster et al. "1918 Spanish Influenza: The Secrets Remain Elusive." *PNAS.* 96(1999):1164-1166.
Wilkinson. "Ultimate Abs." *Scientist.* 14.8(2000):25-28.
Wilson et al. "Structure of the Haemagglutinin Membrane Glycoprotein of Influenza Virus at 3A Resolution." *Nature.* 289(1981):366-373.
Wright et al. "Orthoymyxoviruses." *Fields Virology.* Knipe et al., eds. Philadelphia: Lipincott Williams & Wilkins. Chapter 48. (2007):1691-1740.
Yamada et al. "Haemagglutinin Mutations Responsible for the Binding of H5N1 Influenza A Viruses to Human-Type Receptors." *Nature.* 444(2006):378-382.
Yang et al. "Cellular and Humoral Immune Responses to Viral Antigens Create Barriers to Lung-Directed Gene Therapy with Recombinant Adenoviruses." *J. Virol.* 69.4(1995):2004-2015.
You et al. "Targeting Dendritic Cells to Enhance DNA Vaccine Potency." *Cancer Res.* 61.9(2001):3704-3711.
Zaghouani et al. "Induction of Antibodies to the Human Immunodeficiency Virus Type 1 by Immunization of Baboons with Immunoglobulin Molecules Carrying the Principal Neutralizing Determinant of the Envelope Protein." *PNAS.* 92(1995):631-635.
Zanetti. "Antigenized Antibodies." *Nature.* 355(1992):476-477.
Zebedee et al. "Human Combinatorial Antibody Libraries to Hepatitis B Surface Antigen." *PNAS.* 89.8(1992):3175-3179.
Zuckerman et al. "Discovery of Nanomolar Ligands for 7-Transmembrane G-Protein-Coupled Receptors from a Diverse N-(Substituted)glycine Peptoid Library." *J. Med. Chem.* 37(1994):2678-2685.

Structure overview of the A/Vietnam 1203/04 trimer, receptor binding site and antigenic variation sites are highlighted on the monomer (cited from Stevens, 2006).

Fig. 1A

Location of amino acid residues in the HA of H5N1 influenza viruses that are under positive selection (cited from Smith, 2006).

| VIRUS | HUMAN mAb F10 | MURINE mAb 21G8.6 | CTRL. 80R |
|---|---|---|---|
| H5-TH04 (H5N1) | 40 | 40 | < |
| H5-HK97 (H5N1) | 160 | 40 | < |
| H1-OH83 (H1N1) | 40 | < | < |
| H1-PR34 (H1N1) | 320 | < | < |
| H2-AA60 (H2N2) | 20 | < | < |

Binding inhibition of H5-pseudotyped viruses to cells by anti-H5 nAbs

- 1 μg/mL or 1:4000
- 10 μg/mL or 1:400
- 100 μg/mL or 1:40 x-axis: CTRL.80R-IgG1, 2A-Fc, D8-IgG1, F10-IgG1, A66-IgG1, 17A.2.1.2, FERRET ANTI-SERUM

Fig. 5B

No Ab. | 2A-Fc | CTRL. 80R-IgG1
D8-IgG1 | F10-IgG1 | A66-IgG1

ANTIBODIES AGAINST INFLUENZA VIRUS AND METHODS OF USE THEREOF

RELATED APPLICATIONS

This application is a continuation of U.S. application Ser. No. 12/746,622, filed Oct. 4, 2010, which is a National Stage Entry Application and claims benefit of priority of International Application No. PCT/US2008/085876, filed Dec. 8, 2008, which claims benefit of priority under 35 USC § 119(e) to U.S. Provisional Application No. 61/005,725, filed Dec. 6, 2007 and U.S. Provisional Application No. 61/091,599, filed Aug. 25, 2008, the contents of which are incorporated herein by reference in their entirety.

GRANT SUPPORT

This invention was made with United States Government support under National Institutes of Health Grants U01 AI074518-01. The United States Government has certain rights in the invention.

INCORPORATION BY REFERENCE OF SEQUENCE LISTING

The contents of the text file named "20363-049C01US_ST25.txt", which was created on Aug. 12, 2013 and is 59 KB in size, are hereby incorporated by reference in their entirety.

FIELD OF THE INVENTION

This invention relates generally to anti-viral antibodies as well as to methods for use thereof.

BACKGROUND

An influenza pandemic represents one of the greatest acute infectious threats to human health. The 1918-1919 influenza pandemic caused an estimated 500,000 deaths in the United States, making it the most fatal event in all of US history. The spread of highly pathogenic avian influenza (HPAI) H5N1 influenza across Asia and now to the middle east and northern Africa creates a substantial risk for a new pandemic to arise.

Natural variation as well as escape mutants suggests that continued evolution of the virus should impact the decision on which strain(s) should be used for passive and active immunization. Although a number of important epitope mapping and neutralization escape studies have been reported new neutralizing antibodies and related structural studies are needed to develop immunization strategies against HPAI H5N1. The challenges to developing a protective vaccine against HPAI H5N1 are formidable and new approaches are needed to prevent and treat human infection by an ever changing enemy. There is a need to rapidly develop therapeutic strategies to elicit protective hosts immunity, both passively and actively.

Tremendous advances in the field of human antibody (Ab) engineering have been made. Monoclonal antibody (Mab) based immunotherapies are now becoming standard of care in an increasing number of human diseases including RSV. The shift toward de novo human Mab isolation and their clinical use is in part due to new antibody display and other library screening techniques that are now be exploited to build human antibodies with high affinity and specificity. Human Mab immunotherapies can provide an increasingly important role in clinical management of human diseases.

SUMMARY OF THE INVENTION

The invention is based upon the discovery of monoclonal antibodies which neutralize the influenza virus, e.g. influenza A virus. The influenza A virus is a Group I influenza A virus such as a H1 cluster influenza virus. The H1 cluster influenza virus is an H1a cluster or an H1b cluster. The monoclonal antibody is fully human. In various aspects, the monoclonal antibody is a bivalent antibody, a monovalent antibody, a single chain antibody or fragment thereof. Specifically, such monoclonal bind to an epitope on the stem region of the hemagglutinin protein (HA), such as HA1 or HA2 polypeptide. The epitope is non-linear.

Optionally, the epitope comprises both the HA-1 and HA-2. The epitope is non-linear. In some embodiments the epitope comprises the amino acid position 18, 38, 40, 291 of the HA1 polypeptide and the amino acid at position 18, 19, 20, 21, 38, 41, 42, 45, 49, 52, 53 and 56 of the HA2 polypeptide.

Exemplary monoclonal antibodies include monoclonal antibody D7, D8, F10, G17, H40, A66, D80, E88, E90, or H98 or an antibody that binds to the same epitope as D7, D8, F10, G17, H40, A66, D80, E88, E90, or H98.

The monoclonal antibodies of the invention can have the binding affinity of monoclonal antibody D7, D8, F10, G17, H40, A66, D80, E88, E90, or H98. Alternatively, the binding affinity can range about 1 pM to about 200 mM. The monoclonal antibodies of the invention function to inhibit viral and cell membrane fusion.

The monoclonal antibody has a heavy chain variable amino acid sequence containing SEQ ID NOS: 2, 6, 12, 18, 24, 28, 32, and 36 and/or a light chain variable amino acid sequence containing SEQ ID NOS: 4, 8, 14, 16, 20, 22, 26, 30, 34, and 38.

The monoclonal antibody, has a heavy chain variable nucleic acid sequence containing SEQ ID NOS: 1, 5, 13, 15, 21, 23, 29, 33, 37, and 40 and or a light chain variable nucleic acid sequence containing SEQ ID NOS: 3, 9, 11, 17, 19, 25, 27, 31, 35, 39, and 42

Also provided by the invention is a monoclonal anti-influenza hemagglutinin protein antibody or fragment thereof, where the antibody has a $V_H$ CDR1 region having the amino acid sequence SYAFS (SEQ ID NO: 43), TNAFS (SEQ ID NO: 44), AYAFT (SEQ ID NO: 45), SFAIS (SEQ ID NO: 46), SYAIS (SEQ ID NO: 47), GYYIH (SEQ ID NO: 48), MTAFT (SEQ ID NO: 49), or DNAIS (SEQ ID NO: 50); a $V_H$ CDR2 region having the amino acid sequence GIIPMFGTPNYAQKFQG (SEQ ID NO: 51), GVIPLFRTASYAQNVQG (SEQ ID NO: 52), GIIGMFGTANYAQKFQG (SEQ ID NO: 53), GISPMFGTPNYAQKFQG (SEQ ID NO: 54), GIIGVFGVPKYAQKFQG (SEQ ID NO: 55), WINPMTGGTNYAQKFQV (SEQ ID NO: 56), GISPIFRTPKYAQKFQG (SEQ ID NO: 57), or GIIPIFGKPNYAQKFQG (SEQ ID NO: 58); a $V_H$ CDR3 region having the amino acid sequence SSGYYYG GGFDV (SEQ ID NO: 59), SSGYHFGRSHFDS (SEQ ID NO: 60), GLYYYESSLDY (SEQ ID NO: 61), SPSYICSGGTCVFDH (SEQ ID NO: 62), EPGYYVGKNGFDV (SEQ ID NO: 63), GASVLRYFDWQPEALDI (SEQ ID NO: 64), TLSSYQPNNDAFAI (SEQ ID NO: 65), or DSDAYYYGSGGMDV (SEQ ID NO: 66); a $V_L$ CDR1 region having amino acid sequence TGSSSNIGNYVA (SEQ ID NO: 67), TGSSSNIAANYVQ (SEQ ID NO: 68), TGTSSDVGGYNSVS (SEQ ID NO: 69), TGNSNNVGN- QGAA (SEQ ID NO: 70), TGDSNNVGHQGTA (SEQ ID NO: 71), GGNNIGGYSVH (SEQ ID NO: 72), RASQSVSSYLA (SEQ ID NO: 73), RASQSLSSKYLA (SEQ ID NO: 74), TGSSSNIGNYVA (SEQ ID NO: 75), SGSSSNIGSNTVN (SEQ ID NO: 76), RASQSISSYLN (SEQ ID NO: 77), or TLSSGHSNYIIA (SEQ ID NO: 78); a V$_L$ CDR2 region having the amino acid sequence SNSDRPS (SEQ ID NO: 79), EDDRRPS (SEQ ID NO: 80), EVTKRPSU (SEQ ID NO: 81), RNNDRPS (SEQ ID NO: 82), RNGNRPS (SEQ ID NO: 83), DDKDRPS (SEQ ID NO: 84), DASNRAT (SEQ ID NO: 85), GASSRAT (SEQ ID NO: 86), SNNQRPS (SEQ ID NO: 87), AASSLQR (SEQ ID NO: 88), SNEQRPS (SEQ ID NO: 89), or VNSDGSHTKGD (SEQ ID NO: 90) and/or a V$_L$ CDR3 region having the amino acid sequence QSYDSLSAYV (SEQ ID NO: 91), QSYDTNNHAV (SEQ ID NO: 92), CSYAGHSAYV (SEQ ID NO: 93), STWDSSLSAVV (SEQ ID NO: 94), SVWDSSLSAWV (SEQ ID NO: 95), QVWDSGNDRPL (SEQ ID NO: 96), QQYGSSPQV (SEQ ID NO: 97), QQYDGVPRT (SEQ ID NO: 98), QSYDSRLSASL (SEQ ID NO: 99), QQYDSSPYT (SEQ ID NO: 100), ASWDDNLSGWV (SEQ ID NO: 101), or ETWDTKIHV (SEQ ID NO: 102).

In a further aspect, the invention provides An isolated an monoclonal anti-influenza hemagglutinin protein antibody or fragment thereof where the antibody has a VH amino acid sequence encoded by the VH germline gene IGHV1-69*01 and the amino acid at position: a) 27 is a valine; b) 28 is threonine; c) 30 is serine; d) 31 is serine; e) 54 is methionine; f) 55 is phenylalanine; g) 58 is threonine; h) 100 is proloine; i) 101 is serine; j) 102 is tyrosine; k) 103 is isoleucine and 105 is serine.

In another aspect, the invention provides a method of preventing or treating a disease or disorder caused by an influenza virus by administering to a person at risk of suffering from said disease or disorder, a therapeutically effective amount of a monoclonal antibody or scFV antibody described herein. The monoclonal antibody or scFV antibody is administered at a dose sufficient to neutralize the influenza virus. In embodiments of the invention, the method also includes administering an anti-viral drug, a viral entry inhibitor or a viral attachment inhibitor. The anti-viral drug is neuraminidase inhibitor such as zanamivir, or oseltamivir phosphate, a HA inhibitor, a sialic acid inhibitor or an M2 ion channel such as amantadine or rimantadine. The antibody is administered prior t or after exposure to an influenza virus In another aspect, the invention provides a method of detecting the presence of a an influenza virus in a sample by contacting the sample with a monoclonal antibody as described herein, and detecting the presence or absence of an antibody-antigen complex, thereby detecting the presence of a influenza virus in a sample. The test sample is generally obtained from blood, hair, cheek scraping or swab, saliva, biopsy, urine, feces, sputum, nasal aspiration, or semen.

The invention is further based upon the discovery of a protocol for generating broadly neutralizing human antibodies that target a highly conserved epitope in the stem region of HA. By using the trimeric H5 ectodomain expressed in baculovirus which produces shorter N-glycans and uncharged mannoses absorbed on a plastic surface, allowed for the dominant presentation of the stem epitope while masking the normally immunodominat globular head.

Accordingly, also included in the invention is a method of producing an isolated antibody that specifically binds a pathogenic enveloped virus by exposing a single chain or Fab expression library to a membrane fusion protein of the virus, identifying an antibody in the library that specifically binds said protein; and isolating the antibody from the library. Preferably, the fusion protein is immobilized on a solid surface, e.g. plastic. In various aspects the fusion protein has modified glycosylations compared to a wild type fusion protein. For example, the fusion is produced in a non-mammalian cell, such as an insect cell. The fusion protein is for example a trimeric hemagglutinin (HA) protein The invention further provides a method of vaccinating a subject against pathogenic enveloped virus such as an influenza virus by administering to the subject a membrane fusion protein (e.g., a trimeric hemagglutinin (HA) protein coated) or embedded in a biologically compatible matrix. In various aspects the fusion protein has modified glycosylations compared to a wild type fusion protein.

In another aspect, the invention provides a composition comprising a monoclonal antibody as described herein and kits containing the composition in one or more containers and instructions for use.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 1A is an illustration of the structure of the A/Vietnam 1203/04 trimer. The receptor binding site and antigenic variation sites are highlighted on the monomer.

FIG. 1B is an illustration showing the location of amino acid residues in the HA of H5N1 influenza viruses that are under positive selection FIG. 2 is a schematic illustration of convergent combination Immunotherapy for H5N1.

FIG. 3 is an illustration showing an amino acid sequence comparison of the framework regions 1-4 (FR1-4) and the complementary-determining regions 1-3 (CDR1-3) for both the VH (full-length sequences disclosed as SEQ ID NOS: 110-117, respectively, in order of appearance) and VL (full-length sequences disclosed as SEQ ID NOS: 8, 14, 20, 26, 30, 34, 16, 38, 22, and 10, respectively, in order of appearance) of the anti-influenza antibodies of the invention. FR and CDR regions are defined using Kabat database. The VH and VL gene name are shown on the right (using IMGT database). Dots show sequence identity to the consensus sequence. Hyphens represent gaps. FIG. 3 discloses the VH "CDR1" as SEQ ID NOS: 118-125, "CDR2" as SEQ ID NOS: 126-133, and "CDR3" as SEQ ID NOS: 170 and 134-139, all respectively, in order of appearance. For example, antibody F10/E90 has a heavy chain consisting of a CDR1 with the sequence EVTFSSFA (SEQ ID NO: 120); a CDR2 with the sequence ISPMFGTP (SEQ ID NO: 128); and a CDR3 with the sequence ARSPSYICSGGTCVFDH (SEQ ID NO: 134). Antibody D8/D80 has a heavy chain consisting of a CDR1 with the sequence GGTFSAYA (SEQ ID NO: 121); a CDR2 with the sequence IIGMFGTA (SEQ ID NO: 129); and a CDR3 with the sequence ARG- LYYYESSFDY (SEQ ID NO: 136). Antibody A66/E88 has a heavy chain consisting of a CDR1 with the sequence GGPFSMTA (SEQ ID NO: 122); a CDR2 with the sequence ISPIFRTP (SEQ ID NO: 130); and a CDR3 with the sequence ARTLSSYQPNNDAFAI (SEQ ID NO: 136). Antibody G17 has a heavy chain consisting of a CDR1 with the sequence GVTFSSYA (SEQ ID NO: 123); a CDR2 with the sequence IIGVFGVP (SEQ ID NO: 131); and a CDR3 with the sequence AREPGYYVGKNGFDV (SEQ ID NO: 137). Antibody D7/H98 has a heavy chain consisting of a CDR1 with the sequence GGIFNTNA (SEQ ID NO: 124); a CDR2 with the sequence VIPLFRTA (SEQ ID NO: 132); and a CDR3 with the sequence ARSSGYHFRSH (SEQ ID NO: 138). Antibody H40 has a heavy chain consisting of a CDR1 with the sequence GYTFTGYY (SEQ ID NO: 125); a CDR2 with the sequence INPMTGGTP (SEQ ID NO: 133); and a CDR3 with the sequence ARGASVLRYFD-WQPEALDI (SEQ ID NO: 139). FIG. 3 also discloses the VL "CDR1" as SEQ ID NOS: 140-149, "CDR2" as SEQ ID NOS: 150-159; and "CDR3" as SEQ ID NOS 160-169, all respectively, in order of appearance. For example, antibody D7 has a light chain consisting of a CDR1 with the sequence SGNIAANY (SEQ ID NO: 140); a CDR2 with the sequence EDD (SEQ ID NO: 150); and a CDR3 with the sequence QTYDTNNHAV (SEQ ID NO: 160). Antibody D8 has a light chain consisting of a CDR1 with the sequence SSD-VGGYNS (SEQ ID NO: 141); a CDR2 with the sequence EVT (SEQ ID NO: 151); and a CDR3 with the sequence CSYAGHSAYV (SEQ ID NO: 161). Antibody F10 has a light chain consisting of a CDR1 with the sequence SNNVGNQG (SEQ ID NO: 142); a CDR2 with the sequence RNN (SEQ ID NO: 152); and a CDR3 with the sequence STWDSSLSAVV (SEQ ID NO: 162). Antibody G17 has a light chain consisting of a CDR1 with the sequence SNNVGHQG (SEQ ID NO: 143); a CDR2 with the sequence RNG (SEQ ID NO: 153); and a CDR3 with the sequence SVWDSSLSAWV (SEQ ID NO: 163). Antibody H40 has a light chain consisting of a CDR1 with the sequence NIGGYS (SEQ ID NO: 144); a CDR2 with the sequence DDK (SEQ ID NO: 154); and a CDR3 with the sequence QVWDSGNDRPL (SEQ ID NO: 164). Antibody A66 has a light chain consisting of a CDR1 with the sequence QSVSSY (SEQ ID NO: 145); a CDR2 with the sequence DAS (SEQ ID NO: 155); and a CDR3 with the sequence QQYGSSPQ (SEQ ID NO: 165). Antibody D80 has a light chain consisting of a CDR1 with the sequence QSLSSKY (SEQ ID NO: 146); a CDR2 with the sequence GAS (SEQ ID NO: 156); and a CDR3 with the sequence QQYDGVPRT (SEQ ID NO: 166). Antibody E88 has a light chain consisting of a CDR1 with the sequence SSNIGSNT (SEQ ID NO: 147); a CDR2 with the sequence SNN (SEQ ID NO: 157); and a CDR3 with the sequence QSYDSRL-SASL (SEQ ID NO: 167). Antibody E90 has a light chain consisting of a CDR1 with the sequence QSISSY (SEQ ID NO: 148); a CDR2 with the sequence AAS (SEQ ID NO: 158); and a CDR3 with the sequence QQYDSSPYT (SEQ ID NO: 168). Antibody H98 has a light chain consisting of a CDR1 with the sequence TSNIGRNH (SEQ ID NO: 149); a CDR2 with the sequence SNE (SEQ ID NO: 159); and a CDR3 with the sequence ASWDDNLSGWV (SEQ ID NO: 169). FIG. 3 also discloses "QVQLVQSGAEV" as SEQ ID NO: 171 and "VTVSS" as SEQ ID NO: 172.

FIG. 5 shows the Neutralization mechanism. (a) Virus binding inhibition assay using full-length HA of H5-TH04-pseudotyped HIV-1 viruses. The binding of virus to cells in Ab-treated groups were compared with binding to cells in the absence of Ab (defined as 100%). None of the three nAbs (D8, F10 and A66) inhibited virus binding to cells, while a mouse anti-H5 mAb, 17A2.1.2, and ferret anti-H5N1 serum, both of which inhibit haemagglutination and presumably bind to the head, reduced binding significantly. (b) Inhibition of syncytia formation by nAbs. HeLa cells were transfected with H5-TH04-expressing plasmid. Syncytia formation induced by brief exposure to pH 5.0 buffer was completely inhibited by nAbs D8, F10 and A66, at 20 μg/ml, whereas control and an anti-HA1 mAb (2A) at the same concentration had no effect.

DETAILED DESCRIPTION OF THE INVENTION

Figure 4A:
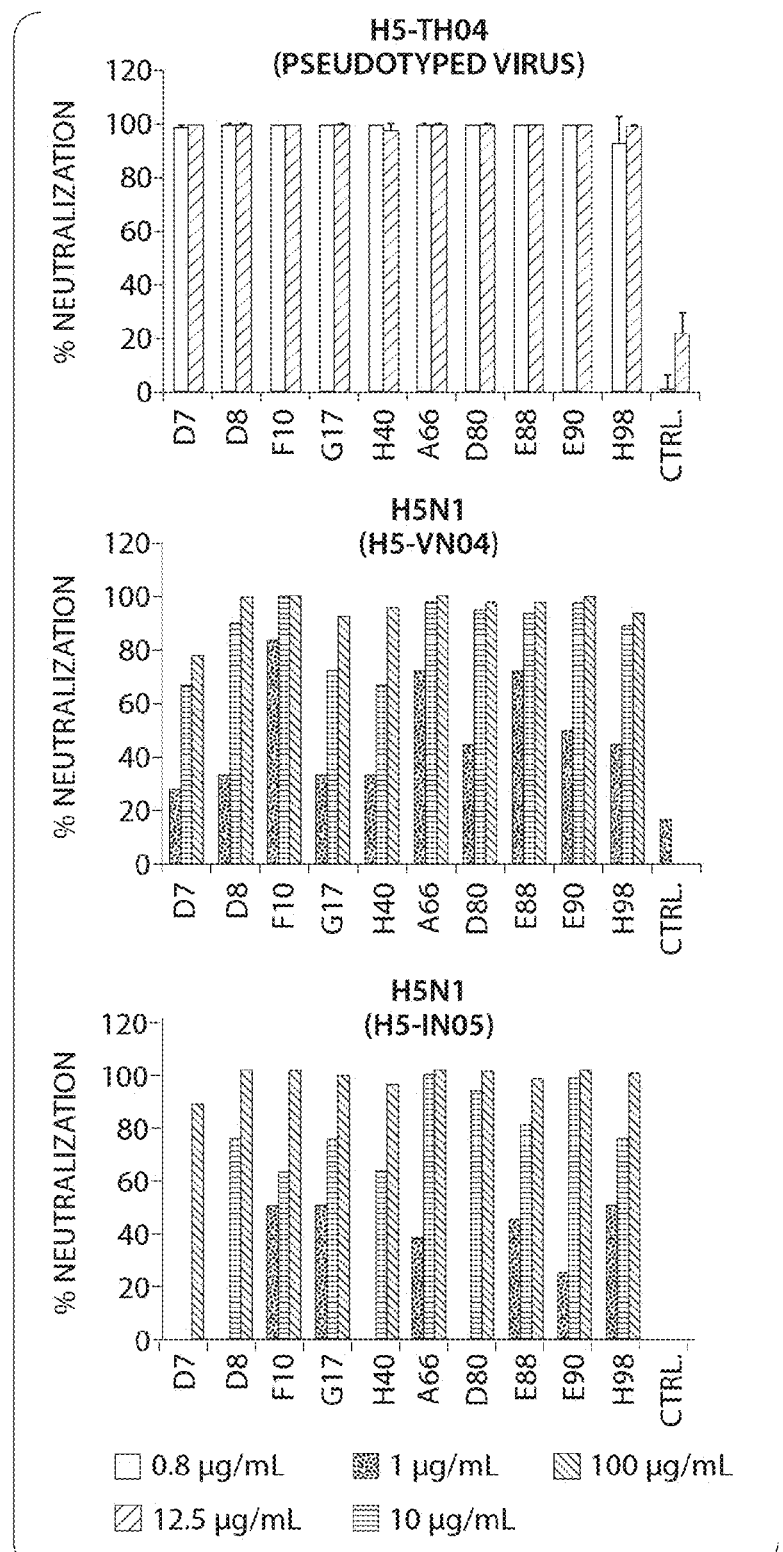
FIG. 4 shows in vitro neutralization of anti-H5 antibodies. (a) (Top panel) The 10 nAbs were converted to soluble scFv-Fcs (single chain fragment of variable region linked with Hinge, CH2 and CH3) and evaluated for neutralizing activity against H5-TH04-pseudotyped viruses. The percentage neutralization at 2 concentrations is shown with standard error bars. The mAb 80R[16] was used as the control (Ctrl.). (Middle and bottom panels), Neutralization of wild type H5-VN04 and H5-1N05 by the 10 scFv-Fcs at three concentrations using a plaque reduction assay. Results are consistent with those obtained from a microneutralization assay (data not shown). (b) Cross subtype neutralization. nAbs D8, F10 and A66 all neutralized H5-TH04, H1-SC1918 ((A/South Carolina/1/1918 (H1N1)), H1-PR34 (A/Puerto Rico/8/34 (H1N1)), H2-JP57 (A/Japan/305/57 (H2N2)) and H6-NY98 (A/chicken/New York/14677-13/1998 (H6N2)) pseudotyped viruses. (c) Microneutralization assay. Neutralization titers of F10 against wild-type H5N1, H1N1 (A/Ohio/83 ("H1-OH83")) and H2N2 (A/Ann Arbor/6/60 ("H2-AA60")) compared with a murine mAb 21G8.6 raised against H5N1 and Ctrl. 80R (1 mg/mL Ab stock solution). "<" indicates a titer of less than 20. Results represent two independent experiments.

Influenza A is a negative-sense, single-stranded RNA virus, with an eight-segment genome encoding 10 proteins. It belongs to the family Orthomyxoviridae which includes the genera of influenza virus A, B and C as defined by the antigenicity of the nucleocapsid and matrix proteins. Generally, influenza A virus is associated with more severe disease in humans. Influenza A virus is further subtyped by two surface proteins, hemagglutinin (HA) which attaches the virion to the host cell for cell entry, and neuraminidase (NA) which facilitates the spread of the progeny virus by cleaving the host sialic acid attached to the progeny virus or cell surface.

There are 16 HA subtypes and 9 NA subtypes which make up all subtypes of influenza A viruses by various combinations of HA and NA. All combinations of the 16 HA and 9 NA virus subtypes are found in water fowl. Of the hundreds of strains of avian influenza A viruses, only four are known to have caused human infections: H5N1, H7N3, H7N7 and H9N2. In general, human infection with these viruses has resulted in mild symptoms and very little severe illness: there has been only one fatal case of pneumonia caused by H7N7. However, the exception is the highly pathogenic H5N1 virus, for which there is no natural immunity in humans. The infidelity of the RNA polymerase and the selective pressure of host immunity can lead to the accumulation of mutations and change in surface antigenicity of these proteins. This antigenic change is called antigenic drift. In addition, as a result of its segmented genome, shuffling of gene segments can occur if two different subtypes of influenza A virus infect the same cell. For example, if a human H3N2 virus and an avian H5N1 virus co-infect a human or other member of a mammalian species, such an event can produce a novel H5N2. This novel virus can then be efficiently transmitted from human to human because all of most of the gene segments come from the human virus. Such genetic reassortment would lead to a major antigen change, a so-called antigenic shift, which would mean that most of the global population would not have any neutralizing antibodies against the reassortant virus. Such a situation, coupled with the high mortality of influenza H5N1 pneumonia, is one of the most feared scenarios in the field of public health.

Influenza virus hemagglutinin (HA) is the most variable antigen of influenza virus, and is responsible for virus entry into cells. It is synthesized as a trimeric precursor polypeptide HA0 which is post-translationally cleaved to two polypeptides HA1 and HA2 linked by a single disulphide bond. The HA1 chain of HA is responsible for the attachment of virus to the cell surface. HA2 mediates the fusion of viral and cell membranes in endosomes, allowing the release of the ribonucleoprotein complex into the cytoplasm. In contrast to HA1, the HA2 molecule represents a relatively conserved part of HA. A second immunogenic influenza protein is neuraminidase (NA). This tetrameric glycoprotein is responsible for releasing virions from surface sialic acid on producer cells, and may also have a role in promoting access to target cells in the airways. Although neutralizing antibodies against NA are protective in animals and man, there is a paucity of data on their mechanisms of action. A recent report on the crystal structure of N1 neuraminidase demonstrated the presence of a cavity adjacent to its active site that may be exploited to develop new anti-influenza drugs, including antibodies. This finding is particularly important in light of the reports of emergence of drug resistance to oseltamivir (Tamiflu) and zanamivir (Relenza) for H5N1 viruses.

Both the HA1 and HA2 chains of HA are immunogenic and antibodies reactive with both chains have been demonstrated after natural infection in humans. While antibodies specific to HA1 are mostly neutralizing, different mechanism of virus neutralization by HA1 specific Mabs in vitro have been described including blocking the receptor site on HA1, intracellular inhibition of virus-cell fusion, or simultaneous attachment inhibition and virus-cell fusion inhibition, depending on antibody concentration. Although less well studied, inhibition of cell fusion by anti-HA2 antibodies has been reported.

More than two decades ago, the HA molecule of the H3 subtype was characterized by sequencing the HA of antigenic drift variants and escape mutants, and the antigenic epitopes were mapped on the molecule's three-dimensional structure. Since then, the antigenic sites on H1, H2 and H5 of an avian pathogenic virus were mapped on the three-dimensional structures of H3. After the outbreak of H5N1 infection in humans in Hong Kong in 1997 and the isolation of H9N2 virus from human cases in 1999, the X-ray structures of both proteins were solved. However, antigenic drift of the 1997 swine isolate (A/Duck/Singapore/3/97) that was used to solve the structure, and more recently isolated highly pathogenic strains, is significant. Indeed, there are 28 minor changes and two potentially major changes between the swine isolate (A/Duck/Singapore/3/97) and the HPAI H5N1 strain (A/Vietnam1203/04).

Phylogenetic analyses of the H5 HA genes from the 2004-2005 outbreak have shown two different lineages of HA genes, termed clades 1 and 2. HPAI H5N1 strain (A/Vietnam1203/04) is a member of Glade 1. Viruses in each of these clades are distributed in non-overlapping geographic regions of Asia. The H5N1 viruses from Indochina are tightly clustered within Glade 1, whereas H5N1 isolated from several surrounding countries are distinct from Glade 1 isolates, and belong in a more divergent Glade 2. Clade 1 viruses were isolated from humans and birds in Vietnam, Thailand and Cambodia but only from birds in Laos and Malaysia. The Glade 2 viruses were found in viruses isolated exclusively from birds in China, Indonesia, Japan, and South Korea. The most recent epidemiologic studies analyzed 82 H5N1 viruses isolated from poultry throughout Indonesia and Vietnam, as well as 11 human isolates from southern Vietnam together with sequence data available in public databases, to address questions relevant to virus introduction, endemicity and evolution[36]. Phylogenetic analysis showed that all viruses from Indonesia form a distinct sublineage of H5N1 genotype Z viruses, suggesting that this outbreak likely originated from a single introduction via spread throughout the country during the past two years. Continued virus activities in Indonesia were attributed to transmission via poultry movement within the country, rather than through repeated introductions by bird migration. Within Indonesia and Vietnam, H5N1 viruses have evolved over time into geographically distinct groups within each country.

Recently, the structure of HA from A/Vietnam1203/4 was solved. Comparison of its amino acid sequences with the HA genes from HPAI 2004 and 2005 isolates from Glade 1 and 2 viruses identified 13 positions of antigenic variation that are mainly clustered around the receptor binding domain, while the rest are within the vestigial esterase domain. Regions of antigenic variation have been identified in H1 and H3 serotypes (FIG. 1A). For H1, these sites are designated Sa, Sb, Ca and Cb while for H3, sites are designated A, B, C and D. Escape mutants of H5 HAs can be clustered into three epitopes; site 1: an exposed loop (HA1 140-145) that overlaps antigenic sites A of H3 and Ca2 of H$^2$; site 2: HA1 residues 156 and 157 that corresponds to antigenic site B in H3 serotypes; and 3) HA1 129-133, which is restricted to the Sa site in H1 HAs and H9 serotypes. In the recent studies by Smith, detection of positive selection at the amino acid level indicated that eight residues in the HA proteins were under positive selection (FIG. 1B). These residues include five in antigenic sites A and E (positions 83, 86, 138, 140 and 141); two involved in receptor binding (positions 129 and 175); and positions 156 is a site for potential N-linked glycosylation that is near the receptor-binding site. The results further revealed that three residues in HA (Val 86, Ser 129 and Thr 156) were more frequently observed in human isolates than in chicken or duck isolates and likely represented early adaptation of H5N1 genotype Z to humans. Another important finding from these studies is that the phylogenetic differences between the Indonesian and Vietnamese sub-lineages was also reflected in significant differences in antigenic cross-reactivity between these two group of viruses. Specifically, viruses from Indonesia did not react to ferret antisera against A/Vietnam1203/04, and representative viruses from Vietnam did not react with ferret antisera against Indonesian viruses IDN/5/06 and Dk/IDN/MS/04. These findings are in agreement with earlier studies with immune human serum and human 1997 and 2003 H5N1 viruses that these strains were not only phylogenetically but also antigenically distinct. Thus, natural variation as well as escape mutants suggests that continued evolution of the virus should impact the decision on which strain(s) should be used for passive and active immunization.

The instant invention provides methods for the identification, production and characterization of human anti-influenza monoclonal antibodies Identification and Characterization of scFvs and Monoclonal Antibodies High affinity, cross-subtype, broadly-neutralizing human anti-HA mAbs have been identified. These nAbs inhibit the post-attachment fusion process by recognizing a novel and highly conserved neutralizing epitope within the stem region at a point where key elements of the conformational change—the fusion peptide and the exposed surface of helix αA—are brought into close apposition. Structural and sequence analysis of all 16 HA subtypes points to the existence of only two variants of this epitope, corresponding to the two phylogenetic groupings of HA (Groups 1 and 2). These results raise the possibility that a small cocktail of nAbs derived from a subset of each group could provide broad protection against both seasonal and pandemic influenza.

A recent report utilized immune cells from H5N1-infected patients to isolate anti-HA nAbs. However, their epitopes and modes of action were not reported. Remarkably, we repeatedly isolated nAbs that utilizes the same VH germline gene, IGHV1-69*01, and encodes a CDR3 loop containing a tyrosine at an equivalent position to Y102, from a non-immune library. This suggests that broad anti-HA cross-immunity pre-exists in the H5-naive population, possibly due to previous exposure to H1, and, for library donors born before 1968, H2 subtypes. The recurrent use of this germline VH segment, the commonality of the CDR3 tyrosine introduced through N insertion and/or germline D gene assembly, and the promiscuous use of VL genes by the nAbs discovered in both studies, suggest that the precursor frequency of rearranged VH segments that could recognize this epitope is significant. This raises the possibility that with suitable exposure to the F10 epitope identified here, these broad-spectrum nAbs may be readily induced in vivo. While the genetic and structural complexity of nAbs required to provide universal protection against virus subtypes in both groups is still unknown, our data would seem to point to a surprisingly simple solution.

Three unique anti-HA-1 scFvs were identified by sequencing analysis of the 58 HA-1 positive clones. These scFvs were designated as 38 B and 1C. The VH and VL amino acid sequence of 2A is shown in FIG. 3.

Ten unique anti-HA0 scFvs were identified by sequencing analysis of the 97 HA0 positive clones. These scFvs were designated as 7, 8, 10, 17, 40, 66, 80, 88, 90, and 98. Six different VH and 10 different VL genes were revealed. Some scFvs shared the same VH gene. Five out of the six different VH genes belonged to the IGHV1-69 gene family. Three out of ten VL genes were kappa chain.

2A scFv is an moderate neutralizing antibody, 38B and 1C are non-neutralizing antibodies. Ten scFvs, 7, 8, 10, 17, 40, 66, 80, 88, 90, and 98 are potent neutralizing antibodies. (FIG. 6)

The nucleic acid and amino acid sequence of the neutralizing influenza antibodies are provided below:

TABLE 1A

Antibody 2A Variable Region nucleic acid sequences $V_H$ chain of 2A (SEQ ID NO: 1)

CAGGTGCAGCTGGTGCAGTCTGGGGCTGAGGTGAAGAAGCCTGGGTCCTCGGTGAAGGTCTCCTGCAAGGCTTCTGGAGG

CACCTTCAGTGACAATGCTATCAGCTGGGTGCGACAGGCCCCAGGACAAGGGCTTGAGTGGATGGGGGGCATCATTCCTA

TCTTTGGAAAACCAAACTACGCACAGAAGTTCCAGGGCAGAGTCACGATTACTGCGGACGAATCCACGAGCACAGCCTAC

ATGGACCTGAGGAGCCTGAGATCTGAGGACACGGCCGTTTATTACTGTGCGAGAGATTCAGACGCGTATTACTATGGTTC

GGGGGGTATGGACGTCTGGGGCCAAGGCACCCTGGTCACCGTCTCCTCA $V_L$ chain of 2A (SEQ ID NO: 3)

CTGCCTGTGCTGACTCAATCATCCTCTGCCTCTGCTTCCCTGGGATCCTCGGTCAAGCTCACCTGCACTCTGAGCAGTGG

GCATAGTAACTACATCATCGCATGGCATCAACAGCAGCCAGGGAAGGCCCCTCGGTACTTGATGAAGGTTAATAGTGATG

GCAGCCACACCAAGGGGGACGGGATCCCTGATCGCTTCTCAGGCTCCAGCTCTGGGGCTGACCGCTACCTCACCATCTCC

AACCTCCAGTCTGAGGATGAGGCTAGTTATTTCTGTGAGACCTGGGACACTAAGATTCATGTCTTCGGAACTGGGACCAA

GGTCTCCGTCCTCAG

TABLE 1B

Antibody 2A Variable Region amino acid sequences $V_H$ chain of 2A (SEQ ID NO: 2)

QVQLVQSGAEVKKPGSSVKVSCKASGGTFSDNAISWVRQAPGQGLEWMGGIIPIFGKPNYAQKFQGRVTITADESTSTAY

MDLRSLRSEDTAVYYCARDSDAYYYGSGGMDVWGQGTLVTVSS $V_L$ chain of 2A (SEQ ID NO: 4)

LPVLTQSSSASASLGSSVKLTCTLSSGHSNYIIAWHQQQPGKAPRYLMKVNSDGSHTKGDGIPDRFSGSSSGADRYLTIS

NLQSEDEASYFCETWDTKIHVFGTGTKVSVL

TABLE 1C

Antibody D7 Variable Region nucleic acid sequences
$V_H$ chain of D7
(SEQ ID NO: 5)
CAGGTGCAGCTGGTGCAgTCTGGGGCTGAGGTGAAGAAGCCTGGGTCCTCGGTGAAGGTCTCCTGCAAGGCTCCTGGAGG

TATCTTCAACACCAATGCTTTCAGCTGGGTCCGACAGGCCCCTGGACAAGGTCTTGAGTGGGTGGGAGGGGTCATCCCTT

TGTTTCGAACAGCAAGCTACGCACAGAACGTCCAGGGCAGAGTCACCATTACCGCGGACGAATCCACGAACACAGCCTAC

ATGGAGCTTACCAGCCTGAGATCTGCGGACACGGCCGTGTATTACTGTGCGAGAAGTAGTGGTTACCATTTTAGGAGTCA

CTTTGACTCCTGGGGCCTGGGAACCCTGGTCACCGTCTCCTCA $V_L$ chain of D7
(SEQ ID NO: 9)
AATTTTATGCTGACTCAGCCCCACTCTGTGTCGGCGTCTCCGGGGAAGACGGTGACCATCTCCTGCACCGGCAGCAGTGG

CAACATTGCCGCCAACTATGTGCAGTGGTACCAACAACGTCCGGGCAGTGCCCCCACTACTGTGATCTATGAGGATGACC

GAAGACCCTCTGGGGTCCCTGATCGGTTCTCTGGCTCCATCGACAGGTCCTCCAACTCTGCCTCCCTCACCATCTCAGGA

CTGAAGACTGAGGACGAGGCTGACTACTACTGTCAGACTTATGATACCAACAATCATGCTGTGTTCGGAGGAGGCACCCA

CCTGACCGTCCTC

TABLE 1D

Antibody H98 Variable Region nucleic acid sequences
$V_H$ chain of H98
(SEQ ID NO: 7)
CAGGTGCAGCTGGTGCAATCTGGGGCTGAGGTGAAGAAGCCTGGGTCCTCGGTGAAGGTCTCCTGCAAGGCTCCTGGAGG

TATCTTCAACACCAATGCTTTCAGCTGGGTCCGACAGGCCCCTGGACAAGGTCTTGAGTGGGTGGGAGGGGTCATCCCTT

TGTTTCGAACAGCAAGCTACGCACAGAACGTCCAGGGCAGAGTCACCATTACCGCGGACGAATCCACGAACACAGCCTAC

ATGGAGCTTACCAGCCTGAGATCTGCGGACACGGCCGTGTATTACTGTGCGAGAAGTAGTGGTTACCATTTTAGGAGTCA

CTTTGACTCCTGGGGCCTGGGAACCCTGGTCACCGTCTCCTCA $V_L$ chain of H98
(SEQ ID NO: 11)
TCCTATGAGCTGACTCAGCCACCCTCAGCGTCTGGGAAACACGGGCAGAGGGTCACCATCTCTTGTTCTGGAGGCACCTC

CAACATCGGACGTAATCATGTTAACTGGTACCAGCAACTCCCAGGAACGGCCCCCAAACTCCTCATCTATAGTAATGAAC

AGCGGCCCTCAGGGGTCCCTGACCGATTCTCTGGCTCCAAATCTGGCACCTCCGCCTCCCTGGCCGTGAGTGGGCTCCAG

TCTGAGGATGAGGCTGATTATTACTGTGCATCATGGGATGACAACTTGAGTGGTTGGGTGTTCGGCGGAGGGACCAAGCT

GACCGTCCTA

TABLE 1E

Antibody D7 and H98 Variable Region chain amino acid sequences
$V_H$ chain of D7 and H98
(SEQ ID NO: 6)
QVQLVQSGAEVKKPGSSVKVSCKAPGGIFNTNAFSWVRQAPGQGLEWVGGVIPLFRTASYAQNVQGRVTITADESTNTAY

MELTSLRSADTAVYYCARSSGYHFRSHFDSWGLGTLVTVSS $V_L$ chain of D7
(SEQ ID NO: 8)
NFMLTQPHSVSASPGKTVTISCTGSSGNIAANYVQWYQQRPGSAPTTVIYEDDRRPSGVPDRFSGSIDRSSNSASLTISG

LKTEDEADYYCQTYDTNNHAVFGGGTHLTVL

TABLE 1E-continued

V<sub>L</sub> chain of H98

(SEQ ID NO: 10)

SYELTQPPSASGKHGQRVTISCSGGTSNIGRNHVNWYQQLPGTAPKLLIYSNEQRPSGVPDRFSGSKSGTSASLAVSGLQ

SEDEADYYCASWDDNLSGWVFGGGTKLTVL

TABLE 1F

Antibody D8 Variable Region nucleic acid sequences
V<sub>H</sub> chain of D8

(SEQ ID NO: 13)

CAGGTGCAGCTGGTGCAGTCTGGGGCTGAGGTGAAGAAGCCTGGGTCCTCGGTGAAGGTCTCCTGCAAGGCTTCTGGAGG

CACCTTCAGCGCTTATGCTTTCACCTGGGTGCGGCAGGCCCCTGGACAAGGGCTTGAGTGGATGGGAGGCATCACCGGAA

TGTTTGGCACAGCAAACTACGCACAGAAGTTCCAGGGCAGAGTCACGATTACCGCGGACGAACTCACGAGCACAGCCTAC

ATGGAGTTGAGCTCCCTGACATCTGAAGACACGGCCCTTTATTATTGTGCGAGAGGATTGTATTACTATGAGAGTAGTCT

TGACTATTGGGGCCAGGGAACCCTGGTCACCGTCTCCTCAG

V<sub>L</sub> chain of D8

(SEQ ID NO: 17)

CAGTCTGTGCTGACTCAGCCACCCTCCGCGTCCGGGTCTCCTGGACAGTCAGTCACCATCTCCTGCACTGGAACCAGCAG

TGACGTTGGTGGTTATAACTCTGTCTCCTGGTACCAACAGCACCCAGGCAAAGCCCCCAAACTCATGATTTATGAGGTCA

CTAAGCGGCCCTCAGGGGTCCCTGATCGCTTCTCTGCCTCCAAGTCTGGCAACACGGCCTCCCTGACCGTCTCTGGGCTC

CAGGCTGAGGATGAGGCTGATTATTTCTGCTGCTCATATGCAGGCCACAGTGCTTATGTCTTCGGAACTGGGACCAAGGT

CACCGTCCTG

TABLE 1G

Antibody D80 Variable Region nucleic acid sequences
V<sub>H</sub> chain of D80

(SEQ ID NO: 15)

CAGGTGCAGCTGGTGCAGTCTGGGGCTGAGGTGAAGAAGCCTGGGTCCTCGGTGAAGGTCTCCTGCA,GGCTTCTGGAGG

CACCTTCAGCGCTTATGCTTTCACCTGGGTGCGGCAGGCCCCTGGACAAGGGCTTGAGTGGATGGGAGGCATCACCGGAA

TGTTTGGCACAGCAAACTACGCACAGAAGTTCCAGGGCAGAGTCACGATTACCGCGGACGAACTCACGAGCACAGCCTAC

ATGGAGTTGAGCTCCCTGACATCTGAAGACACGGCCCTTTATTATTGTGCGAGAGGATTGTATTACTATGAGAGTAGTCT

TGACTATTGGGGCCAGGGAACCCTGGTCACCGTCTCCTCAG

V<sub>K</sub> chain of D80

(SEQ ID NO: 19)

GAAATTGTGCTGACTCAGTCTCCAGGCACCCTGTCTTTGTCTCCAGGGGAAAGAGCCACCCTCTCCTGCAGGGCCAGTCA

GAGTCTTAGCAGCAAGTACTTAGCCTGGTATCAGCAGAAACCTGGCCAGGCTCCCAGGCTCCTCATCTATGGTGCATCCA

GCAGGGCCACTGGCATCCCAGACAGGTTCAGTGGCAGTGGGTCTGGGACAGACTTCACCCTCACCATCAGTAGACTGGAG

CCTGAAGATTTTGCAGTGTATTCCTGTCAGCAGTATGATGGCGTACCTCGGACGTTCGGCCAAGGGACCACGGTGGAAAT

CAAA

TABLE 1H

Antibody D8 and D80 Variable Region chain amino acid sequences
V<sub>H</sub> chain of D8 and D80

(SEQ ID NO: 12)

QVQLVQSGAEVKKPGSSVKVSCKASGGTFSAYAFTWVRQAPGQGLEWMGGITGMFGTANYAQKFQGRVTITADELTSTAY

MELSSLTSEDTALYYCARGLYYYESSLDYWGQGTLVTVSS

TABLE 1H-continued

V_L chain of D8
(SEQ ID NO: 14)
QSVLTQPPSASGSPGQSVTISCTGTSSDVGGYNSVSWYQQHPGKAPKLMIYEVTKRPSGVPDRFSASKSGNTASLTVSGL

QAEDEADYFCCSYAGHSAYVFGTGTKVTVL

V_K chain of D80
(SEQ ID NO: 16)
EIVLTQSPGTLSLSPGERATLSCRASQSLSSKYLAWYQQKPGQAPRLLIYGASSRATGIPDRFSGSGSGTDFTLTISRLE

PEDFAVYSCQQYDGVPRTFGQGTTVEIK

TABLE 1I

Antibody F10 Variable Region nucleic acid sequences
V_H chain of F10
(SEQ ID NO: 21)
CAGGTGCAGCTGGTGCAGTCAGGGGCTGAGGTGAAGAAGCCTGGGTCCTCGGTGAAGGTCTCCTGCACGTCCTCTGAAGT

CACCTTCAGTAGTTTTGCTATCAGCTGGGTGCGACAGGCCCCTGGACAAGGGCTTGAGTGGCTGGGAGGGATCAGCCCTA

TGTTTGGAACACCTAATTACGCGCAGAAGTTCCAAGGCAGAGTCACCATTACCGCGGACCAGTCCACGAGGACAGCCTAC

ATGGACCTGAGGAGCCTGAGATCTGAGGACACGGCCGTGTATTATTGTGCGAGATCTCCTTCTTACATTTGTTCTGGTGG

AACCTGCGTCTTTGACCATTGGGGCCAGGGAACCCTGGTCACCGTCTCCTCA

V_L chain of F10
(SEQ ID NO: 25)
CAGCCTGGGCTGACTCAGCCACCCTCGGTGTCCAAGGGCTTGAGACAGACCGCCACACTCACCTGCACTGGGAACAGCAA

CAATGTTGGCAACCAAGGAGCAGCTTGGCTGCAGCAGCACCAGGGCCACCCTCCCAAACTCCTATCCTACAGGAATAATG

ACCGGCCCTCAGGGATCTCAGAGAGATTCTCTGCATCCAGGTCAGGAAACACAGCCTCCCTGACCATTACTGGACTCCAG

CCTGAGGACGAGGCTGACTATTACTGCTCAACATGGGACAGCAGCCTCAGTGCTGTGGTATTCGGCGGAGGGACCAAGCT

GACCGTCCTA

TABLE 1J

Antibody E90 Variable Region nucleic acid sequences
V_H chain of E90
(SEQ ID NO: 23)
CAGGTACAGCTGCAGCAGTCAGGGGCTGAGGTGAAGAAGCCTGGGTCCTCGGTGAAGGTCTCCTGCACGTCCTCTGAAGT

CACCTTCAGTAGTTTTGCTATCAGCTGGGTGCGACAGGCCCCTGGACAAGGGCTTGAGTGGCTGGGAGGGATCAGCCCTA

TGTTTGGAACACCTAATTACGCGCAGAAGTTCCAAGGCAGAGTCACCATTACCGCGGACCAGTCCACGAGGACAGCCTAC

ATGGACCTGAGGAGCCTGAGATCTGAGGACACGGCCGTGTATTATTGTGCGAGATCTCCTTCTTACATTTGTTCTGGTGG

AACCTGCGTCTTTGACCATTGGGGCCAGGGAACCCTGGTCACCGTCTCCTCA

V_L chain of E90
(SEQ ID NO: 27)
GACATCCAGATGACCCAGTCTCCATCCTCCCTGTCTGCATCTGTAGGAGACAGAGTCACCATCACTTGCCGGGCAAGTCA

GAGCATTAGCAGCTATTTAAATTGGTATCAGCAGAAACCAGGGAAAGCCCCTAAGCTCCTGATCTATGCTGCATCCAGTT

TGCAAAGAGGGGTCCCATCAAGGTTCAGTGGCAGTGGATCTGGGACAGACTTCACTCTCACCATTAGCAGCCTGCAGCCT

GAAGATTTTGCAGTGTATTACTGTCAGCAGTATGATAGTTCACCGTACACTTTTGGCCAGGGGACCAAGGTAGAGATCAA

A

TABLE 1K

Antibody F10 and E90 Variable Region amino acid sequences
V<sub>H</sub> chain of F10 and E90

(SEQ ID NO: 18)
QVQLVQSGAEVKKPGSSVKVSCTSSEVTFSSFAISWVRQAPGQGLEWLGGISPMFGTPNYAQKFQGRVTITADQSTRTAY

MDLRSLRSEDTAVYYCARSPSYICSGGTCVFDHWGQGTLVTVSS

V<sub>L</sub> chain of F10

(SEQ ID NO: 20)
QPGLTQPPSVSKGLRQTATLTCTGNSNNVGNQGAAWLQQHQGHPPKLLSYRNNDRPSGISERFSASRSGNTASLTITGLQ

PEDEADYYCSTWDSSLSAVVFGGGTKLTVL

V<sub>L</sub> chain of E90

(SEQ ID NO: 22)
DIQMTQSPSSLSASVGDRVTITCRASQSISSYLNWYQQKPGKAPKLLIYAASSLQRGVPSRFSGSGSGTDFTLTISSLQP

EDFAVYYCQQYDSSPYTFGQGTKVEIK

TABLE 1L

Antibody G17 Variable Region nucleic acid sequences
V<sub>H</sub> chain of G17

(SEQ ID NO: 29)
CAGGTGCAGCTGGTGCAATCTGGGGCTGAAGTGAAGAAGCCTGGGGCCTCAGTGAAGGTCTCCTGCAAGACTTCTGGAGT

CACCTTCAGCAGCTATGCTATCAGTTGGGTGCGACAGGCCCCTGGACAAGGGCTTGAGTGGATGGGAGGGATCATCGGTG

TCTTTGGTGTACCAAAGTACGCGCAGAACTTCCAGGGCAGAGTCACAATTACCGCGGACAAACCGACGAGTACAGTCTAC

ATGGAGCTGAACAGCCTGAGAGCTGAGGACACGGCCGTGTATTACTGTGCGAGAGAGCCCGGGTACTACGTAGGAAAGAA

TGGTTTTGATGTCTGGGGCCAAGGGACAATGGTCACCGTCTCTTCA

V<sub>L</sub> chain of G17

(SEQ ID NO: 31)
TCCTATGAGCTGACTCAGCCACCCTCGGTGTCCAAGGGCTTGAGACAGACCGCCATACTCACCTGCACTGGAGACAGCAA

CAATGTTGGCCACCAAGGTACAGCTTGGCTGCAACAACACCAGGGCCACCCTCCCAAACTCCTATCCTACAGGAATGGCA

ACCGGCCCTCAGGGATCTCAGAGAGATTCTCTGCATCCAGGTCAGGAAATACAGCCTCCCTGACCATTATTGGACTCCAG

CCTGAGGACGAGGCTGACTACTACTGCTCAGTATGGGACAGCAGCCTCAGTGCCTGGGTGTTCGGCGGAGGGACCAAGCT

GACCGTCCTA

TABLE 1M

Antibody G17 Variable Region amino acid sequences
V<sub>H</sub> chain of G17

(SEQ ID NO: 24)
QVQLVQSGAEVKKPGASVKVSCKTSGVTFSSYAISWVRQAPGQGLEWMGGIIGVFGVPKYAQNFQGRVTITADKPTSTVY

MELNSLRAEDTAVYYCAREPGYYVGKNGFDVWGQGTMVTVSS

V<sub>L</sub> chain of G17

(SEQ ID NO: 26)
SYELTQPPSVSKGLRQTAILTCTGDSNNVGHQGTAWLQQHQGHPPKLLSYRNGNRPSGISERFSASRSGNTASLTIIGLQ

PEDEADYYCSVWDSSLSAWVFGGGTKLTVL

TABLE 1N

Antibody 1140 Variable Region nucleic acid sequences
V<sub>H</sub> chain of H40

(SEQ ID NO: 33)
CAGGTGCAGCTGGTGCAGTCTGGGGCTGAGGTGAGGAAGCCTGGGGCCTCAGTGAAGGTCTCATGTAAGGCTTCTGGATA

CACCTTCACCGGTTATTATATTCACTGGGTGCGACAGGCCCCTGGACAAGGACTTGAGTGGATGGGTTGGATCAACCCTA

TABLE 1N-continued

TGACTGGTGGCACAAACTATGCACAGAAGTTTCAGGTCTGGGTCACCATGACCCGGGACACGTCCATCAACACAGCCTAC

ATGGAGGTGAGCAGGCTGACATCTGACGACACGGCCGTGTATTACTGTGCGAGGGGGGCTTCCGTATTACGATATTTTGA

CTGGCAGCCCGAGGCTCTTGATATCTGGGGCCTCGGGACCACGGTCACCGTCTCCTCA $V_L$ chain of H40
(SEQ ID NO: 35)
CAGCCTGTGCTGACTCAGCCACCCTCGGTGTCAGTGGCCCCAGGACAGACGGCCAGCATTCCCTGTGGGGGGAACAACAT

TGGAGGCTACAGTGTACACTGGTACCAACAAAAGCCGGGCCAGGCCCCCCTCTTGGTCATTTATGACGATAAAGACCGGC

CCTCAGGGATCCCTGAGCGATTCTCTGGCGCCAACTCTGGGAGCACGGCCACCCTGACAATCAGCAGGGTCGAAGCCGGG

GATGAGGGCGACTACTACTGTCAGGTGTGGGATAGTGGTAATGATCGTCCGCTGTTCGGCGGAGGGACCAAGCTGACCGT

CCTA

TABLE 1O

Antibody 1140 Variable Region amino acid sequences
$V_H$ chain of H40
(SEQ ID NO: 28)
QVQLVQSGAEVRKPGASVKVSCKASGYTFTGYYIHWVRQAPGQGLEWMGWTNPMTGGTNYAQKFQVWVTMTRDTSINTAY

MEVSRLTSDDTAVYYCARGASVLRYFDWQPEALDIWGLGTTVTVSS $V_L$ chain of H40
(SEQ ID NO: 30)
QPVLTQPPSVSVAPGQTASIPCGGNNIGGYSVHWYQQKPGQAPLLVIYDDKDRPSGIPERFSGANSGSTATLTISRVEAG

DEGDYYCQVWDSGNDRPLEGGGTKLTVL

TABLE 1P

Antibody A66 Variable Region nucleic acid sequences
$V_H$ chain of A66
(SEQ ID NO: 37)
CAGGTGCAGCTGGTGCAGTCTGGGGCTGAAGTGAAGAAGCCTGGCTCCTCGGTGAAGGTTTCCTGCAAGGCTTCTGGAGG

CCCCTTCAGCATGACTGCTTTCACCTGGCTGCGACAGGCCCCTGGACAAGGGCTTGAGTGGATGGGTGGGATCAGCCCTA

TCTTTCGTACACCGAAGTACGCACAGAAGTTCCAGGGCAGAGTCACGATTACCGCGGACGAATCCACGAACACAGCCAAC

ATGGAGCTGACCAGCCTGAAATCTGAGGACACGGCCGTGTATTACTGTGCGAGAACCCTTTCCTCCTACCAACCGAATAA

TGATGCTTTTGCTATCTGGGGCCAAGGGACAATGGTCACCGTCTCTTCA $V_K$ chain of A66
(SEQ ID NO: 39)
GAAATTGTGTTGACGCAGTCTCCAGCCACCCTGTCTTTGTCTCCAGGGGAAAGAGCCACCCTCTCCTGCAGGGCCAGTCA

GAGTGTTAGCAGCTACTTAGCCTGGTACCAACAGAAACCTGGCCAGGCTCCCAGGCTCCTCATCTATGATGCATCCAACA

GGGCCACTGGCATCCCAGCCAGGTTCAGTGGCAGTGGGTCTGGGACAGACTTCACTCTCACCATCAGCAGACTGGAGCCT

GAAGATTTTGCAGTCTATTTCTGTCAGCAGTATGGTAGCTCACCTCAATTCGGCCAAGGGACACGACTGGAGATTAAA

TABLE 1Q

Antibody A66 Variable Region amino acid sequences
$V_H$ chain of A66
(SEQ ID NO: 32)
QVQLVQSGAEVKKPGSSVKVSCKASGGPFSMTAFTWLRQAPGQGLEWMGGISPIFRTPKYAQKFQGRVTITADESTNTAN

MELTSLKSEDTAVYYCARTLSSYQPNNDAFAIWGQGTMVTVSS

TABLE 1Q-continued

V_K chain of A66

(SEQ ID NO: 34)
EIVLTQSPATLSLSPGERATLSCRASQSVSSYLAWYQQKPGQAPRLLIYDASNRATGIPARFSGSGSGTDFTLTISRLEP

EDFAVYFCQQYGSSPQFGQGTRLEIK

TABLE 1R

Antibody E88 Variable Region nucleic acid sequences
V_H chain of E88

(SEQ ID NO: 40)
CAGGTGCAGCTGGTGCAGTCTGGGGCTGAAGTGAAGAAGCCTGGCTCCTCGGTGAAGGTTTCCTGCAAGGCTTCTGGAGG

CCCCTTCAGCATGACTGCTTTCACCTGGCTGCGACAGGCCCCTGGACAAGGGCTTGAGTGGATGGGTGGGATCAGCCCTA

TCTTTCGTACACCGAAGTACGCACAGAAGTTCCAGGGCAGAGTCACGATTACCGCGGACGAATCCACGAACACAGCCAAC

ATGGAGCTGACCAGCCTGAAATCTGAGGACACGGCCGTGTATTACTGTGCGAGAACCCTTTCCTCCTACCAACCGAATAA

TGATGCTTTTGCTATCTGGGGCCAAGGGACAATGGTCACCGTCTCTTCA

V_L chain of E88

(SEQ ID NO: 42)
CTGCCTGTGCTGACTCAGCCACCCTCAGCGTCTGGGACCCCCGGGCAGAGGGTCACCATCTCTTGTTCTGGAAGCAGCTC

CAACATCGGAAGTAATACTGTAAACTGGTACCAGCAGCTCCCAGGAACGGCCCCCAAACTCCTCATCTATAGTAATAATC

AGCGGCCCTCAGGGGTCCCTGACCGATTCTCTGGCTCCAGGTCAGGCACCTCAGCCTCCCTGGCCATCATTGGACTCCGG

CCTGAGGATGAAGCTGATTATTACTGTCAGTCGTATGACAGCAGGCTCAGTGCTTCTCTCTTCGGAACTGGGACCACGGT

CACCGTCCTC

TABLE 1S

Antibody E88 Variable Region amino acid sequences
V_H chain of E88

(SEQ ID NO: 36)
QVQLVQSGAEVKKPGSSVKVSCKASGGPFSMTAFTWLRQAPGQGLEWMGGISPIFRTPKYAQKFQGRVTITADESTNTAN

MELTSLKSEDTAVYYCARTLSSYQPNNDAFAIWGQGTMVTVSS

V_L chain of E88

(SEQ ID NO: 38)
LPVLTQPPSASGTPGQRVTISCSGSSSNIGSNTVNWYQQLPGTAPKLLIYSNNQRPSGVPDRFSGSRSGTSASLAIIGLR

PEDEADYYCQSYDSRLSASLFGTGTTVTVL

Figure 3:
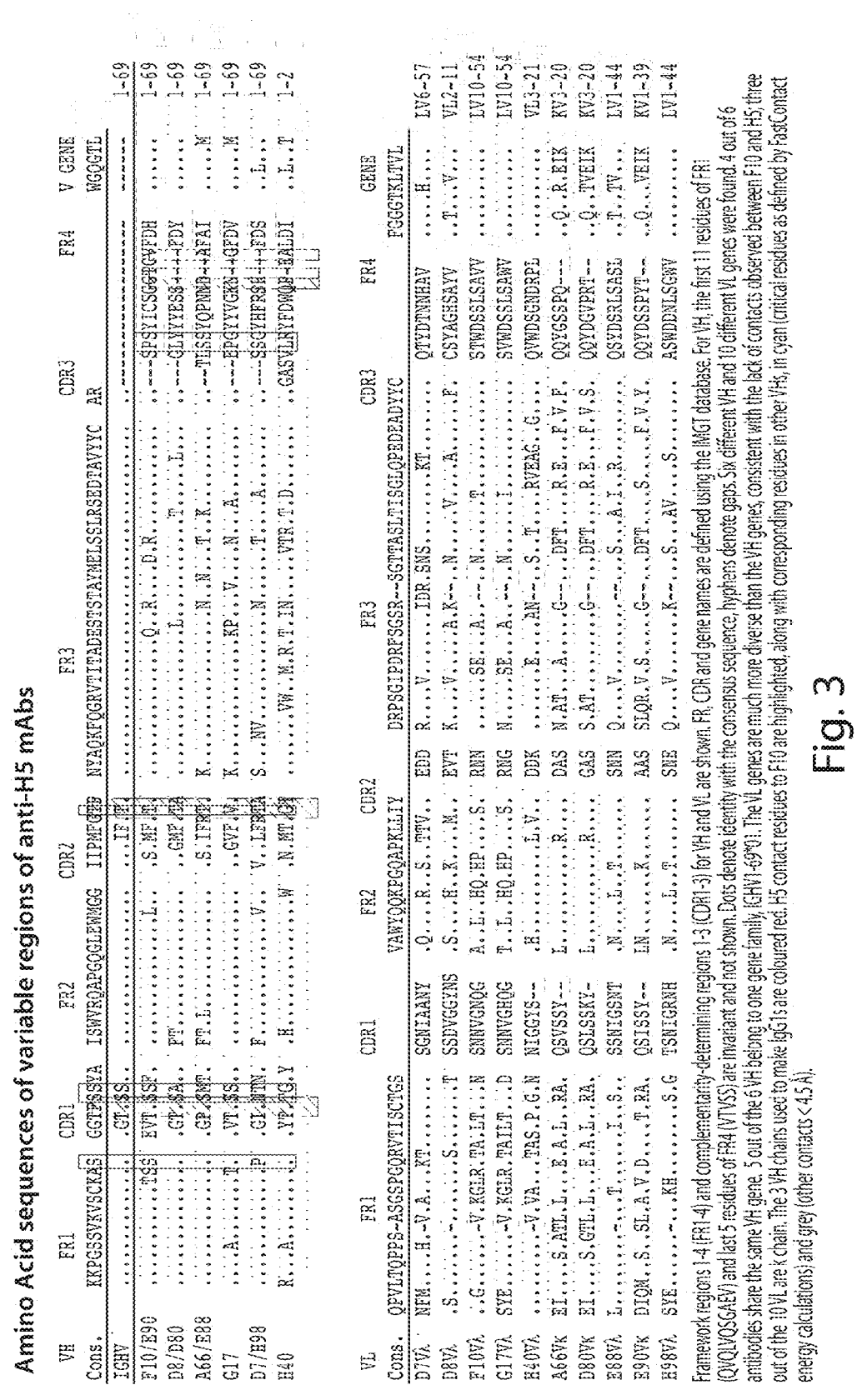

The amino acid sequences of the heavy and light chain complementarity determining regions of the neutralizing influenza antibodies are shown in Table 2 below and FIG. 3.

TABLE 2

| Antibody | CDR1 | CDR2 | CDR3 |
|---|---|---|---|
| CONSENSUS | SYAFS (SEQ ID NO: 43) | GIIPMFGTPNYAQKFQG (SEQ ID NO: 51) | SSGYYYG GGFDV (SEQ ID NO: 59) |
| D7/H98VH | TNAFS (SEQ ID NO: 44) | GVIPLFRTASYAQNVQG (SEQ ID NO: 52) | SSGYHFGRSHFDS (SEQ ID NO: 60) |
| D8/D80VH | AYAFT (SEQ ID NO: 45) | GIIGMFGTANYAQKFQG (SEQ ID NO: 53) | GLYYYESSLDY (SEQ ID NO: 61) |
| F10/90VH | SFAIS (SEQ ID NO: 46) | GISPMFGTPNYAQKFQG (SEQ ID NO: 54) | SPSYICSGGTCVFDH (SEQ ID NO: 62) |

TABLE 2-continued

| Antibody | CDR1 | CDR2 | CDR3 |
|---|---|---|---|
| G17VH | SYAIS (SEQ ID NO: 47) | GIIGVFGVPKYAQKFQG (SEQ ID NO: 55) | EPGYYVGKNGFDV (SEQ ID NO: 63) |
| H40VH | GYYIH (SEQ ID NO: 48) | WINPMTGGTNYAQKFQV (SEQ ID NO: 56) | GASVLRYFDWQPEALDI (SEQ ID NO: 64) |
| A66VH | MTAFT (SEQ ID NO: 49) | GISPIFRTPKYAQKFQG (SEQ ID NO: 57) | TLSSYQPNNDAFAI (SEQ ID NO: 65) |
| 2AVH | DNAIS (SEQ ID NO: 50) | GIIPIFGKPNYAQKFQG (SEQ ID NO: 58) | DSDAYYYGSGGMDV (SEQ ID NO: 66) |
| CONSENSUS | TGSSSNIGNYVA (SEQ ID NO: 67) | SNSDRPS (SEQ ID NO: 79) | QSYDSLSAYV (SEQ ID NO: 91) |
| D7VL | TGSSSNIAANYVQ (SEQ ID NO: 68) | EDDRRPS (SEQ ID NO: 80) | QSYDTNNHAV (SEQ ID NO: 92) |
| DD8VL | TGTSSDVGGYNSVS (SEQ ID NO: 69) | EVTKRPS (SEQ ID NO: 81) | CSYAGHSAYV (SEQ ID NO: 93) |
| F10VL | TGNSNNVGNQGAA (SEQ ID NO: 70) | RNNDRPS (SEQ ID NO: 82) | STWDSSLSAVV (SEQ ID NO: 94) |
| G17VH | TGDSNNVGHQGTA (SEQ ID NO: 71) | RNGNRPS (SEQ ID NO: 83) | SVWDSSLSAWV (SEQ ID NO: 95) |
| H40VH | GGNNIGGYSVH (SEQ ID NO: 72) | DDKDRPS (SEQ ID NO: 84) | QVWDSGNDRPL (SEQ ID NO: 96) |
| A66VH | RASQSVSSYLA (SEQ ID NO: 73) | DASNRAT (SEQ ID NO: 85) | QQYGSSPQV (SEQ ID NO: 97) |
| D80VL | RASQSLSSKYLA (SEQ ID NO: 74) | GASSRAT (SEQ ID NO: 86) | QQYDGVPRT (SEQ ID NO: 98) |
| E88VL | TGSSSNIGNYVA (SEQ ID NO: 75) | SNNQRPS (SEQ ID NO: 87) | QSYDSRLSASL (SEQ ID NO: 99) |
| E90VK | SGSSSNIGSNTVN (SEQ ID NO: 76) | AASSLQR (SEQ ID NO: 88) | QQYDSSPYT (SEQ ID NO: 100) |
| H98VL | RASQSISSYLN (SEQ ID NO: 77) | SNEQRPS (SEQ ID NO: 89) | ASWDDNLSGWV (SEQ ID NO: 101) |
| 2AVL | TLSSGHSNYIIA (SEQ ID NO: 78) | VNSDGSHTKGD (SEQ ID NO: 90) | ETWDTKIHV (SEQ ID NO: 102) |

Those skilled in the art will recognize that additional scFvs and monoclonal antibodies having different binding affinities may also be therapeutically effective. For example, antibodies and scFvs having binding affinities ranging from about 1 pM to about 200 mM may also be therapeutically effective.

Neutralization of H5N1 with Anti-Influenza Antibodies.

Figure 4B:
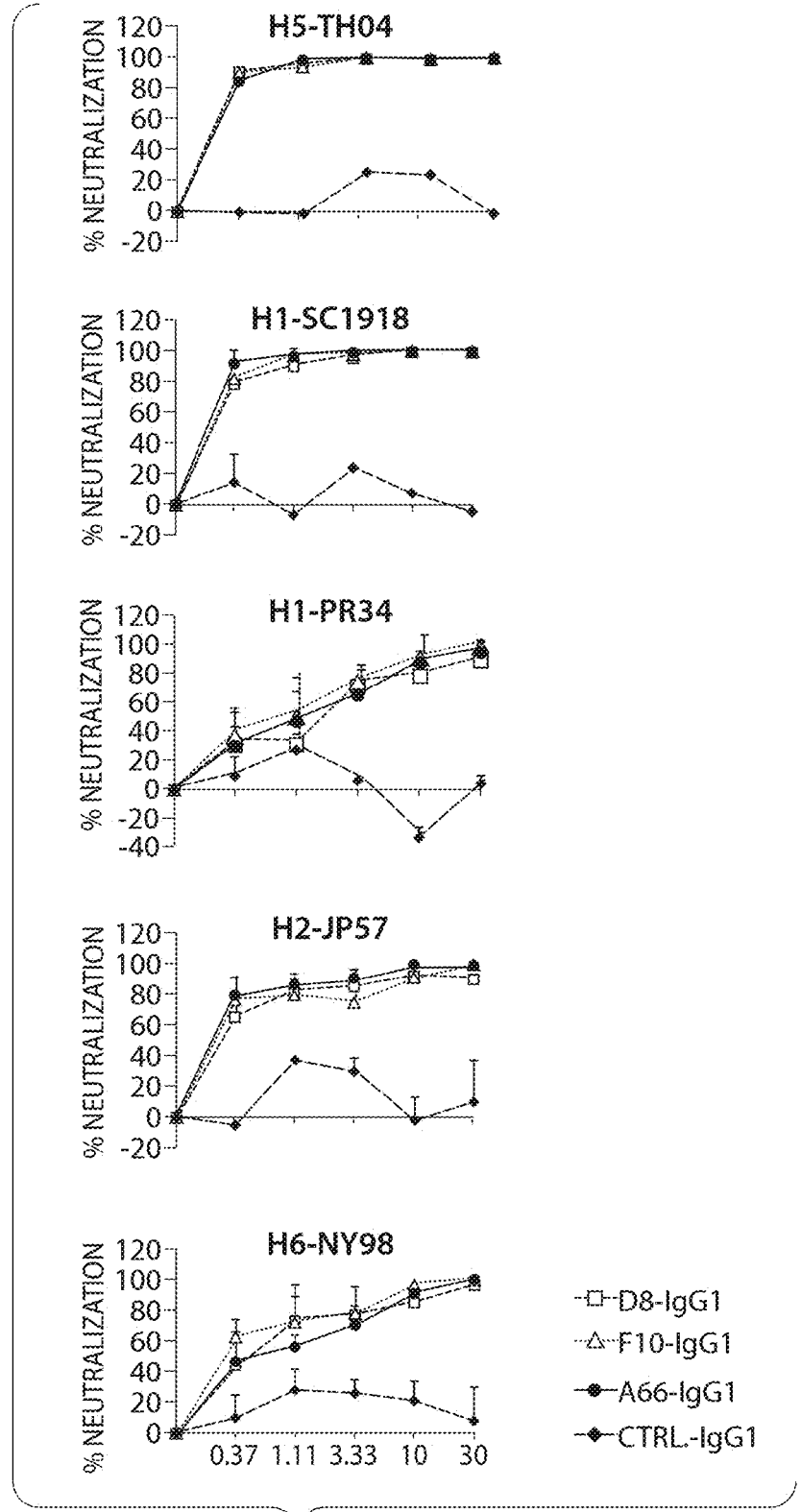

H-5 pseudotyped viruses were incubated with bivalent scFv and full length antibodies and the antibody-virus mixture was contacted with 293T cells. Infectivity was quantified by measuring luciferase activity in the target cells. The D7, D8, F10, G17, H40, A66, D80, E88, E90, and H98, antibodies have potent neutralization activity against H5. D8, F10 and A66 antibodies also crossed neutralized H1N1, potently neutralized strain H1-SC/1918 and moderately neutralized strain H1-PR-34 (FIGS. 4A and 4B).

Characterization of the 8, 10 and 66 Epitope.

Primary epitope mapping of 8, 10 and 66 binding to the influenza hemagglutinin (HA) protein showed that epitopes of these three antibodies were similar and are located at positions 307 on HA1 and at positions 52, 59, 65, and 93 on HA2. This epitope is comprised of the hemagglutinin protein which is not shed by the virus. This is unlike most other known ant-influenza antibodies which bind the neuraminidase protein which is shed by the virus.

Structural Characterization of the nAb Epitope

The epitope and mode of binding of one of the nAbs, F10, by solving the crystal structure of its scFv fragment in complex with HA (H5-VN04) at 3.2 Å resolution, and by mutagenesis. (FIG. 6 and Table 4)

In the complex, each H5 trimer binds three molecules of F10, at symmetry-related sites, burying ~1500 Å$^2$ of protein surface per antibody; the structure of H5 itself is not significantly altered by F10 binding. HA is synthesized as a single chain, HA0, that is activated by proteolytic cleavage into two subunits, HA1 and HA2. Cleavage leads to the burial of the "fusion peptide" (comprising the first ~21 residues of HA2) into the membrane-proximal stem. F10 binding occurs exclusively in this region (FIG. 6), making intimate contacts with the fusion peptide, elements of HA1 and HA2 (both of which are integral to the structure of this region) that lock the peptide into place in the neutral pH conformation, as well as the large helical hairpin of HA2 that undergoes a massive conformation change at acidic pH in order to propel the fusion peptide from its viral membrane-proximal pocket to the distal surface of the virus, where it can trigger fusion with the endosomal membrane.

The heavy chain of F10 plays the major role in H5 binding, utilizing the tips of its three complementarity-determining regions (CDRs). Each F10 molecule make contacts with both the HA1 and HA2 subunits within a single monomer of the HA trimer (FIG. 6). The contact region comprises a pocket formed by part of the HA2 fusion peptide, with elements of HA1 on one side and an exposed face of helix αA of HA2 on the other (FIGS. 4 and 6). A triad of antibody residues—F55 and M54 from CDR H2, and Y102 from CDR H3—form major contact points. The phenyl ring of F55 lies across a flat surface formed by a prominent loop of the fusion peptide loop (HA2 residues DGW $19_2$-$21_2$ (H3 numbering scheme; subscripts 1 and 2 refer to HA1 and HA2 chains)) and the aromatic side-chains of two flanking histidines (residues $18_1$ and $38_1$) and a tryptophan, $W21_2$, which forms the back of the pocket. The side-chain of M54 also contacts the aromatic rings of $W21_2$ and $H38_1$, as well as the side-chain of $I45_2$ from helix αA, while its main-chain carbonyl oxygen hydrogen-bonds with the side-chain of $H38_1$. Y102 inserts its side-chain into a hydrophobic crevice created by four side-chains of the αA helix, and also hydrogen-bonds to a backbone carbonyl ($D19_2$) of the fusion peptide. The CDR H1 loop makes multiple contacts with the C-terminal end of helix αA and a loop of HA1 at the base of the head region (FIGS. 6B and 6C).

In parallel, mutagenesis experiments were carried out on helix αA to help define the epitope (FIG. 6). Mutations in 3 residues that directly contact the antibody: V52A/E, N53A and I56A, significantly reduced or ablated antibody binding, while the conservative mutation, V52L, had no effect. As controls, mutations on a different exposed face of the helix, which does not contact the antibody, had no effect on antibody binding (FIG. 6A-6D). Thus, mutagenesis of the αA helix is fully consistent with the epitope defined crystallographically for F10. Furthermore, the other two nAbs, for which no structural data exist, showed an almost identical mutant-nAb binding profile, indicative of a closely overlapping epitope and consistent with competitive binding (FIG. 6, FIG. 9). Taken together, we conclude that all three nAbs neutralize virus by stabilizing the neutral pH conformation of HA in a region that provides the trigger (most likely release of the fusion peptide from its pocket) for conformational changes that lead to the fusogenic state.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked $V_H$::$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." CDRs for the VH and VL regions of the disclosed antibodies are shown in FIG. 3 respectively.

As used herein, the term "epitope" includes any protein determinant capable of specific binding to an immunoglobulin, an scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a influenza epitope when the equilibrium binding constant ($K_d$) is ≤1 pM, preferably 100 nM, more preferably ≤10 nM, and most preferably ≤100 pM to about 1 pM, as measured by assays such as radioligand binding assays or similar assays known to those skilled in the art.

A influenza protein (e.g., HA or neuramindase) of the invention, or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to the HA protein of the influenza virus. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the influenza HA protein, with which it is normally reactive, and then add the human monoclonal antibody being tested to determine if the human monoclonal antibody being tested is inhibited in its ability to bind the HA protein. If the human monoclonal antibody being tested is inhibited then, in all likelihood, it has the same, or functionally equivalent, epitopic specificity as the monoclonal antibody of the invention. Screening of human monoclonal antibodies of the invention, can be also carried out by utilizing the influenza virus and determining whether the test monoclonal antibody is able to neutralize the influenza virus.

Various procedures known within the art may be used for the production of polyclonal or monoclonal antibodies directed against a protein of the invention, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103) Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet. 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of an influenza virus in a sample. The antibody can also be used to try to bind to and disrupt influenza virus cell membrane fusion.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab'2)}$ fragment produced by pepsin digestion of an antibody molecule; (ii) an $F_{ab}$ fragment generated by reducing the disulfide bridges of an $F_{(ab'2)}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating influenza. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$ and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl)carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio)propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS(N-hydroxy-sulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against Influenza Virus

Methods for the screening of antibodies that possess the desired specificity include, but are not limited to, enzyme linked immunosorbent assay (ELISA) and other immunologically mediated techniques known within the art.

Antibodies directed against a influenza virus protein such as HA (or a fragment thereof) may be used in methods known within the art relating to the localization and/or quantitation of a influenza virus protein (e.g., for use in measuring levels of the influenza virus protein within appropriate physiological samples, for use in diagnostic methods, for use in imaging the protein, and the like). In a given embodiment, antibodies specific to an influenza virus protein, or derivative, fragment, analog or homolog thereof, that contain the antibody derived antigen binding domain, are utilized as pharmacologically active compounds (referred to hereinafter as "Therapeutics").

An antibody specific for an influenza virus protein of the invention can be used to isolate an influenza virus polypeptide by standard techniques, such as immunoaffinity, chromatography or immunoprecipitation. Antibodies directed against an influenza virus protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention, including polyclonal, monoclonal, humanized and fully human antibodies, may used as therapeutic agents. Such agents will generally be employed to treat or prevent an influenza virus-related disease or pathology (e.g., bird flu) in a subject. An antibody preparation, preferably one having high specificity and high affinity for its target antigen, is administered to the subject and will generally have an effect due to its binding with the target. Administration of the antibody may abrogate or inhibit or interfere with the internalization of the virus into a cell In this case, the antibody binds to the target and masks a binding site of the naturally occurring ligand, thereby blocking fusion the virus to the cell membrane inhibiting internalization of the virus.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding an influenza virus protein or a fragment thereof of the invention, as well as other molecules identified by the screening assays disclosed herein, can be administered for the treatment of an influenza virus-related disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of an influenza virus (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the fusion of an influenza virus to the cell membrane. Also provided are methods of identifying compounds useful to treat influenza infection. The invention also encompasses compounds identified using the screening assays described herein.

For example, the invention provides assays for screening candidate or test compounds which modulate the interaction between the influenza virus and the cell membrane. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409.).

In one embodiment, a candidate compound is introduced to an antibody-antigen complex and determining whether the candidate compound disrupts the antibody-antigen complex, wherein a disruption of this complex indicates that the candidate compound modulates the interaction between an influenza virus and the cell membrane. For example, the antibody may be monoclonal antibody D7, D8, F10, G17, H40, A66, D80, E88, E90, and H98 and the antigen may be located on the HA protein of an influenza virus.

In another embodiment, at least one HA protein is provided, which is exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat a an influenza virus-related disease or disorder, e.g. bird flu. For example, the at least one influenza virus protein may be provided as an influenza virus molecule.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a an influenza virus neutralizing antibody, such as monoclonal antibody D7, D8, F10, G17, H40, A66, D80, E88, E90, and H98. Additionally, the antigen may be a HA protein, or a portion thereof. In any of the assays described herein, the ability of a candidate compound to interfere with the binding between the D7, D8, F10, G17, H40, A66, D80, E88, E90, and H98 monoclonal antibody and the HA protein indicates that the candidate compound will be able to interfere with or modulate the fusion of the influenza virus and the cell membrane Moreover, because the binding of the HA protein to cell is responsible for influenza virus entry into cells such candidate compounds will also be useful in the treatment of a influenza virus related disease or disorder, e.g. bird flu.

The screening methods disclosed herein may be performed as a cell-based assay or as a cell-free assay. The cell-free assays of the invention are amenable to use of both the soluble form or the membrane-bound form of the HA proteins and fragments thereof. In the case of cell-free assays comprising the membrane-bound forms of the HA proteins, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody or the antigen (e.g. the can be immobilized utilizing conjugation of biotin and streptavidin. Biotinylated antibody or antigen molecules can be prepared from biotin-NHS(N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, a an assay can be performed in which a influenza protein (e.g., HA1, HA 2 or neurominidase) or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide is subsequently incubated with a second, labeled antibody or antibody bound to a coupling agent such as biotin or avidin. This second antibody may be another anti-influenza antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

An exemplary method for detecting the presence or absence of a influenza virus (in a biological sample involves obtaining a biological sample from a test subject and contacting the biological sample with a labeled monoclonal or scFv antibody according to the invention such that the presence of the influenza virus is detected in the biological sample.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect an influenza virus in a biological sample in vitro as well as in vivo. For example, in vitro techniques for detection of an influenza virus include enzyme linked immunosorbent assays (ELISAs), Western blots, immunoprecipitations, and immunofluorescence. Furthermore, in vivo techniques for detection of an influenza virus include introducing into a subject a labeled anti-influenza virus antibody. For example, the antibody can be labeled with a radioactive marker whose presence and location in a subject can be detected by standard imaging techniques.

In one embodiment, the biological sample contains protein molecules from the test subject. One preferred biological sample is a peripheral blood leukocyte sample isolated by conventional means from a subject.

The invention also encompasses kits for detecting the presence of an influenza virus in a biological sample. For example, the kit can comprise: a labeled compound or agent capable of detecting an influenza virus (e.g., an anti-influenza scFv or monoclonal antibody) in a biological sample; means for determining the amount of an influenza virus in the sample; and means for comparing the amount of an influenza virus in the sample with a standard. The compound or agent can be packaged in a suitable container. The kit can further comprise instructions for using the kit to detect an influenza virus in a sample.

Passive Immunization

Passive immunization has proven to be an effective and safe strategy for the prevention and treatment of viral diseases. (See Keller et al., Clin. Microbiol. Rev. 13:602-14

(2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using neutralizing human monoclonal antibodies could provide an immediate treatment strategy for emergency prophylaxis and treatment of influenza such as bird flu while the alternative and more time-consuming development of vaccines and new drugs in underway.

Subunit vaccines potentially offer significant advantages over conventional immunogens. They avoid the safety hazards inherent in production, distribution, and delivery of conventional killed or attenuated whole-pathogen vaccines. Furthermore, they can be rationally designed to include only confirmed protective epitopes, thereby avoiding suppressive T epitopes (see Steward et al., J. Virol. 69:7668 (1995)) or immunodominant B epitopes that subvert the immune system by inducing futile, non-protective responses (e.g. "decoy" epitopes). (See Garrity et al., J. Immunol. 159:279 (1997)).

Moreover, those skilled in the art will recognize that good correlation exists between the antibody neutralizing activity in vitro and the protection in vivo for many different viruses, challenge routes, and animal models. (See Burton, Natl. Rev. Immunol. 2:706-13 (2002); Parren et al., Adv. Immunol. 77:195-262 (2001)). The data presented herein demonstrate that the D7, D8, F10, G17, H40, A66, D80, E88, E90, and H98 human monoclonal antibodies can be further developed and tested in in vivo animal studies to determine its clinical utility as a potent viral entry inhibitor for emergency prophylaxis and treatment of influenza.

Antigen-Ig Chimeras in Vaccination

It has been over a decade since the first antibodies were used as scaffolds for the efficient presentation of antigenic determinants to the immune systems. (See Zanetti, Nature 355:476-77 (1992); Zaghouani et al., Proc. Natl. Acad. Sci. USA 92:631-35 (1995)). When a peptide is included as an integral part of an IgG molecule (e.g., the 11A or 256 IgG1 monoclonal antibody described herein), the antigenicity and immunogenicity of the peptide epitopes are greatly enhanced as compared to the free peptide. Such enhancement is possibly due to the antigen-IgG chimeras longer half-life, better presentation and constrained conformation, which mimic their native structures.

Moreover, an added advantage of using an antigen-Ig chimera is that either the variable or the Fc region of the antigen-Ig chimera can be used for targeting professional antigen-presenting cells (APCs). To date, recombinant Igs have been generated in which the complementarity-determining regions (CDRs) of the heavy chain variable gene ($V_H$) are replaced with various antigenic peptides recognized by B or T cells. Such antigen-Ig chimeras have been used to induce both humoral and cellular immune responses. (See Bona et al., Immunol. Today 19:126-33 (1998)).

Chimeras with specific epitopes engrafted into the CDR3 loop have been used to induce humoral responses to either HIV-1 gp120 V3-loop or the first extracellular domain (D1) of human CD4 receptor. (See Lanza et al., Proc. Natl. Acad. Sci. USA 90:11683-87 (1993); Zaghouani et al., Proc. Natl. Acad. Sci. USA 92:631-35 (1995)). The immune sera were able to prevent infection of CD4 SupT1 cells by HIV-1MN (anti-gp120 V3C) or inhibit syncytia formation (anti-CD4-D1). The CDR2 and CDR3 can be replaced with peptide epitopes simultaneously, and the length of peptide inserted can be up to 19 amino acids long.

Alternatively, one group has developed a "troybody" strategy in which peptide antigens are presented in the loops of the Ig constant (C) region and the variable region of the chimera can be used to target IgD on the surface of B-cells or MHC class II molecules on professional APCs including B-cells, dendritic cells (DC) and macrophages. (See Lunde et al., Biochem. Soc. Trans. 30:500-6 (2002)).

An antigen-Ig chimera can also be made by directly fusing the antigen with the Fc portion of an IgG molecule. You et al., Cancer Res. 61:3704-11 (2001) were able to obtain all arms of specific immune response, including very high levels of antibodies to hepatitis B virus core antigen using this method.

DNA Vaccination

DNA vaccines are stable, can provide the antigen an opportunity to be naturally processed, and can induce a longer-lasting response. Although a very attractive immunization strategy, DNA vaccines often have very limited potency to induce immune responses. Poor uptake of injected DNA by professional APCs, such as dendritic cells (DCs), may be the main cause of such limitation. Combined with the antigen-Ig chimera vaccines, a promising new DNA vaccine strategy based on the enhancement of APC antigen presentation has been reported (see Casares, et al., Viral Immunol. 10:129-36 (1997); Gerloni et al., Nat. Biotech. 15:876-81 (1997); Gerloni et al., DNA Cell Biol. 16:611-25 (1997); You et al., Cancer Res. 61:3704-11 (2001)), which takes advantage of the presence of Fc receptors (FcγRs) on the surface of DCs.

It is possible to generate a DNA vaccine encoding an antigen (Ag)-Ig chimera. Upon immunization, Ag-Ig fusion proteins will be expressed and secreted by the cells taking up the DNA molecules. The secreted Ag-Ig fusion proteins, while inducing B-cell responses, can be captured and internalized by interaction of the Fc fragment with FcγRs on DC surface, which will promote efficient antigen presentation and greatly enhance antigen-specific immune responses. Applying the same principle, DNA encoding antigen-Ig chimeras carrying a functional anti-MHC II specific scFv region gene can also target the immunogens to all three types of APCs. The immune responses could be further boosted with use of the same protein antigens generated in vitro (i.e., "prime and boost"), if necessary. Using this strategy, specific cellular and humoral immune responses against infection of influenza virus were accomplished through intramuscular (i.m.) injection of a DNA vaccine. (See Casares et al., Viral. Immunol. 10:129-36 (1997)).

Vaccine Compositions

Therapeutic or prophylactic compositions are provided herein, which generally comprise mixtures of one or more monoclonal antibodies or ScFvs and combinations thereof. The prophylactic vaccines can be used to prevent an influenza virus infection and the therapeutic vaccines can be used to treat individuals following an influenza virus infection. Prophylactic uses include the provision of increased antibody titer to an influenza virus in a vaccination subject. In this manner, subjects at high risk of contracting influenza can be provided with passive immunity to an influenza virus These vaccine compositions can be administered in conjunction with ancillary immunoregulatory agents. For example, cytokines, lymphokines, and chemokines, including, but not limited to, IL-2, modified IL-2 (Cys125→Ser125), GM-CSF, IL-12, γ-interferon, IP-10, MIP1β, and RANTES.

Methods of Immunization

The vaccines of the present invention have superior immunoprotective and immunotherapeutic properties over other anti-viral vaccines The invention provides a method of immunization, e.g., inducing an immune response, of a subject. A subject is immunized by administration to the subject a composition containing a membrane fusion protein of a pathogenic enveloped virus. The fusion protein is coated or embedded in a biologically compatible matrix.

The fusion protein is glycosylated, e.g. contains a carbohydrate moiety. The carbohydrate moiety may be in the form of a monosaccharide, disaccharide(s). oligosaccharide(s), polysaccharide(s), or their derivatives (e.g. sulfo- or phospho-substituted). The carbohydrate is linear or branched. The carbohydrate moiety is N-linked or O-linked to a polypeptide. N-linked glycosylation is to the amide nitrogen of asparagine side chains and O-linked glycosylation is to the hydroxy oxygen of serine and threonine side chains.

The carbohydrate moiety is endogenous to the subject being vaccinated. Alternatively, the carbohydrate moiety is exogenous to the subject being vaccinated. The carbohydrate moiety are carbohydrate moieties that are not typically expressed on polypeptides of the subject being vaccinated. For example, the carbohydrate moieties are plant-specific carbohydrates. Plant specific carbohydrate moieties include for example N-linked glycan having a core bound $\alpha 1,3$ fucose or a core bound $\beta 1,2$ xylose. Alternatively, the carbohydrate moiety are carbohydrate moieties that are expressed on polypeptides or lipids of the subject being vaccinate. For example many host cells have been genetically engineered to produce human proteins with human-like sugar attachments.

For example, the fusion protein is a trimeric hemagglutinin protein. Optionally, the hemagglutinin protein is produced in a non-mammalian cell such as a plant cell. The subject is at risk of developing or suffering from a viral infection. Enveloped viruses include for example, epstein-barr virus, herpes simplex virus, type 1 and 2, human cytomegalovirus, human herpesvirus, type 8, varicella zoster virus, hepatitis B virus, hepatitis C virus, human immunodeficiency virus, influenza virus, measles virus, mumps virus, parainfluenza virus, respiratory syncytial virus, rabies virus, and rubella virus The methods described herein lead to a reduction in the severity or the alleviation of one or more symptoms of a viral infection. Infections are diagnosed and or monitored, typically by a physician using standard methodologies A subject requiring immunization is identified by methods know in the art. For example subjects are immunized as outlined in the CDC's General Recommendation on Immunization (51(RR02) pp 1-36) Cancer is diagnosed for example by physical exam, biopsy, blood test, or x-ray.

The subject is e.g., any mammal, e.g., a human, a primate, mouse, rat, dog, cat, cow, horse, pig, a fish or a bird. The treatment is administered prior to diagnosis of the infection. Alternatively, treatment is administered after diagnosis.

Efficaciousness of treatment is determined in association with any known method for diagnosing or treating the particular disorder or infection. Alleviation of one or more symptoms of the disorder indicates that the compound confers a clinical benefit.

Evaluation of Antigenic Protein Fragments (APFs) for Vaccine Potential

A vaccine candidate targeting humoral immunity must fulfill at least three criteria to be successful: it must provoke a strong antibody response ("immunogenicity"); a significant fraction of the antibodies it provokes must cross-react with the pathogen ("immunogenic fitness"); and the antibodies it provokes must be protective. While immunogenicity can often be enhanced using adjuvants or carriers, immunogenic fitness and the ability to induce protection (as evidenced by neutralization) are intrinsic properties of an antigen which will ultimately determine the success of that antigen as a vaccine component.

Evaluation of Immunogenic Fitness

"Immunogenic fitness" is defined as the fraction of antibodies induced by an antigen that cross-react with the pathogen. (See Matthews et al., J. Immunol. 169:837 (2002)). It is distinct from immunogenicity, which is gauged by the titer of all of the antibodies induced by an antigen, including those antibodies that do not cross-react with the pathogen. Inadequate immunogenic fitness has probably contributed to the disappointing track record of peptide vaccines to date. Peptides that bind with high affinity to antibodies and provoke high antibody titers frequently lack adequate immunogenic fitness, and, therefore, they fail as potential vaccine components. Therefore, it is important to include immunogenic fitness as one of the criteria for selecting influenza vaccine candidates.

A common explanation for poor immunogenic fitness is the conformational flexibility of most short peptides. Specifically, a flexible peptide may bind well to antibodies from patients, and elicit substantial antibody titers in naïve subjects. However, if the peptide has a large repertoire of conformations, a preponderance of the antibodies it induces in naïve subjects may fail to cross-react with the corresponding native epitope on intact pathogen.

Like short peptides, some APFs may be highly flexible and, therefore may fail as vaccine components. The most immunogenically fit APFs are likely to consist of self-folding protein subdomains that are intrinsically constrained outside the context of the whole protein.

Because immunogenic fitness is primarily a property of the APF itself, and not of the responding immune system, immunogenic fitness can be evaluated in an animal model (e.g. in mice) even though ultimately the APF will have to perform in humans.

The immunogenic fitness achieved by APFs is evaluated by immunosorption of anti-APF sera with purified spike or membrane protein, in a procedure analogous to that described in Matthews et al., J. Immunol. 169:837 (2002). IgG is purified from sera collected from mice that have been immunized. Purified, biotinylated proteins (as appropriate, depending on the particular APF with which the mice were immunized) are mixed with the mouse IgG and incubated. Streptavidin-coated sepharose beads are then added in sufficient quantity to capture all of the biotinylated protein, along with any bound IgG. The streptavidin-coated beads are removed by centrifugation at 13,000 rpm in a microcentrifuge, leaving IgG that has been depleted of antibodies directed against the protein, respectively. Mock immunoabsorptions are performed in parallel in the same way, except that biotinylated BSA will be substituted for influenza protein as a mock absorbent.

To measure the immunogenic fitness of APFs, the absorbed antibodies and the mock-absorbed antibodies are titered side-by-side in ELISA against the immunizing APF. For APFs affinity selected from a phage display NPL, the antigen for these ELISAs will be purified APF-GST fusion proteins. For the potentially glycosylated APFs from the mammalian cell display NPL, the antigen for these ELISAs will be APF-Fc fusion proteins secreted by mammalian cells and purified with protein A. The percentage decrease in the anti-APF titer of absorbed antibodies compared with the mock-absorbed antibodies will provide a measure of the immunogenic fitness of the APF.

Methods of Treatment

The invention provides for both prophylactic and therapeutic methods of treating a subject at risk of (or susceptible to) an influenza virus-related disease or disorder. Such diseases or disorders include but are not limited to, e.g., bird flu.

Prophylactic Methods

In one aspect, the invention provides methods for preventing an influenza virus-related disease or disorder in a subject by administering to the subject a monoclonal antibody or scFv antibody of the invention or an agent identified according to the methods of the invention. For example, scFv and/or monoclonal antibody D7, D8, F10, G17, H40, A66, D80, E88, E90, and H98 may be administered in therapeutically effective amounts. Optionally, two or more anti-influenza antibodies are co-administered Subjects at risk for an influenza virus-related diseases or disorders include patients who have come into contact with an infected person or who have been exposed to the influenza virus in some other way. Administration of a prophylactic agent can occur prior to the manifestation of symptoms characteristic of the influenza virus-related disease or disorder, such that a disease or disorder is prevented or, alternatively, delayed in its progression.

The appropriate agent can be determined based on screening assays described herein. Alternatively, or in addition, the agent to be administered is a scFv or monoclonal antibody that neutralizes an influenza virus that has been identified according to the methods of the invention.

Therapeutic Methods

Another aspect of the invention pertains to methods of treating an influenza virus-related disease or disorder in a patient. In one embodiment, the method involves administering an agent (e.g., an agent identified by a screening assay described herein and/or an scFv antibody or monoclonal antibody identified according to the methods of the invention), or combination of agents that neutralize the influenza to a patient suffering from the disease or disorder.

Combinatory Methods

The invention provides treating an influenza-related disease or disorder, such as bird flu, in a patient by administering two or more antibodies, such as D7, D8, F10, G17, H40, A66, D80, E88, E90, and H98 that bind to the same epitope of the HA protein.

The invention will be further described in the following examples, which do not limit the scope of the invention described in the claims.

EXAMPLES

Example 1: General Methods

Expression and Preparation of Various Panning Antigens for Selection of Phage Display Antibody Library.

HA 1.

HA 1 is the N-terminal fragment (aa17-338) of (A/Thailand/2 (SP-33)/2004 (H5N1). The gene was codon-optimized and expressed as fusion protein with a C-terminal 9 amino-acids tag (C9-tag: GTETSQVAPA (SEQ ID NO: 103)). The fusion protein HA1-C9 was expressed in 293T cells transiently and the secreted protein was purified from supernatant by affinity chromatography. Protein A Sepharose covalently coupled with anti-C9 antibody 1D4 (National Cell Culture Center) was used for purification of HA1-C9.

Trimeric HA0.

The ectodomain (HA0) of hamagglutinin (HA) gene of A/Viet Nam/1203/2004 was expressed in insect cells as a fusion protein by adapting the protocol described previously[33]. This construct contains a C-terminal trimerizing 'foldon' sequence from the bacteriophage T4 fibritin to stabilize the trimeric structure, followed by a thrombin site and a His6 tag. The cDNA of the fusion protein was cloned into the baculovirus transfer vector, pAcGP67A (BD Biosciences, Bedford, Mass.) to allow for efficient secretion of recombinant protein. $9 \times 10^6$ cells were infected with the viral stock. 3 days after infection, the cells were spun down and the supernatant was incubated with 6 ml Ni-NTA beads (Qiagen Inc., Valencia, Calif.). The beads were washed with TBS buffer (10 mM Tris.HCl/80 mM NaCl, pH8.0) with 10 mM imidazole and eluted with TBS with 250 mM Imidazole. The eluted HAS protein was dialyzed against TBS buffer and further purified by ion-exchange using Mono Q HR10/10 column (GE Healthcare, Piscataway, N.J.). The purified HAS were digested by thrombin overnight. The integrity and property of HA0 trimer was examined using Gel filtration (Superdex 200 column) and SDS-PAGE.

Selection of Phage Antibody Libraries and Screening of Antibodies Against H5.

Two human non-immune scFv libraries (a total of $2.7 \times 10^{10}$ members) constructed from B-cells of 57 un-immunized donors were used for selection of scFvs against the purified HA1 or trimeric HA0. $5 \times 10^{11}$ pfu of phage-scFvs prepared from each library were incubated with immunotubes (Nunc, Naperville, Ill.) coated with 10 μg of HA1 or HA0, separately. The selection procedures were the same as described previously. After two rounds of selection, randomly picked single phage-scFv clones were screened for specific binding to HA1 or HA0 by enzyme-linked immunosorbent assay (ELISA) as described previously. Clones that bound to HA1 or HA0 with $A_{450}$ values of >1.0 were scored as positive, whereas negative clones gave values of <0.1. For HA1 or HA0 specific binding clones, the genes of variable regions of heavy (VH) and light (VL) chain were sequenced and their corresponding amino acid sequences were aligned to identify antibodies with different sequence for further characterization.

Expression and Purification of Soluble scFv-Fcs and Full-Length Human IgG1.

Phage-scFvs of individual clones were produced for neutralization assay using the same method as making phage library. Phage particles were concentrated 25 times by using PEG/NaCl precipitation. scFv-Fcs and whole human IgG1s were produced as described previously. In brief, selected scFvs were converted to scFv-Fcs by subcloning the scFv into a Fc expression vector pcDNA 3.1-Hinge which contains the hinge, CH2, and CH3 domains of human IgG1 but lacks CH1. For whole human IgG1s, the VH and VL gene fragments of scFv were separately subcloned into human IgG1 kappa light chain or lambda light chain expression vector TCAE5 or TCAE6. scFv-Fcs or IgG1 s were expressed in 293T or 293F cells (Invitrogen) by transient transfection and purified by protein A sepharose affinity chromatography.

Surface Plasmon Resonance (SPR) Analysis

Kinetic analyses of H5 HA Mabs binding to recombinant HA0 (VietNam1203/04) trimer were performed on a Biacore T100 (Biacore) at 25° C. Anti-human IgG Fc antibody (Biacore) was covalently coated to individual flow cell surfaces of a CM4 sensor chip by amine-coupling using the amine coupling kit (Biacore). HA Mabs were captured onto anti-human IgG Fc surfaces at the flow rate of 10 ul/min in HBS buffer (Biacore) to ensure that the Mab-HA0 binding occurred as a homogenous 1:1 Langmuir interaction. HA0 was injected over each flow cell at the flow rate of 30 ul/min in HBS buffer, and at concentrations ranging from to 0.31 to 20 nM. A buffer injection served as a negative control. All experiments contained an additional anti-human IgG Fc antibody control surface that served to account for changes in the buffer refractive index and to test for potential nonspecific interactions between HA0 and anti-human IgG Fc. Upon completion of each association and dissociation cycle, surfaces were regenerated with 3M $MgCl_2$ solution. The association rates (ka), dissociation rate constants (kd), and affinity constants (KD) were calculated using Biacore T100 evaluation software. The goodness of each fit was based on the agreement between experimental data and the calculated fits, where the $Chi^2$ values were below 1.0. Surface densities of Mabs against HA0 were optimized to minimize mass transfer and avoid any contribution of avidity effects. All ka, kd, KD reported here represent the means and standard errors of three experiments.

Viruses and Cells

Wild type influenza A/Vietnam/1203/2004 (H5N1; H5-VN04), A/HongKong/483/1997 (H5N1; H5-HK97), A/Netherlands/219/2003 (H7N7; H7-NL03), and A/Ohio/4/1983 (H1N1; H1-OH83) viruses as well as a cold-adapted vaccine strain of A/Ann Arbor/6/1960 (H2N2) were obtained from the WHO Global Influenza Surveillance Network and provided by Alexander Klimov (CDC, Atlanta, USA). H1-PR34 and Madin-Darby canine kidney (MDCK) cells were obtained from the American Type Culture Collection and propagated in Dulbecco's Modification of Eagle's Medium with 10% fetal bovine serum. Viral infectivity was determined by plaque assay on MDCK cells. Live wildtype H5N1 viruses were handled in biosafety level 3 containment, including enhancements required by the U.S. Department of Agriculture and the Select Agents program http://www.cdc.gov/od/ohs/biosfty/bmbl5/bmbl5toc.htm.

Neutralization Assay with HA Pseudotyped Viruses

Plasmids and Constructs

The full length HA gene of A/Thailand/2(SP-33)/2004 (H5N1)), H5-SP33, and neuramidase gene of A/Vietnam 1203/2004, N1, were codon-optimized and cloned into pcDNA3.1 vector to obtain the pcDNA3.1-H5-SP33 and pcDNA3.1-N1 expression plasmid, separately. The pCAGGS-H1(SC) plasmid encoding A/South Carolina/1/1918 (H1N1) full length HA protein was kindly provided by form Dr. P. Palese (Mount Sinai School of Medicine, US). The pCAGGS-H1(PR) plasmid encoding A/Puerto Rico/8/34 (H1N1) HA protein was a generous gift from Dr. M. Farzan (Harvard Medical School, US).

Making the HA-Pseudotyped Viruses.

The single-round HIV luciferase reporter viruses of H5N1 or H1N1 pseudotyped by H5-SP33, H1-SC/1918 or H1-PR/34 were made by co-transfection of 293T cells with 4 plasmids that are pcDNA3.1-H5-SP33, HIV packaging vector pCMVΔR 8.2 encoding HIV-1 Gag-Pol[57], transfer vector pHIV-Luc encoding the firefly luciferase reporter gene under control of the HIV-1 LTR, and expressing plasmid pcDNA3.1-N1. 36 hours post-transfection, viral supernatants were harvested and stored at 4° C.

Neutralization Assay.

Before transducing cells, viral supernatant of H1-SC/1918 or H1-PR/34F pseudotyped viruses was incubated with 16 μg/mL TPCK-treated trpsin for one hour at 25° C. and then neutralized with trypsin neutralizing solution (TNS, Cambrex) at the ratio of 1:1 (V/V). Testing antibodies or sera were incubated with adequate amount of H5-SP33 pseudotyped or trpsin-treated H1 pseudotyped viruses for 30 mins at RT. The mixture was then added to 293T cells in 96 well plates and continued the culture for 48 hours. Viral entry level was evaluated by measuring the luciferase activity in the target cells with a microplate luminometer.

Epitope Mapping of Antibody 8, 10 and 66

Plasmids and Constructs.

pcDNA3.1-H5-SP33, pCAGGS-H1(SC) and pCAGGS-H1(PR) were described as above. pCAGGS-H7 (FPV) which encodes HA proteins for A/FPV/Rostock/34 (H7N1) was kindly provided by Dr. X. Yang (Beth Israel Deaconess Medical Center). All the mutants of pcDNA3.1-H5-SP33 or pCAGGS-H7 (FPV) were constructed by the QuikChange method (Stratagene). Flow cytometry analysis of the binding of anti-H5 antibodies to HA expressing cells. Various full-length wild type HA and HA mutants expressing plasmids for H1, H5 or H7 were transfected transiently into 293T cells. 48 hours after transfection, anti-H5 antibodies (10 ug/ml) were incubated with transfected 293T cells at 4° C. for 1 hour. Cells were then washed three times with PBS containing 0.5% BSA and 0.1% NaN3. For the detection of anti-H5 antibodies' binding to HA transfected cells, FITC-labeled goat anti-human IgG (Pierce) was used as secondary antibody and incubated with cells at 4° C. for 30 min Cells were washed again as above and analyzed using a Becton Dickinson FACScaliber with CellQuest software.

Microneutralization Assay

The method was performed as described previously[48]. Briefly, 100 $TCID_{50}$ (median tissue culture infectious doses) of virus were mixed in equal volume with log 2 dilutions of antibody stock solution (1 mg/ml) in 96-well tissue culture plates, and incubated for 1 h at 37° C. Indicator MDCK cells ($1.5\times10^4$ cells/well) were added to the plates, followed by incubation at 37° C. for 20 hours. To establish the endpoint, cell monolayers were then washed with PBS, fixed in acetone, and viral antigen detected by indirect ELISA with a mAb against influenza A NP (A-3, Accurate).

Plaque Reduction Assay

A/Viet Nam 1203/2004 (H5N1) or A/Netherland/219/03 (H7N7) viruses (10,000 pfu) were incubated with anti-H5 scFv-Fcs at three different concentrations 100 ug/ml, 10 ug/ml and 1 ug/ml at 37° C. for 30 mins. The virus-antibody mixture was transferred onto MDCK cell monolayers in 12-well plates and incubated at 37° C. for 1 h and cells were then washed and overlaid with agar. After 4 days of incubation, the agar overlay was discarded, and plaques were visualized by crystal violet staining.

Hemagglutination Inhibition (HI) Assay

Avian influenza viruses preferentially bind to sialic acid receptors that contain N-acteylneuraminic acid α2,3-galactose (α2,3Gal) linkages while human viruses preferentially bind to those containing N-acetylneuaminic acid α2,6-galactose ((α2,6Gal) linkages. The molecular basis for receptor specificity is most likely determined by a complex set of residues in the viral HA. Hemagglutination-inhibition (HI) tests are a simple and widely used method to assess antibody responses to influenza hemagglutinin Stephenson et al. reported that by using horse erythrocytes and thereby increasing the proportion of α2,3 Gal linkages available for binding, the sensitivity of the hemagglutination assay was improved. In addition, the titers of the HI assay correlated well with the titers of the micro-neutralization assay. The pseudotyped viruses will be first titered using hemagglutination of horse erythrocytes as described. The initial high-throughput screens will be similarly performed using horse erythrocyte suspensions and assaying for the ability of the phage antibodies to inhibit the HI endpoint of the titered H5/N1 viruses. More detailed secondary screens for inhibition of H5N1 reporter virus entry and HI will be preformed using dose response studies with soluble scFvFc proteins produced by transiently transfected 293T cells and purified by protein A beads.

Viral Binding Inhibition Assay $0.5 \times 10^6$ 293T cells were incubated with H5-TH04-pseudotyped HIV viruses (~500 ng of p24) in the presence of anti-H5 mAbs, control mAbs, or in the absence of antibodies, in a buffer of PBS containing 0.5% BSA and 0.02% $NaN_3$ at 4° C. After an hour of incubation, cells were spun down. Supernatants were collected and tested for p24 levels using a HIV-1 $p24^{CA}$ capture ELISA kit (NCI, Frederick, NIH) to quantify the unbound viruses. The cells were then washed one or two times and lysed to quantify the cell-bound virus using the same method.

Cell Fusion Inhibition Assay 293T cells, ~90% confluent in six-well plates, were transfected with pcDNA3.1-H5-TH04 plasmid and pcDNA 3.1-N1 at a ratio of 4:1 (3 μg total DNA/well) using lipofectamine 2000 (Invitrogen). The culture medium was supplemented with 1 ml of anti-H5, control or mock mAbs at 6 hours post-transfection, and cells cultured for 36 hours. Cells were observed for syncytia formation with a phase-contrast microscope. Photomicrographs were taken at 10× magnification.

Expression and Preparation of Various HA Proteins for Panning

HA1 is an N-terminal fragment of HA of H5N1 A/Thailand/2(SP-33)/2004 (H5-TH04), residues 11 to 325 (H3 numbering). The gene was codon-optimized and expressed as fusion protein with a C-terminal 9 amino-acids tag (C9-tag: GTETSQVAPA). The fusion protein HA1-C9 was expressed in 293T cells transiently and the secreted proteins in supernatant were harvested 48 hours after transfection and purified from the supernatant by affinity chromatography using Protein A Sepharose that coupled covalently with anti-C9 antibody 1D4 (National Cell Culture Center). The method to produce HA0 protein of H5-VN04 is the same as described below for crystallization of H5-F10 complex but without the baculovirus coinfection for furin-cleavage.

ELISA 0.2 μg of pure H5 HA proteins was coated onto 96-well Maxisorb ELISA plate (Nunc, NY) at 2 μg/mL in PBS at 4° C. overnight. The plate was washed with PBS for 3 times to remove uncoated proteins. For regular ELISA, 1 μg/mL of anti-H5 scFv-Fcs followed by HRP-anti-human IgG1 were used to detect the binding of anti-H5 scFv-Fcs to H5 HA proteins. For competition ELISA, 50 μL ($10^{12}$ pfu) of anti-H5 phage-scFvs were mixed with 5 μg/mL of anti-H5 scFv-Fcs and applied to H5-VN04 HA coated ELISA plate. The competition of scFv-Fcs for the binding of phage-scFvs to HA0 were determined by measuring the remaining binding of phage-scFvs using HRP-anti-M13. The optical density at 450 nm was measured after incubation of peroxidase tetramethylbenzidine (TMB) substrate system (KPL, Gaithersburg Md.).

Expression, Purification, and Crystallization of the H5-F10 Complex

The gene encoding single chain (VH-linker-VL) F10 (scFv) was cloned into pSynI vector containing an N-terminal periplasmic secretion signal pelB, and a C-terminal 6×His tag. F10 scFv was expressed in XL10 cells in 2YT media containing 0.1% glucose (w/v) at 25° C. for 15 hours with 0.5 mM IPTG. Protein was purified first by Hisbind Ni-NTA (Novagen) according to the manufacturer's instructions, and then by Superdex 200 (Amersham Biosciences) in 50 mM Tris-HCl, 0.5 M NaCl, pH 8.

The ectodomain of H5-VN04 HA gene was expressed in insect cells as a fusion protein by adapting the protocol described previously[6]. This construct contains a C-terminal trimerizing 'foldon' sequence from the bacteriophage T4 fibritin to stabilize the trimeric structure, followed by a thrombin site and a $His_6$ tag. The cDNA of the fusion protein was cloned into the baculovirus transfer vector, pAcGP67A (BD Biosciences, Bedford, Mass.), to allow for efficient secretion of recombinant protein. To obtain fully cleaved HA (as HA1-HA2 trimers), sf9 cells were co-infected with baculovirus stocks of HA0 and furin at an empirically derived ratio. The furin cDNA was a gift from Dr. Robert Fuller (University of Michigan). Three days after infection, the cells were spun down and the supernatant was incubated with Ni-NTA beads (Qiagen Inc., Valencia, Calif.). The beads were washed with TBS buffer (10 mM Tris.HCl, 80 mM NaCl, pH8.0) with 10 mM imidazole, and eluted with TBS with 250 mM Imidazole. The eluted H5 protein was dialyzed against TBS buffer and further purified by ion-exchange using Mono Q HR10/10 column (GE Healthcare, Piscataway, N.J.). The purified H5 was digested by thrombin overnight and further purified by Superdex 200 column in TBS buffer.

H5-F10 complexes were formed by mixing the two purified components, and isolated by Superdex 200 in TBS buffer. Peak fractions were pooled and concentrated to ~11 mg/ml. The integrity of the H5 trimer was examined using Gel filtration (Superdex 200 column) and SDS-PAGE. Crystals grew by the hanging drop vapor diffusion method at 22° C. Two μL of H5-F10 were mixed with an equal volume of 12.5% PEG 1K, 25% ethylene glycol, 100 mM Tris, pH 8.5. Crystals were flash-frozen in liquid nitrogen prior to data collection.

Co-Crystallization of the H5-F10 Complex

For co-crystallization of the H5-F10 complex, F10 was expressed in *E. coli* and purified by Ni-NTA and gel filtration. H5 was expressed by co-infection of H5 and furin baculovirus stocks in sf9 cells, and purified by Ni-NTA, anion ion exchange, and gel filtration chromatography. H5-F10 complexes were obtained by mixing H5 with an excess of F10 and isolated by gel filtration. Crystals were grown by mixing 2 □L of complex (~11 mg/ml) with an equal volume of 12.5% PEG 1K, 25% ethylene glycol, 100 mM Tris, pH 8.5 using the hanging drop vapor diffusion method at 22° C. The crystal structure was determined at 3.2 Å resolution by Molecular Replacement and refined to an $R_{FREE}$ of 0.29 with excellent geometry.

Data Collection, Structure Determination, and Refinement

X-ray diffraction data were collected at the Stanford Synchrotron Radiation Laboratory (SSRL) beam-lines 7.1 and 9.2. Data were processed with $XDS^7$ and the HKL2000 package.

The structure of the H5-F10 complex was determined by molecular replacement with PHASER using the structure of H5 (A/Vietnam/1194/04; PDB code 2IBX) and the scFv structure of SARS nAb 80R (PDB code 2 GHW) as search models. The scFv structure homology model was build with WHATIF[9]. The asymmetric unit contains two H5 trimers and six F10 molecules.

Solutions from molecular replacement were subjected to several rounds of refinement with the program REFMAC5 with simulated annealing in CNS and manual model rebuilding with Coot and Xtalview. The final model includes 506/503/503/496/495/496 residues for 6 independent copies of HA, respectively, 233 residues for each nAb10, 24

N-acetyl-d-glucosamine and 6β-d-mannose, 0 water molecules. Geometric parameters were assessed with PROCHECK and Rampage.

Protection of Mice with hMabs Against H5

All mouse studies were performed in USDA and CDC accredited biosafety level 3 (BSL3) animal facility in accordance with protocols approved by the CDC Animal Care and Use Committee. Female 8-10 weeks old Balb/C mice (5 per group) were used in all experiments. For all groups, mice were observed for 2 weeks, weighted and deaths noted daily.

Prophylactic Mouse Study.

Three hMabs (D8-IgG1, F10-IgG1 and A66-IgG1) or control hMab 80R-IgG1 at 2 doses of 10 mg/kg and 2.5 mg/kg[53] were administered into mice intraperitoneally (i.p.). 24 hours after hMabs administration, all groups of mice were challenged with A/Vietnam/1203/04 (H5N1) or A/HK/483/97 (H5N1) intranasally (i.n.) at dose of 10 MLD$_{50}$ (50% mouse lethal dose) viruses under light anesthesia.

Therapeutic Mouse Study.

Mice were first infected i.n. with 10 MLD$_{50}$ of A/Vietnam/1203/04 (H5N1) or A/HK/483/97 (H5N1). Three hMabs against H5 or control hMab at 10 mg/kg were then i.p. administered into mice 24, 48 and 72 hours after A/Vietnam/1203/04 (H5N1) infection. For A/HK/483/97 (H5N1) infected mice, hMabs were only injected 24 hours after viral challenge.

Identification of Anti-H5 Phage Antibodies

Antibodies Against HA1.

Purified recombinant HA1 was used to select antibodies from two non-immune human scFv libraries separately. After two rounds of selection on HA1, 58 out of 96 clones screened by ELISA were HA1 specific positive clones. Three unique anti-HA1 scFvs were identified (38B and 1C) by sequencing analysis of the 58 HA1-positive clones. Similar selection and screening experiments were repeated; no new clones were identified but obtained the same three scFvs as described above.

Antibodies Against Ectodomain of H5 (HA0).

Purified recombinant trimeric HA0 was used to select the same antibody libraries as that used for HA1. After two rounds of selection on HA0, a total of 392 clones were screened for HA0 specific binding by ELISA. 97 clones recognized HA0 protein specifically. Ten unique anti-HA0 scFvs (7, 8, 10, 17, 40, 66, 80, 88, 90 and 98) were identified by sequence analysis. Six different VH and 10 different VL genes were revealed (some scFvs shared the same VH gene). Five out of the six different VH belong to one gene family, IGHV1-69. The VL genes were much diverse than the VH genes, three out of the 10 VL are Kappa chain. (FIG. 3).

Establishment of a Reliable Single-Round Reporter Virus System

The single-round HIV luciferase reporter viruses of H5N1 or H1N1 pseudotyped by H5-SP33, H1-SC/1918 or H1-PR/34 were made by co-transfection of 293T cells with 4 plasmids that are pcDNA3.1-H5-SP33, HIV packaging vector pCMVΔR 8.2 encoding HIV-1 Gag-Pol, transfer vector pHIV-Luc encoding the firefly luciferase reporter gene under control of the HIV-1 LTR, and expressing plasmid pcDNA3.1-N1. 36 hours post-transfection, viral supernatants were harvested and stored at 4° C. The titer of HA0-pseudotyped viruses was measured by infecting 293T cells. Including the N1 expressing plasmid in the transfection of making pseudotyped viruses can dramatically increase the titer of H5-pseudotyped viruses The proper behavior of the H5-pseudotyped viruses was examined by using ferret immune serum against H5N1 (A/VietNam/2004). These viruses can be neutralized potently by anti-serum, while not by pre-bleeding serum. Thus a reliable single-round high efficient reporter virus system was established for efficient screening of neutralizing antibody Example 2: Identification of Neutralizing Antibodies Against H5N1 Using Viruses Pseudotyped with 115-SP33 and Microneutralization Assay Results of Neutralization Assay Using Pseudotyped Viruses.

Bivalent scFvFcs of anti-H5 antibodies were produced and tested for neutralization activities against HA0-pseudotyped viruses. We found that 2A is a moderate neutralizing antibody, 38B and 1C are non-neutralizing antibodies (data not shown). The 2A antibody has been used as a useful anti-HA reagent for other assays (epitope mapping) described below.) By using HA0 trimer as a target, we have identified 10 new unique antibodies against HA0. These Abs were screened for neutralization activity by using a novel high-throughput phage-scFvs screening method that has been recently set up in our lab. Briefly, the phage-scFvs of individual clones were directly used in a neutralization assay immediately following being screened by ELISA for positive clones in 96-well plates. In this schema, neutralization activity will be known in 48 hours. By doing this, we bypass steps of subcloning and expressing of soluble Abs which are time-consuming.

As shown in the figure, neutralizing Abs that were indicated by phage turned out to be potent neutralizing when confirmed with soluble scFvFc Abs. All the 10 antibodies screened by phage-scFvs are potent neutralizing Abs. We also converted three of the 10 antibodies (D8, F10 and A66) into full-length human IgG1, the potent neutralization activity were again seen with H5-SP33 pseudotyped viruses. The three antibodies also cross-neutralized H1N1: potently neutralized stain of H1-SC/1918 and moderately neutralized strain of H1-PR/34 (FIGS. 4A-4C).

Results of microneutralization assay. As shown in FIGS. 4A-4C and 9B, the 10 anti-H5 antibodies exhibited different levels of neutralization. F10-Fc, A66-Fc, E88-Fc and E90-Fc appeared to be the most potent inhibitors, which neutralize more than 95% of 10,000 pfu virus at 10 ug/ml and more than 50% at 1 ug/ml. We also have seen complete plaque reduction when 100 pfu was used for these four antibodies at 10 ug/ml or 1 ug/ml (data not shown).

The 10 antibodies (scFv-Fcs) were found to neutralize H5 pseudo-viruses (virus-like particles with HIV-1 only cores that display H5 on their surface), in this case from the Glade 1 virus, A/Thailand/2-SP-33/2004 (H5N1) ("H5-TH04"). All 10 antibodies also exhibited high but distinct levels of neutralization against H5-VN04 (Clade 1) and A/Indonesia/5/2005 ("H5-1N05", Clade 2.1) viruses in a stringent plaque reduction assay, suggesting that the neutralization epitope(s) is conserved across different H5 clades. However, none of the Abs neutralized a Group 2 virus, HPAI H7N7 strain, A/Netherlands/219/03 (H7N7) (H7-NL03) (FIG. 4).

Figure 9A:
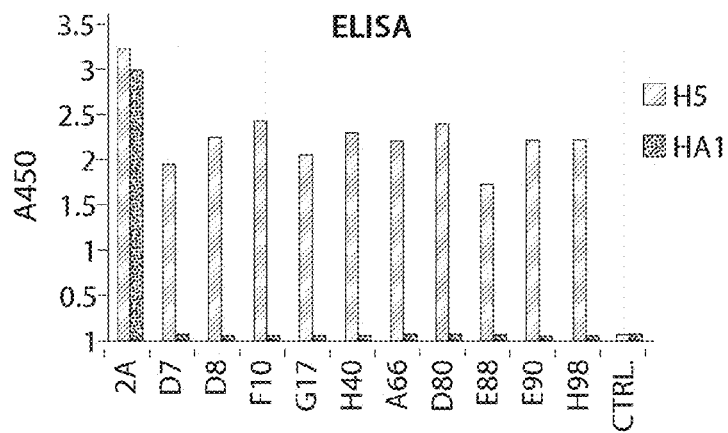
FIG. 9 show the binding of anti-H5 scFv-Fcs to H5 or HA1 by ELISA and competition ELISA. (a) 1 ng/mL of anti-H5 scFv-Fcs followed by HRP-anti-human IgG1 were used to detect the binding of anti-H5 scFv-Fcs to HA1 (H5-TH04) or H5 (H5-VN04) coated on an ELISA plate. An antibody selected against the HA1 subunit, mAb 2A scFv-Fc, bound to both HA1 and H5. The 10 potent neutralizing scFv-Fcs bound to H5 but not HA1. (b) $10^{12}$ pfu of anti-H5 phage-scFvs were mixed with 5 ng/mL of anti-H5 scFv-Fcs and added to H5 (H5-VN04)-coated plates, washed, and followed by HRP-anti-M13 to detect phage-scFvs bound to H5. mAb 2A-Fc did not compete for the epitope recognized by the 10 H5-selected Abs. All H5-selected scFv-Fcs cross-competed. Of these, Ab F10 (phage-scFv) binding to the H5 trimer was the least inhibited by the other scFv-Fcs suggesting that it has the highest affinity among all Abs tested.
Figure 9B:
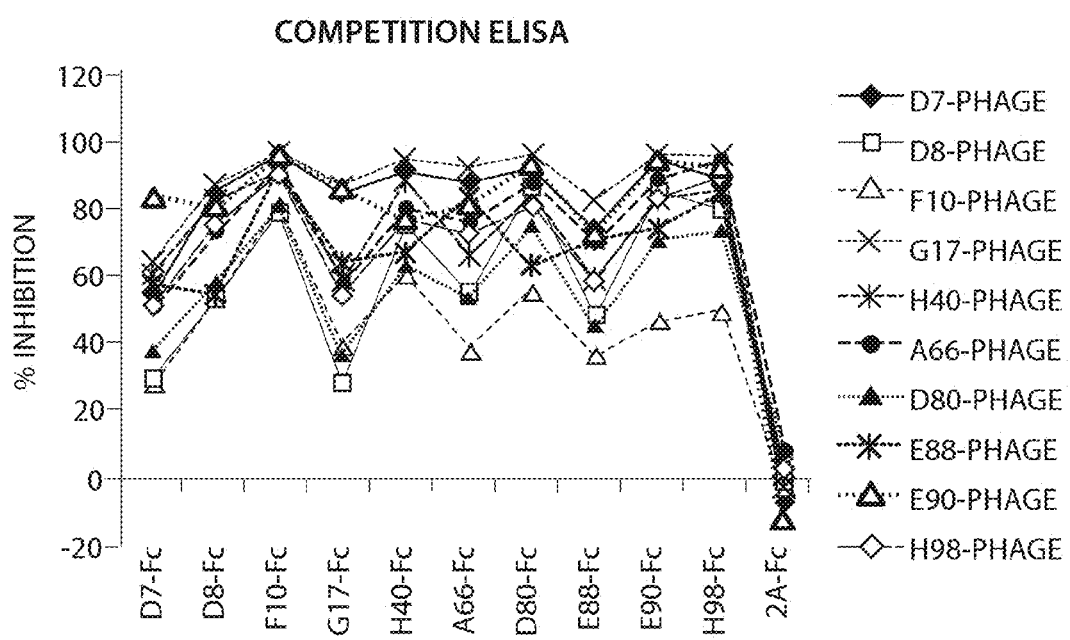
Figure 10:
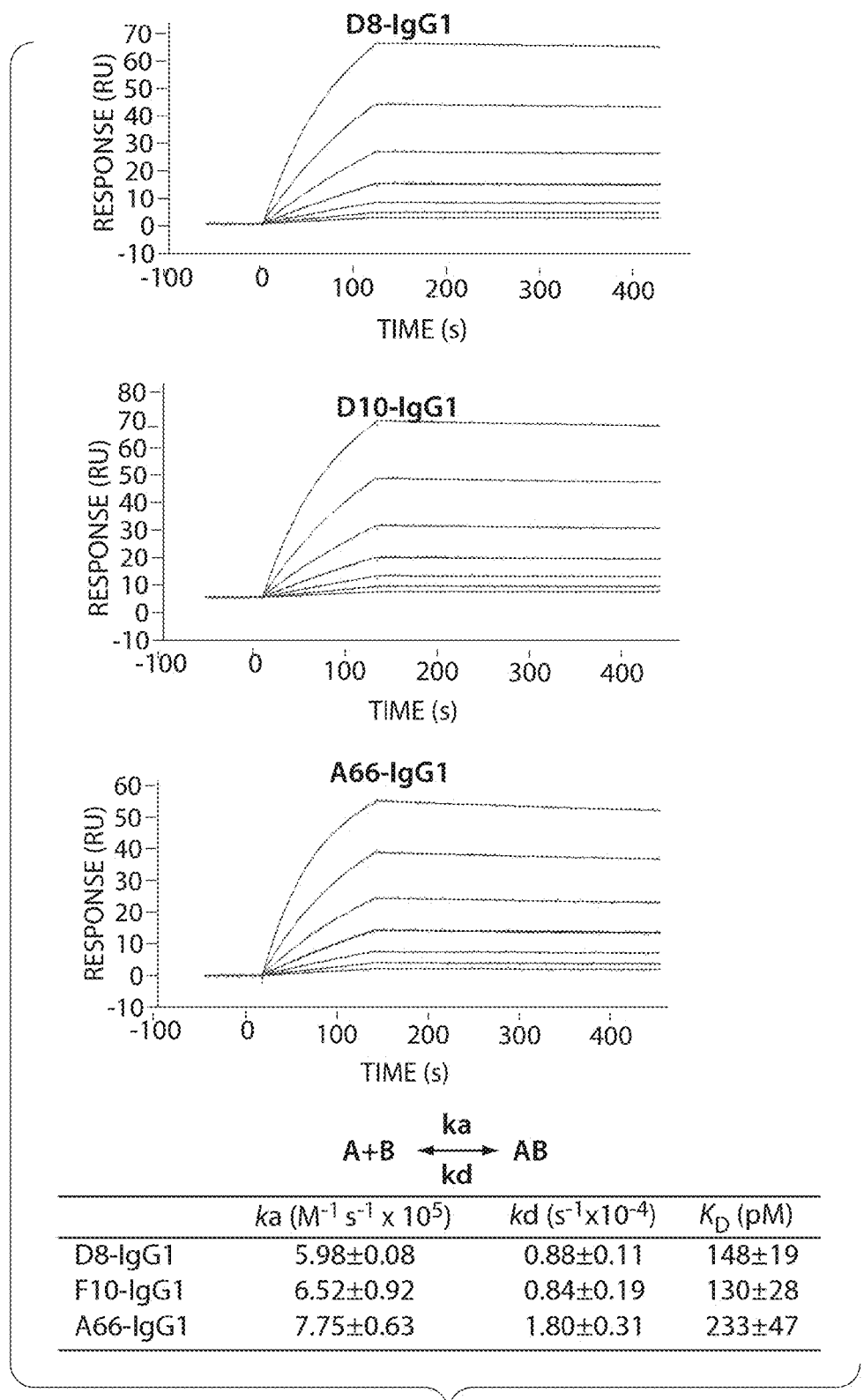
FIG. 10 shows the kinetic and thermodynamic characterization of the binding of H5 to nAbs D8, F10 and A66-IgG1s. nAbs were captured on a CM4 chip via anti-human IgG1; trimeric H5 (H5-VN04) at various concentrations (20, 10, 5, 2.5, 2.5, 1.25, 0.625 nM) was injected over the chip surface. Binding kinetics were evaluated using a 1:1 Langmuir binding model. The recorded binding curves (with blank reference subtracted) and the calculated curves are closely superimposable. Each ka, kd and $K_D$ value represents the mean and standard error of three experiments.

All 10 nAbs bound to trimeric H5 and cross-competed against each other (FIG. 9), indicating that they recognize an overlapping epitope. Based on this finding as well as VH sequence diversity and neutralization potency, three nAbs (D8, F10 and A66) were selected and converted into full-length human IgG1. All three nAb IgG1s bound to recombinant H5 (H5-VN04) in vitro with high affinity (Kd~100-200 pM) and very slow dissociation rates (kd~$10^{-4}$ s$^{-1}$) (FIG. 10).

Example 3: Kinetic Characterization of the Binding of HA0 (the Ectodomain of HA of A/Vietnam1203/04) to D8-IgG1, F10-IgG1 and A66-IgG1 by Using BIAcore T-100

Mabs were captured on a CM4 chip via anti-human IgG1, and trimeric HA0 at various concentrations (20, 10, 5, 2.5, 2.5, 1.25, 0.625 nM) was injected over the chip surface. Binding kinetics was evaluated using a 1:1 Langmuir binding model. The recorded binding curves (with blank reference subtracted) are shown in black and the calculated curves in red. All ka, kd, KD represent the means and standard errors of three experiments. Using Biacore T100 and Biacore T100 evaluation software, we determined the kinetic rates and affinity constants for the three anti-HA MAbs by fitting to a 1:1 Langmuir model. As shown in the figure below, similar ka, kd, and KD of D8 and F10 were observed, and A66 had a 1.8 fold lower KD than 8 and 10 due to a relative faster dissociation rate than the other two antibodies. The complexes between Mabs and HA0 were stable as illustrated by a very slow dissociation rate ($8.8 \pm 1.1 \times 10^{-5}$ s$^{-1}$ ~$1.8 \pm 0.3 \times 10$ S$^{-1}$) and high affinity binding with H5 trimer at pM level. (FIG. 10)

Example 4: Prophylactic and Therapeutic Effect of Anti-H5 Antibodies

The protective efficacy of human nAbs against H5N1 and H1N1 virus infection was evaluated in a BALB/c mouse model. Mice were treated with different doses of nAb either before or after lethal viral challenge.

Prophylactic Efficacy (FIGS. 7 a, b, g and h).

Figure 7A:
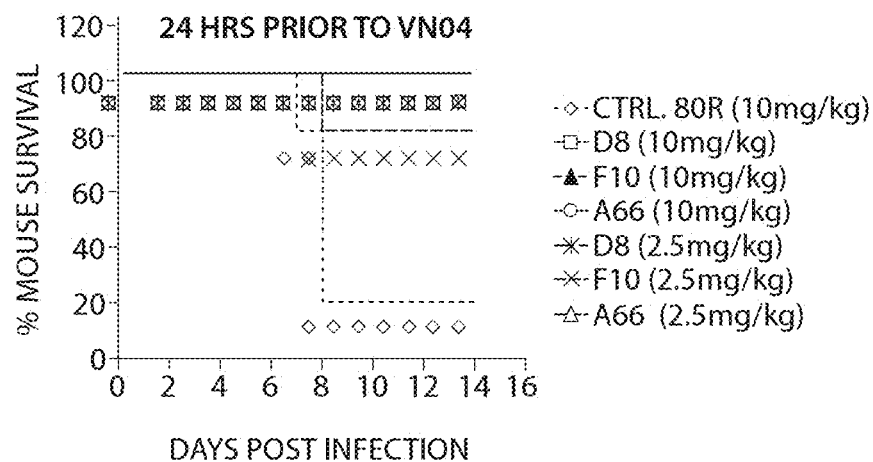
FIG. 7 shows the prophylactic and therapeutic efficacy of anti-H5 nAbs in mice. Mice were treated with different doses of nAb either before or after lethal viral challenge. Prophylactic efficacy (a, b, g and h). Mice were treated with anti-H5 nAbs or control mAb 24 hour before lethal challenge by intranasally (i.n.) with 10 median lethal doses ($MLD_{50}$) of the H5N1 or H1N1s. (a) Intra-peritoneal (i.p.) injection of 10 mg/kg of any of the three nAbs provided complete protection of mice challenged with H5-VN04 (A/Vietnam/1203/04 (H5N1), Clade 1). A lower antibody dose (2.5 mg/kg) was also highly protective. (b) Prophylactic protection against H5-HK97 (A/HongKong/483/97 (H5N1), Clade 0) virus was observed in 80-100% of the mice treated with 10 mg/kg of any of the three nAbs. (g) Any of the three nAbs (at 10 mg/kg of single injection) provided complete protection of mice challenged with H1-WSN33 (A/WSN/1933 (H1N1)) viruses. (h) D8 and F10 completely protected mice challenged with H1-PR34 (A/Puerto Rico/8/34 (H1N1)) when given at 10 mg/kg of single injection. A66 provided complete protection of mice when 25 mg/kg of antibody was given as a single injection. Therapeutic efficacy (c-f). Mice were inoculated with H5-VN04 and injected with nAbs at 24, 48, 72 hpi (c, e and f) or with H5-HK97 at 24 hpi (d). I.p. treatment with 15 mg/kg (a therapeutically achievable dose in humans) of any of the 3 nAbs at 24 h post-inoculation (hpi) protected 80-100% of mice challenged with 10-times the $MLD_{50}$ of either H5-VN04 or H5-HK97 virus.
Figure 7B:
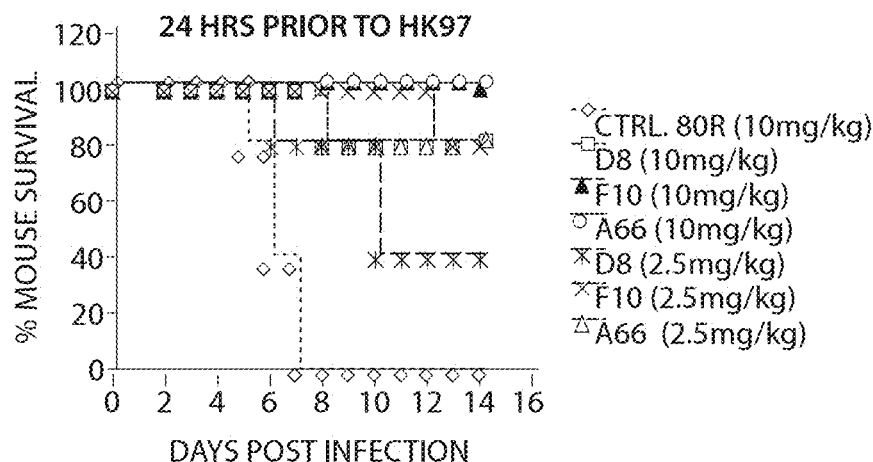
Figure 7C:
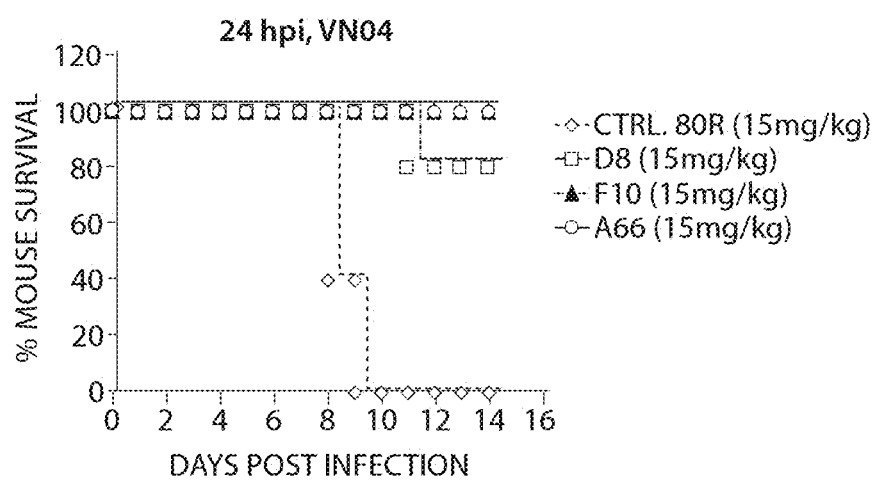
Figure 7D:
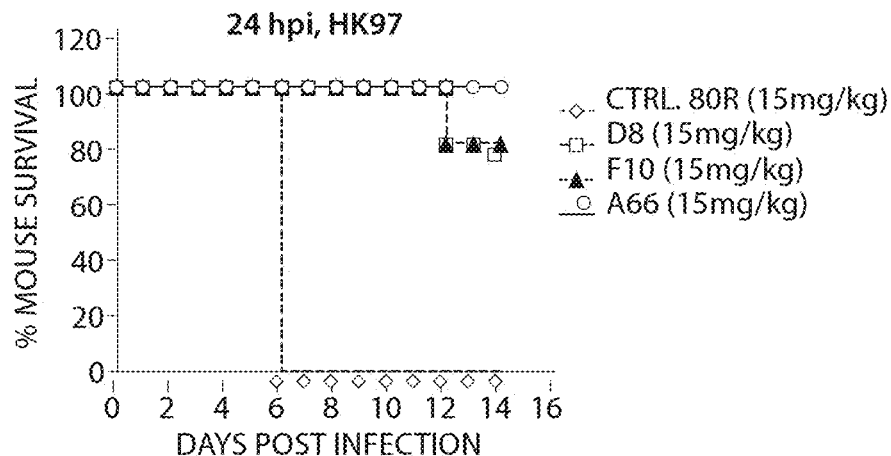
Figure 7E:
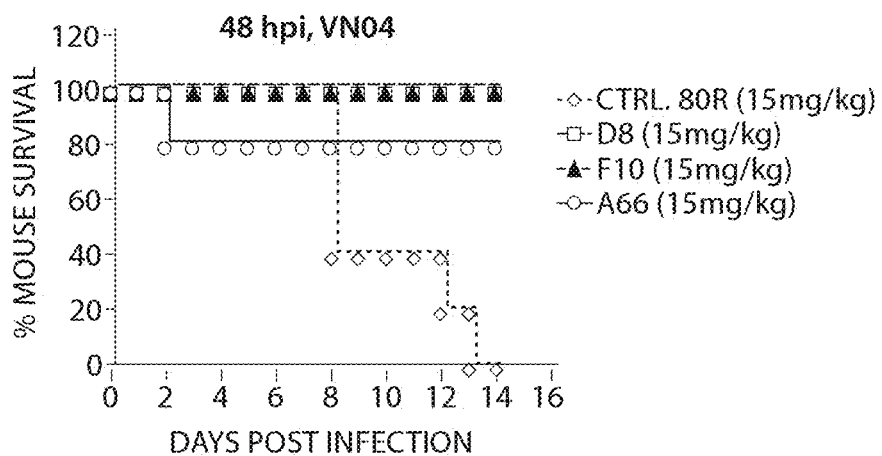
Figure 7F:
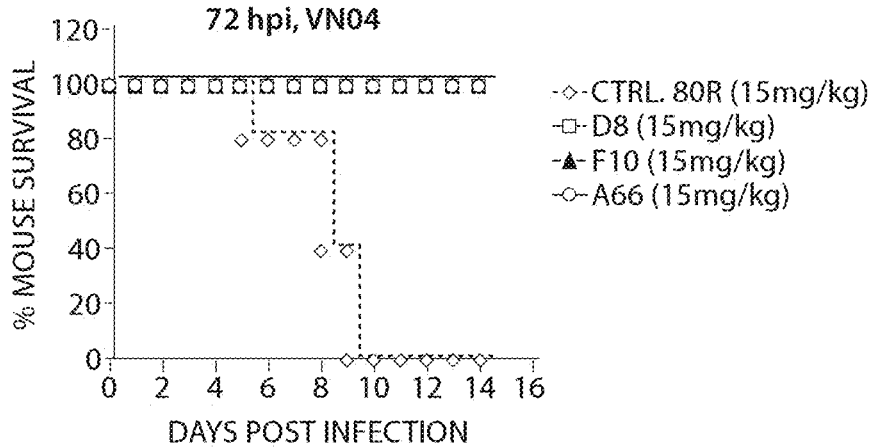
Figure 8A:
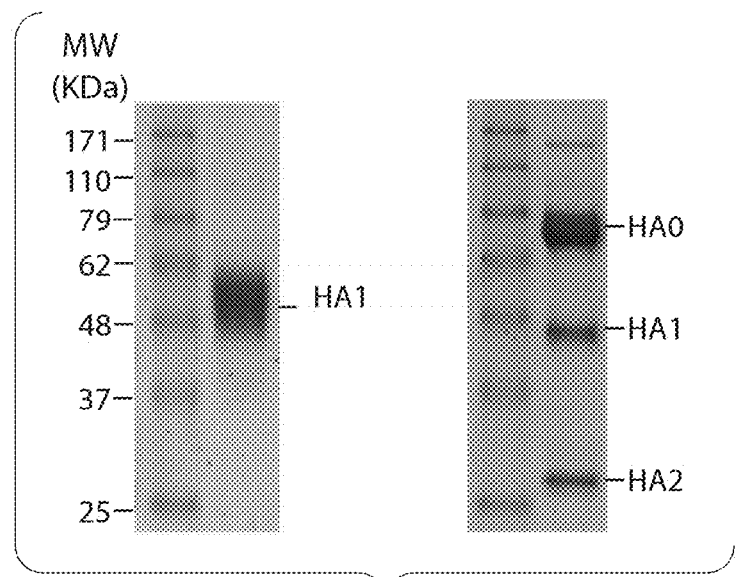
FIG. 8 illustrates SDS-PAGE and gel filtration analysis of HA proteins. (a) Antibody 2A was obtained from a separate HA1-targeted selection against the HA1 (residues 11-325) fragment of H5-TH04 (left panel). H5 HA (H5-VN04 strain) used for library selection is shown in the right panel, (b) H5-VN04 (H5) and scFv F10 complex. HA0 was fully cleaved into HA1 and HA2 by co-expression with furin (left panel). Complexes were formed by first mixing H5 and F10 at a molar ratio of 1:10, and then purified by gel filtration.
Figure 8B:
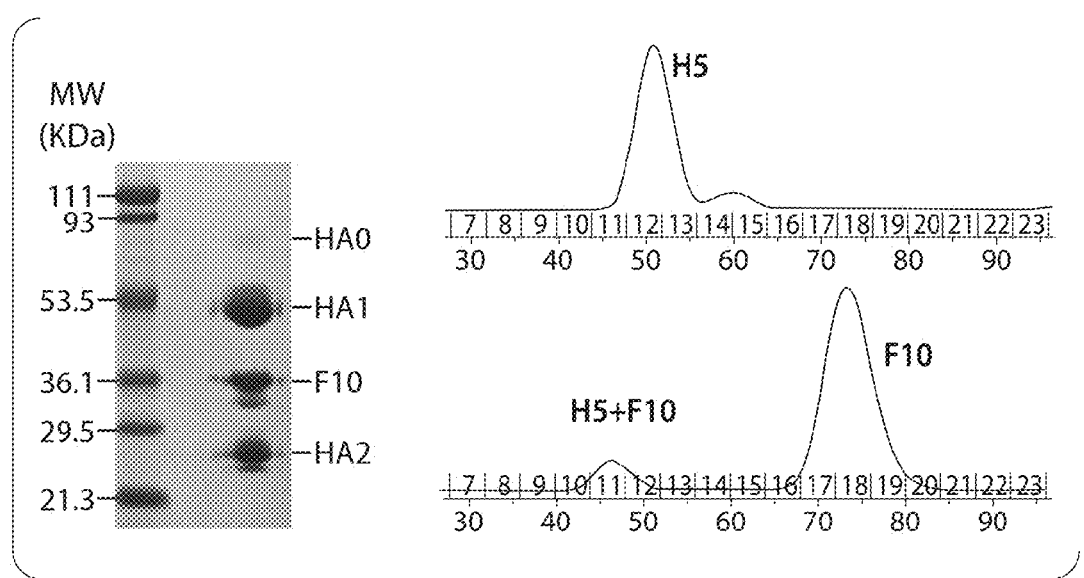

Mice were treated with anti-H5 nAbs or control mAb 24 hour before lethal challenge by intranasally (i.n.) with 10 median lethal doses (MLD$_{50}$) of the H5N1 or H1N1s. Intra-peritoneal (i.p.) injection of 10 mg/kg of any of the three nAbs provided complete protection of mice challenged with H5-VN04 (A/Vietnam/1203/04 (H5N1), Clade 1). A lower antibody dose (2.5 mg/kg) was also highly protective. (FIG. 7a) Prophylactic protection against H5-HK97 (A/HongKong/483/97 (H5N1), Clade 0) virus was observed in 80-100% of the mice treated with 10 mg/kg of any of the three nAbs. (FIG. 7b) Any of the three nAbs (at 10 mg/kg of single injection) provided complete protection of mice challenged with H1-WSN33 (A/WSN/1933 (H1N1)) viruses. (FIG. 7g) D8 and F10 completely protected mice challenged with H1-PR34 (A/Puerto Rico/8/34 (H1N1)) when given at 10 mg/kg of single injection. A66 provided complete protection of mice when 25 mg/kg of antibody was given as a single injection. (FIG. 7h)

Therapeutic Efficacy (FIG. 7c-f).

Figure 2:
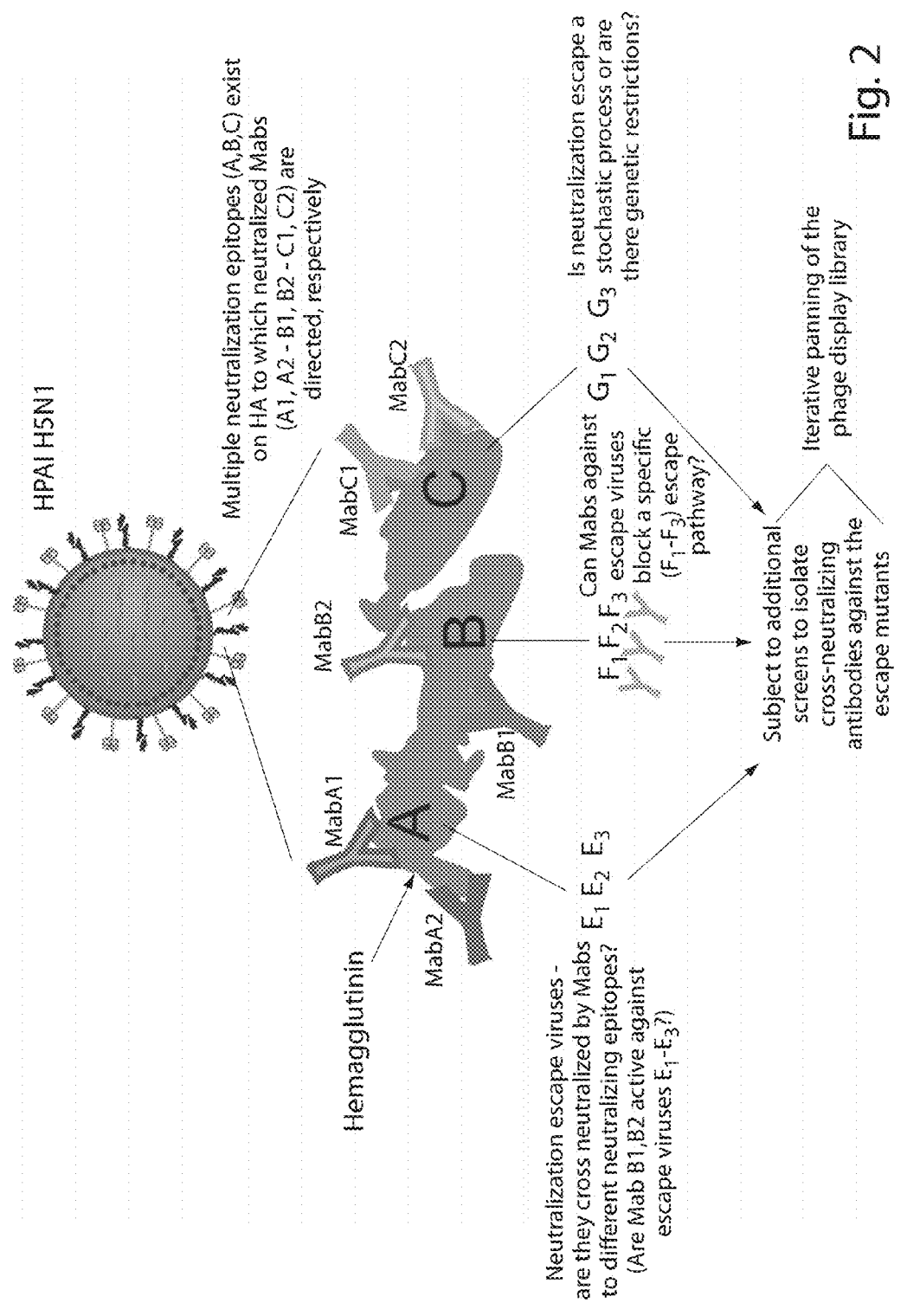

Mice were inoculated with H5-VN04 and injected with nAbs at 24, 48, 72 hpi (FIGS. 7 c, e and f) or with H5-HK97 at 24 hpi (FIG. 7 d). I.p. treatment with 15 mg/kg (a therapeutically achievable dose in humans) of any of the 3 nAbs at 24 h post-inoculation (hpi) protected 80-100% of mice challenged with 10-times the MLD$_{50}$ of either H5-VN04 or H5-HK97 virus (FIG. 7c-d). Mice treated with the same dose of nAbs at 48 or 72 hpi with H5-VN04 showed similar or higher levels of protection (FIG. 7 2e-f). Surviving mice in all anti-H5 nAb treatment groups remained healthy and showed minimal body weight loss over the 2-week observation period (data not shown).

Figure 12:
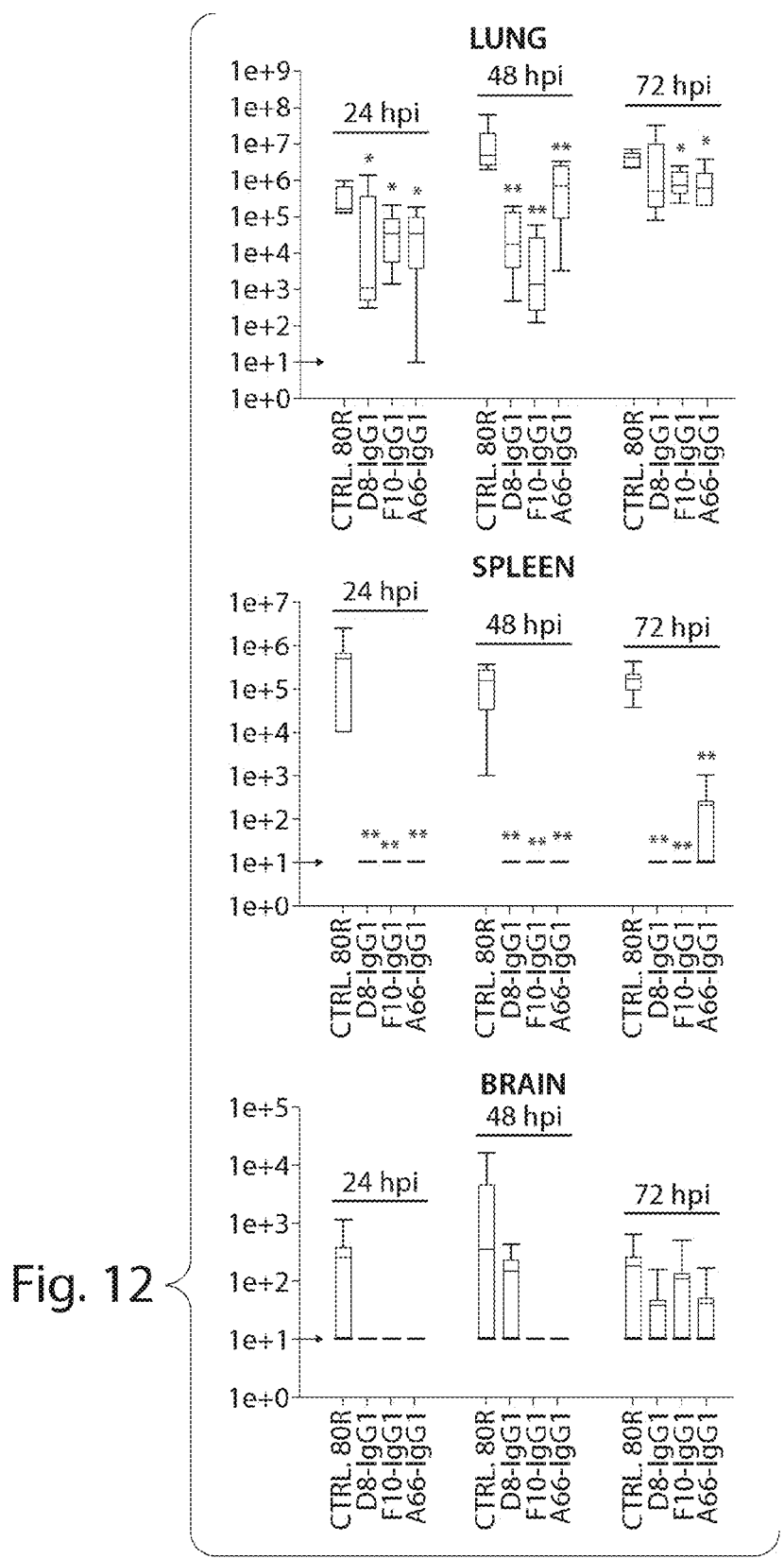
FIG. 12 shows viral titers in lung, spleen and brain of mice treated with anti-H5 nAbs after H5-VN04 challenge. BALB/c mice (n=5) were treated by i.p. injection of 15 mg/kg of mAb at 24, 48 or 72 hrs after i.n. infection with 10 $MLD_{50}$ of H5-VN04. Viral titers were determined in lung, brain, and spleen collected at 96 hpi. Data are displayed in box-and-whiskers form in which the box extends from the $25^{th}$ to the $75^{th}$ percentile, with a horizontal line at the median. Whiskers above and below the box indicate the extreme values. Results of Student T-test statistic analysis are noted with a single star (*) for $p<0.05$, and double stars (**) for $p<0.01$. The arrows crossing the Y axis indicate the detection limit of the titration.

Example 5: Suppression of Viral Titer in Tissues by Anti-115 Antibodies in a Therapeutic Animal Study The anti-viral effect of nAbs used therapeutically was further investigated by measuring virus titer 4 days post-challenge either in lungs, as an indicator of inhibition of local replication, or in spleen and brain, indicative of the systemic spread that is characteristic of H5N1 infection. The nAbs mediated a significant suppression of viral replication in lungs of H5 nAb treated mice as compared to controls when given within 48 hours of challenge (FIG. 12). Notably, two of the nAbs, D8 and F10, also showed antiviral effect when given at 72 hpi. Systemic virus spread to the brain was low in control animals, obscuring any effect of nAb treatment. However, the impact of nAb therapy on systemic spread was dramatically demonstrated by ≥1000-fold suppression of virus spread to the spleen even when the three nAbs were given within 72 hpi.

Example 6: Initial Epitope Mapping of Antibody D8, F10 and A66

Various full-length wild type HA and HA mutants expressing plasmids for H5-SP33 were transfected transiently into 293T cells. 48 hours after transfection, anti-H5 antibodies (10 ug/ml) were incubated with transfected 293T cells at 4° C. for 1 hour. Cells were then washed three times with PBS containing 0.5% BSA and 0.1% NaN3. For the detection of anti-H5 antibodies' binding to HA transfected cells, FITC-labeled goat anti-human IgG (Pierce) was used as secondary antibody and incubated with cells at 4° C. for 30 min. Antibody 2A was used as a control antibody to indicate the expression of each mutant. As we can see from the table below, the epitopes for Mab D8, 1F0 and A66 are similar and they are located at positions of 307 on HA1 and 52, 59, 65, 93 on HA2. The position of these amino acids were highlighted in the crystal structure of H5 (A/Vietnam/1203/04 (H5N1))

Example 7: Binding and Neutralization of Cluster H1 Viruses

Figure 11:
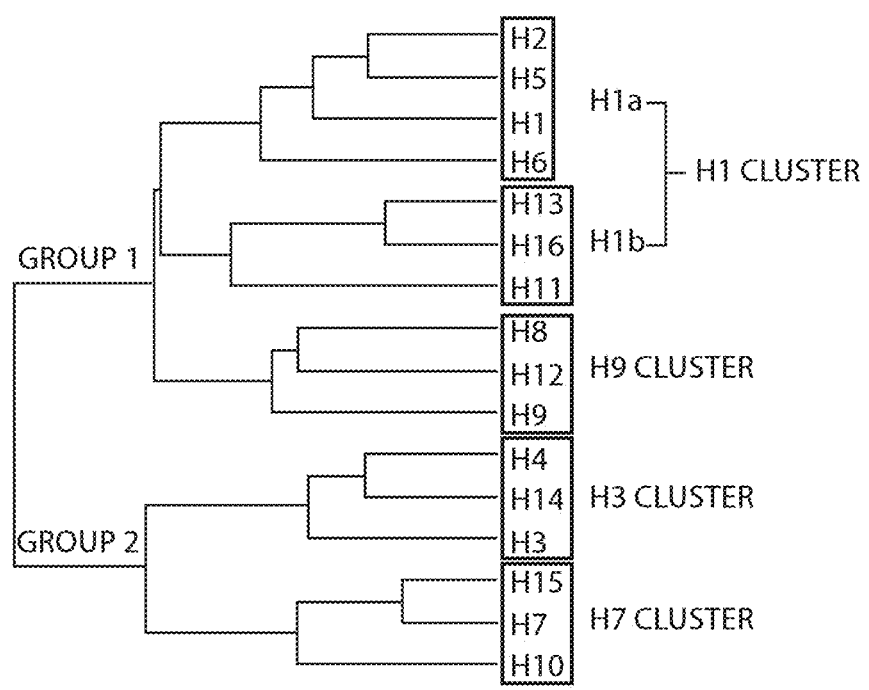
FIG. 11 shows the phylogenetic relationships and sequence comparison among HA subtypes. Phylogenetic tree of the 16 HA subtypes of influenza A viruses based on amino-acid sequences. Four clusters of HA subtypes are shaded in different colors. The sequences used for analysis were: H1 (A/South Carolina/1/1918), H2 (A/Japan/305/1957), H3 (A/Aichi/2/1968), H4 (A/duck/Czechoslovakia/56), H5 (A/VietNam1203/2004), H6 (A/chicken/California/431/00), H7 (A/Netherland/219/03), H8 (A/turkey/Ontario/6118/68), H9 (A/swine/HK/9/98), H10 (A/chicken/Germany/N49), H11 (A/duck/England/56), H12 (A/duck/Alberta/60/76), H13 (A/gull/Maryland/704/77), H14 (A/mallard/Astrakhan/263/1982), H15 (A/shearwater/West Australia/2576/79) and H16 (A/black-headed gull/Sweden/2/99).

The cross-clade neutralization of H5N1 viruses (FIG. 4) prompted testing for neutralization of other HA subtypes within the Group 1 H1 cluster (FIG. 11). All three nAbs bound to cells expressing full-length H1 ((A/South Carolina/1/1918 (H1N1) ("H1-SC1918") and A/Puerto Rico/8/34 (H1N1) ("H1-PR34")), H2 (A/Japan/305/57 (H2N2)) ("H2-JP57"), H6 (A/chicken/New York/14677-13/1998 (H6N2)) (H6-NY98), but not a Group 2 subtype, H7 ((A/FPV/Rostock/34 (H7N1) ("H7-FP34")) (FIG. 4). They also neutralized H1-SC1918- and H1-PR34-pseudotyped virus infection (FIG. 4); and in addition, F10 neutralized PR34 (H1N1), A/Ohio/83 (H1N1) ("H1-OH83") and A/Ann Arbor/6/60 (H2N2) infection (FIG. 4). These results suggest that these nAbs recognize an epitope on HA that is not only highly conserved among H5 clades, but is also present on H1, H2 and H6 subtypes, and potentially subtypes within other clusters. We therefore decided to investigate the mechanism of virus neutralization in detail.

Example 8: nAbs Inhibit Cell Fusion but not Virus Binding

Two ways in which anti-HA Abs can mediate neutralization are blocking HA binding to its cellular receptor, and inhibition of virus-host membrane fusion by interfering with low-pH induced conformational changes of HA. We found that the three nAbs neither affected virus binding to cells nor inhibited haemagglutination (binding and cross-linking of red blood cells), while a mouse anti-H5 nAb, 17A2.1.2, and ferret anti-H5N1 serum, both of which inhibit haemagglutination, reduced binding to background levels.

We next tested the ability of the nAbs to inhibit fusion of host cell membranes using a model system in which 293T cells at high density were co-transfected with H5- and N1-expressing plasmids from H5-TH04. Surface-expressed viral proteins cause cells to fuse and form syncytia, which occurs spontaneously within 36-48 hrs post-transfection under normal culture conditions. When nAbs were added 6 hrs post-transfection and observed 36 hrs later, complete inhibition of syncytia formation was observed in all 3 cases In the absence of nAbs, cells exposed briefly (3-4 minutes) to an acidic medium (pH 5) 30 hrs post-transfection form extensive syncytia. The nAbs (5 μg/ml) also completely blocked syncytia formation under these conditions (data not shown). Together, these results indicate that all three nAbs inhibit membrane fusion without interfering with receptor binding.

Example 9: Structural Characterization of the nAb Epitope

We next determined the epitope and mode of binding of one of the nAbs, F10, by solving the crystal structure of its scFv fragment in complex with HA (H5-VN04) at 3.2 Å resolution, and by mutagenesis. (FIG. 6 and Table 4)

In the complex, each H5 trimer binds three molecules of F10, at symmetry-related sites, burying ~1500 Å$^2$ of protein surface per antibody; the structure of H5 itself is not significantly altered by F10 binding. HA is synthesized as a single chain, HA0, that is activated by proteolytic cleavage into two subunits, HA1 and HA2. Cleavage leads to the burial of the "fusion peptide" (comprising the first ~21 residues of HA2) into the membrane-proximal stem. F10 binding occurs exclusively in this region (FIG. 6), making intimate contacts with the fusion peptide, elements of HA1 and HA2 (both of which are integral to the structure of this region) that lock the peptide into place in the neutral pH conformation, as well as the large helical hairpin of HA2 that undergoes a massive conformation change at acidic pH in order to propel the fusion peptide from its viral membrane-proximal pocket to the distal surface of the virus, where it can trigger fusion with the endosomal membrane.

The heavy chain of F10 plays the major role in H5 binding, utilizing the tips of its three complementarity-determining regions (CDRs). Each F10 molecule make contacts with both the HA1 and HA2 subunits within a single monomer of the HA trimer (FIG. 6). The contact region comprises a pocket formed by part of the HA2 fusion peptide, with elements of HA1 on one side and an exposed face of helix αA of HA2 on the other (FIG. 6). A triad of antibody residues—F55 and M54 from CDR H2, and Y102 from CDR H3—form major contact points. The phenyl ring of F55 lies across a flat surface formed by a prominent loop of the fusion peptide loop (HA2 residues DGW $19_2$-$21_2$ (H3 numbering scheme; subscripts 1 and 2 refer to HA1 and HA2 chains)) and the aromatic side-chains of two flanking histidines (residues $18_1$ and $38_1$) and a tryptophan, $W21_2$, which forms the back of the pocket. The side-chain of M54 also contacts the aromatic rings of $W21_2$ and $H38_1$, as well as the side-chain of $I45_2$ from helix αA, while its main-chain carbonyl oxygen hydrogen-bonds with the side-chain of $H38_1$. Y102 inserts its side-chain into a hydrophobic crevice created by four side-chains of the αA helix, and also hydrogen-bonds to a backbone carbonyl ($D19_2$) of the fusion peptide. The CDR H1 loop makes multiple contacts with the C-terminal end of helix αA and a loop of HA1 at the base of the head region (FIG. 6).

In parallel, mutagenesis experiments were carried out on helix αA to help define the epitope (FIG. 6). Mutations in 3 residues that directly contact the antibody: V52A/E, N53A and I56A, significantly reduced or ablated antibody binding, while the conservative mutation, V52L, had no effect. As controls, mutations on a different exposed face of the helix, which does not contact the antibody, had no effect on antibody binding. Thus, mutagenesis of the αA helix is fully consistent with the epitope defined crystallographically for F10. Furthermore, the other two nAbs, for which no structural data exist, showed an almost identical mutant-nAb binding profile, indicative of a closely overlapping epitope and consistent with competitive binding (FIG. 6, FIG. 9). Taken together, we conclude that all three nAbs neutralize virus by stabilizing the neutral pH conformation of HA in a region that provides the trigger (most likely release of the fusion peptide from its pocket) for conformational changes that lead to the fusogenic state.

Example 10: Structural Basis of Broad-Spectrum Neutralization

The region of HA defined by the F10 epitope is highly conserved among the 16 HA subtypes (FIG. 6 and Table 5). The fusion peptide must adopt a well-defined structure, both in the neutral pH conformation and during the process of membrane fusion, and mutagenesis studies have shown that few sequence changes are tolerated. The exposed helical face of HA2 αA is also nearly invariant across both groups, presumably because it must reorganize to form the inner surface of the long trimeric coiled-coil in the fusogenic state. Thus, the requirement of these segments to adopt two very different structures in two distinct environments presumably imparts strong evolutionary constraints on the sequences, providing a clear rationale for their conservation across the 16 HA subtypes.

Crystal structures have been determined for subtypes H1, H5, and H9 from Group 1 and H3 and H7 from Group 2, and the structures fall into two distinct classes, coincident with the two groups defined by phylogenetic analysis. Further comparisons show that the two classes are also readily distinguishable at the detailed 3-dimensional level within the region defined by the F10 epitope. Sequence differences in a few key amino acids buried in the core that are characteristic of each class (e.g. at $17_1$ and $111_2$) lead to consistent differences in the orientation of several side-chains within the epitope, as well as the disposition of the pocket with respect to helix αA.

Figure 6A:
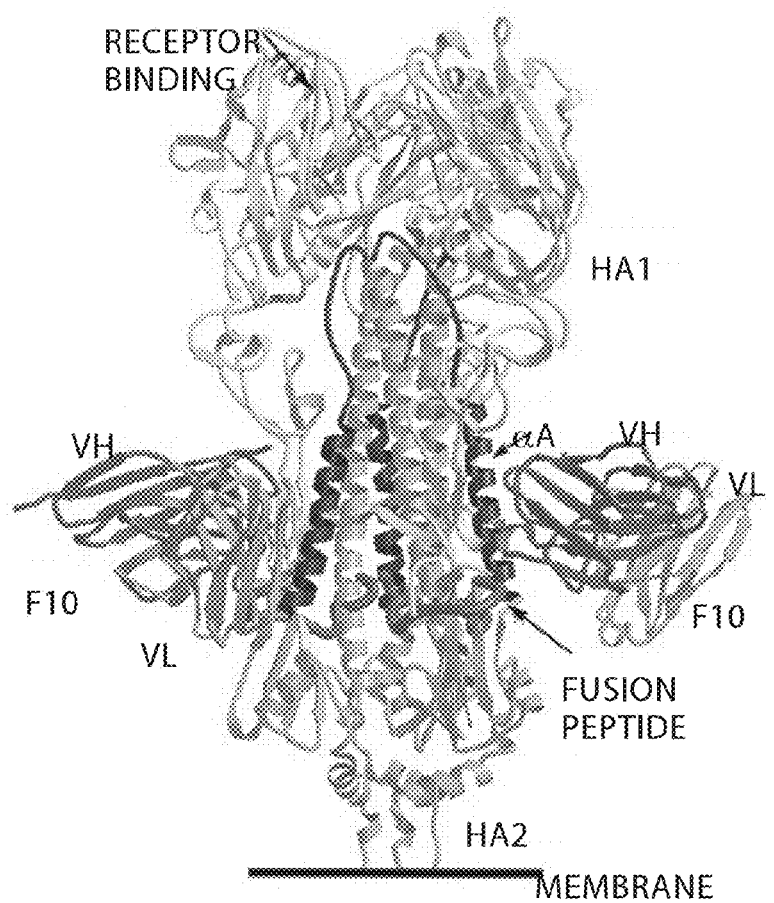
FIGS. 6A-6D show the structure of the H5-F10 epitope, and sequence/structural conservation. (a) Structure of the H5 trimer bound to F10 (scFv). H5 is very similar to the uncomplexed structure[21] (pairwise RMSD (Cα)=1.0 and 0.63 Å for 2 independent trimers). HA1, HA2, the αA-helix of HA2, the "fusion peptide" (FP), and F10 (VH and VL) are colour-coded. The third F10 is hidden behind the stem. Note that VL makes no contacts with H5. (b) Surface of the central stem region. One monomer is coloured by chain; the path of FP through the epitope (red) is outlined; mutations not affecting binding are in cyan. The fusion peptide (FP and FP') is visible in two monomers. Epitope residues are labeled white (HA2) or yellow (HA1). (c) Close-up of the epitope showing the tip of F10 (red ribbon) and selected CDR side-chains. Of 1500 Å² buried surface at the interface, 43% involves hydrophobic interactions. (d) Overlay of HA subtypes: H1, H5 and H9 (Group 1) in shades of red/yellow (1RU7, 2IBX and 1JSD); H3 and H7 (Group 2) in shades of blue (1MQL and 1TI8). RMSDs for pairwise overlays are 0.56±0.11 Å (observed range, Group 1); 0.75 Å (Group 2); and 1.21±0.12 Å between groups. Consistent differences between groups include the orientation of $W21_2$, which is linked to alternate side-chain directions at $18_1$ and $38_1$, the burial of the larger tyrosine (Group 1) versus histidine (Group 2) at $17_1$, and the packing of buried $His111_2$ (Group 1) against $W21_1$. Other epitope residues are indicated by numbered white circles. $N38_1$ is glycosylated in H3 and the H7 cluster. (e) Sequences of the 16 HA subtypes. Circles indicate calculated binding energies: strong=blue, intermediate=orange; weak=blue; unfavorable=black. Coloured highlighting indicates sequence conservation within clusters and groups. The network of inter-helical contacts that stabilize the fusogenic structure[29] are indicated below the sequences.
Figure 6B:
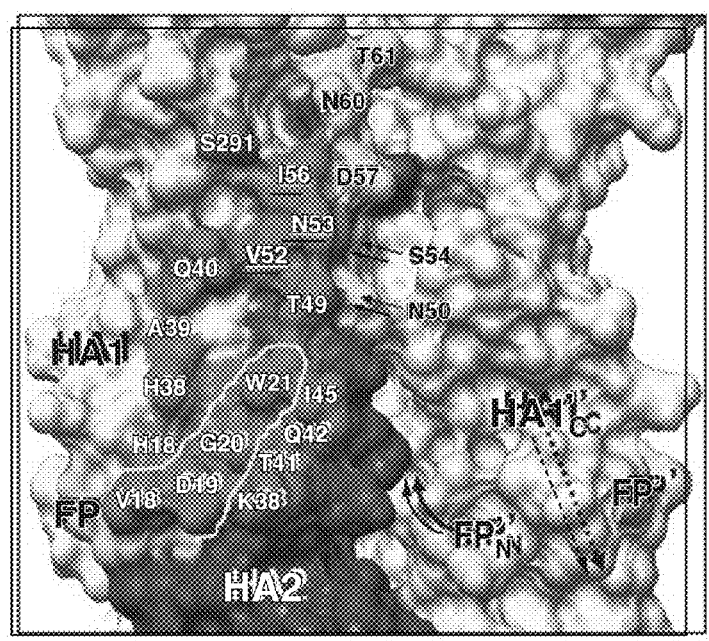
Figure 6C:
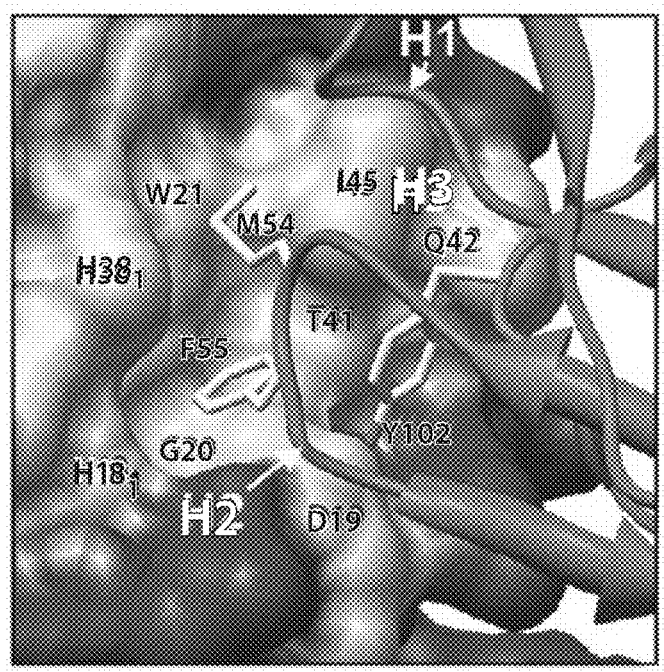
Figure 6D:
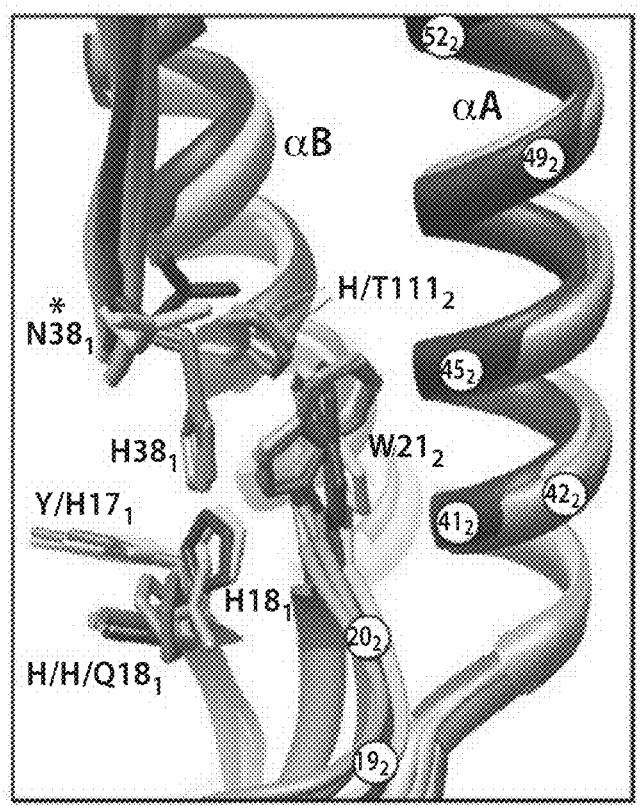
Figure 6E:
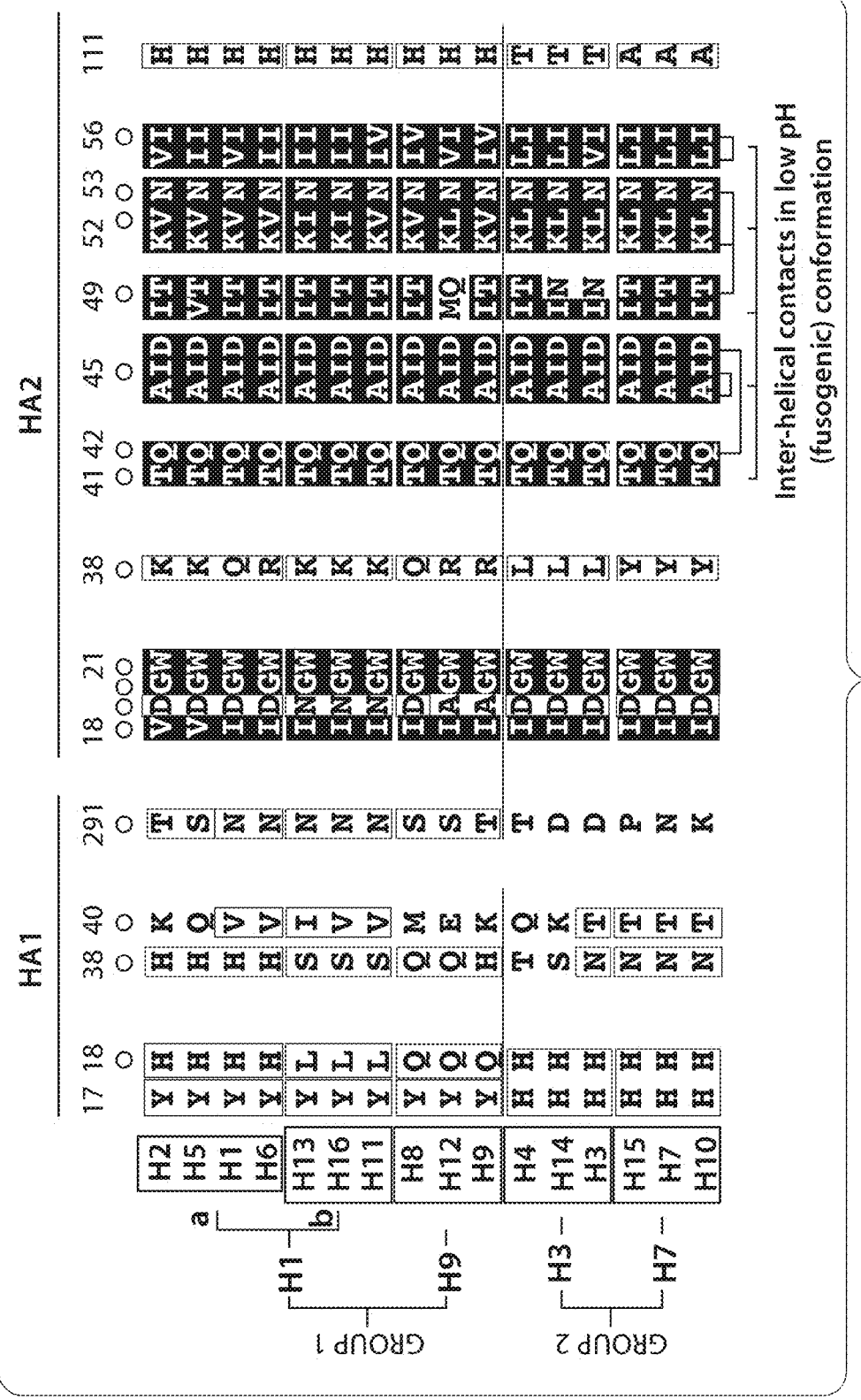
FIG. 6E discloses "VDGW" as SEQ ID NO: 108, "IDGW" as SEQ ID NO: 106, "INGW" as SEQ ID NO: 105, and "IAGW" as SEQ ID NO: 109.

Within each group/class, the epitope region is highly conserved, with very few differences in a given cluster, and only a few changes, generally conservative, between clusters (e.g., at positions $18_1$ and $38_1$, FIG. 6D). Our observation that the 3 nAbs can recognize all 4 members of the H1 cluster demonstrates that amino-acid differences at the periphery of the epitope (such as at residue $40_1$, which is K, Q or V in this cluster) may not be critical for binding.

The 10 antibodies we selected have 5 different sets of VH CDR1-3, which vary substantially in sequence and length. Nevertheless, the three key residues in CDR2 (M54, F55) and CDR3 (Y102) that insert into the pocket are conserved. The conservation of key residues within a varied CDR context may expand the range of HA subtype/cluster recognition by this group of nAbs beyond those tested here. However, it should be noted that 4 out of 6 Group 2 subtypes are glycosylated at position 38₁, which lies at the periphery of the F10 epitope. Modeling studies predict steric clashes (but only with the CDR H1 loop), which likely contributes to the observed lack of binding/neutralization of H7 viruses.

Example 11: Anti-H5 nAbs Bind to a Broad Range of Group 1 HA Subtypes

Figure 13:
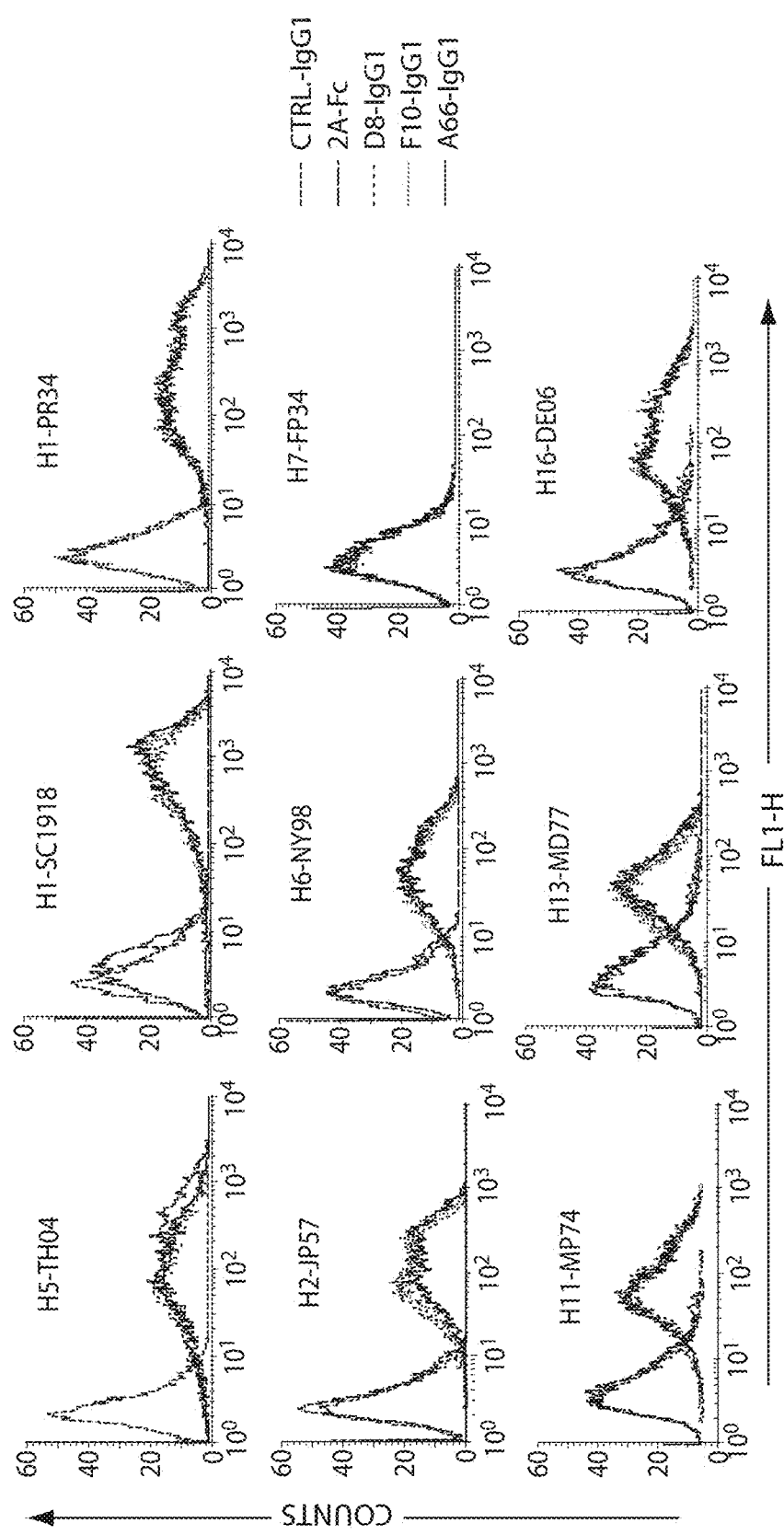
FIG. 13 shows FACS analysis of anti-H5 nAbs binding to all H1 Cluster HAs including H1, H2, H5, H6, H11, H13 and H16. 293T cells were transiently transfected with different HA-expressing plasmids, and mAb binding to the HA-expressing cells was analyzed by FACS. The anti-SARS mAb 80R was used as a control. 2A-Fc is an H5 HA specific antibody. Lack of binding to a Group 2 HA, H7, was also shown. Viral strain details of H11, H13 and H16 are: H11-MP74 (A/Duck/memphis/546/74 (H11N9)), H13-MD77 (A/Gull/MD/704/77 (H13N6)) and H16-DE06 (A/Shorebird/DE/172/06 (H16N3)).

Group 1 viruses contains 10 of the total 16 subtypes of Influenza A virus, and is further classified into 3 "clusters", H1a, H1b, and H9. We tested our nAbs for binding to all seven HA subtypes of Clusters H1a and H1b, which include avian H5 as well as the most common human influenza subtypes, with the exception of the Group 2 subtype, H3. In addition to H5, we found that all three nAb IgG1s bound to cells expressing full-length H1 from 2 different strains of H1N1, including the 1918 "Spanish flu"; H2 from H2N2; and H6 from H6N2; as well as the Cluster 1b subtypes: H11 from H11N9; H13 from H13N6; and H16 from H16N3. However, none of them bound to a Group 2 subtype, H7 from H7N1 (FIG. 13). More details about FIG. 13 are as follows. FACS analysis of anti-H5 nAbs binding to H1, H2, H5, H6 (cluster H1a) and H11, H13 and H16 (Cluster H1b). 293T cells were transiently transfected with different HA-expressing plasmids. NAb binding to the cells was analyzed by FACS. H5-specific antibody 2A and 80R are negative control. Lack of binding to a Group 2 HA, H7, is also shown. Detail on viral strains are: H1-SC1918 ((A/South Carolina/1/1918 (H1N1)), H1-PR34 (A/Puerto Rico/8/34 (H1N1)), H2-JP57 (A/Japan/305/57 (H2N2)), H5-TH04 (A/Thailand/2-SP-33/2004 (H5N1)), H6-NY98 (A/Chicken/New York/14677-13/1998 (H6N2)), H7-FP34 (A/FPV/Rostock/34 (H7N1)), H11-MP74 (A/Duck/memphis/546/74 (H11N9)), H13-MD77 (A/Gull/MD/704/77 (H13N6)) and H16-DE06 (A/Shorebird/DE/172/06 (H16N3)).

REFERENCES

1. W.H.O. http://www.who1.int/mediacentre/factsheets/2003/fs211/en/. World Health Organization factsheet 211: influenza (2003).
2. Webster, R. G. 1918 Spanish influenza: the secrets remain elusive. Proc Natl Acad Sci USA 96, 1164-6 (1999).
3. de Wit, E. & Fouchier, R. A. Emerging influenza. J Clin Virol 41, 1-6 (2008).
4. Wright, P., Neumann, G. & Kawaoka, Y. in Fields Virology (eds. Knipe, D., Howley, P., Griffin, D., Lamb, R. & Martin, M.) 1692-1740 (Lippincott Williams & Wilkins 2006).
5. Fauci, A. S. Pandemic influenza threat and preparedness. Emerg Infect Dis 12, 73-7 (2006).
6. Fouchier, R. A. et al. Characterization of a novel influenza A virus hemagglutinin subtype (H16) obtained from black-headed gulls. J Virol 79, 2814-22 (2005).
7. Ha, Y., Stevens, D. J., Skehel, J. J. & Wiley, D. C. H5 avian and H9 swine influenza virus haemagglutinin structures: possible origin of influenza subtypes. Embo J 21, 865-75 (2002).
8. Russell, R. J. et al. H1 and H7 influenza haemagglutinin structures extend a structural classification of haemagglutinin subtypes. Virology 325, 287-96 (2004).
9. W.H.O. (http://www.who.int/csr/disease/avian_influenza/guidelines/summaryH520070403.pdf, 2007).
10. W.H.O. Evolution of H5N1 avian influenza viruses in Asia. Emerg Infect Dis 11, 1515-21 (2005).
11. Subbarao, K. et al. Characterization of an avian influenza A (H5N1) virus isolated from a child with a fatal respiratory illness. Science 279, 393-6 (1998).
12. de Jong, J. C., Claas, E. C., Osterhaus, A. D., Webster, R. G. & Lim, W. L. A pandemic warning? Nature 389, 554 (1997).
13. W.H.O. http://www.who.int/csr/disease/avian_influenza/en/. (2008).
14. Nicholson, K. G. et al. Safety and antigenicity of non-adjuvanted and MF59-adjuvanted influenza A/Duck/Singapore/97 (H5N3) vaccine: a randomised trial of two potential vaccines against H5N1 influenza. Lancet 357, 1937-43 (2001).
15. Stephenson, I. et al. Cross-reactivity to highly pathogenic avian influenza H5N1 viruses after vaccination with nonadjuvanted and MF59-adjuvanted influenza A/Duck/Singapore/97 (H5N3) vaccine: a potential priming strategy. J Infect Dis 191, 1210-5 (2005).
16. Stephenson, I. et al. Boosting immunity to influenza H5N1 with MF59-adjuvanted H5N3 A/Duck/Singapore/97 vaccine in a primed human population. Vaccine 21, 1687-93 (2003).
17. Treanor, J. J., Campbell, J. D., Zangwill, K. M., Rowe, T. & Wolff, M. Safety and immunogenicity of an inactivated subvirion influenza A (H5N1) vaccine. N Engl J Med 354, 1343-51 (2006).
18. Treanor, J. J. et al. Safety and immunogenicity of a recombinant hemagglutinin vaccine for H5 influenza in humans. Vaccine 19, 1732-7 (2001).
19. Bresson, J. L. et al. Safety and immunogenicity of an inactivated split-virion influenza A/Vietnam/1194/2004 (H5N1) vaccine: phase I randomised trial. Lancet 367, 1657-64 (2006).
20. Lin, J. et al. Safety and immunogenicity of an inactivated adjuvanted whole-virion influenza A (H5N1) vaccine: a phase I randomised controlled trial. Lancet 368, 991-7 (2006).
21. W.H.O. http://www.who.int/csr/disease/influenza/influenzanetwork/en/index/html. (2008).
22. Carrat, F. & Flahault, A. Influenza vaccine: the challenge of antigenic drift. Vaccine 25, 6852-62 (2007).
23. Cinatl, J., Jr., Michaelis, M. & Doerr, H. W. The threat of avian influenza A (H5N1). Part IV: Development of vaccines. Med Microbiol Immunol 196, 213-25 (2007).
24. Subbarao, K. & Luke, C. H5N1 viruses and vaccines. PLoS Pathog 3, e40 (2007).
25. Leroux-Roels, I. et al. Broad Clade 2 Cross-Reactive Immunity Induced by an Adjuvanted Clade 1 rH5N1 Pandemic Influenza Vaccine. PLoS ONE 3, e1665 (2008).
26. Baras, B. et al. Cross-Protection against Lethal H5N1 Challenge in Ferrets with an Adjuvanted Pandemic Influenza Vaccine. PLoS ONE 3, e1401 (2008).
27. Marasco, W. A. & Sui, J. The growth and potential of human antiviral monoclonal antibody therapeutics. Nat Biotechnol 25, 1421-34 (2007).
28. Stevens, J. et al. Structure and receptor specificity of the hemagglutinin from an H5N1 influenza virus. Science 312, 404-10 (2006).
29. Sui, J. et al. Potent neutralization of severe acute respiratory syndrome (SARS) coronavirus by a human mAb to 51 protein that blocks receptor association. Proc Natl Acad Sci USA 101, 2536-41 (2004).
30. Huang, C. C. et al. Structural basis of tyrosine sulfation and VH-gene usage in antibodies that recognize the HIV type 1 coreceptor-binding site on gp120. Proc Natl Acad Sci USA 101, 2706-11 (2004).

31. Skehel, J. J. & Wiley, D. C. Receptor binding and membrane fusion in virus entry: the influenza hemagglutinin. Annu Rev Biochem 69, 531-69 (2000).
32. Kida, H., Yoden, S., Kuwabara, M. & Yanagawa, R. Interference with a conformational change in the haemagglutinin molecule of influenza virus by antibodies as a possible neutralization mechanism. Vaccine 3, 219-22 (1985).
33. Vanlandschoot, P. et al. An antibody which binds to the membrane-proximal end of influenza virus haemagglutinin (H3 subtype) inhibits the low-pH-induced conformational change and cell-cell fusion but does not neutralize virus. J Gen Virol 79 (Pt 7), 1781-91 (1998).
34. Su, Y., Zhu, X., Wang, Y., Mu, M. & Tien, P. Evaluation of Glu11 and Gly8 of the H5N1 influenza hemagglutinin fusion peptide in membrane fusion using pseudotype virus and reverse genetics. Acta Virol 153, 247-257 (2008).
35. Yamada, S. et al. Haemagglutinin mutations responsible for the binding of H5N1 influenza A viruses to human-type receptors. Nature 444, 378-82 (2006).
36. Stevens, J. et al. Structure of the uncleaved human H1 hemagglutinin from the extinct 1918 influenza virus. Science 303, 1866-70 (2004).
37. Daniels, R. S. et al. Fusion mutants of the influenza virus hemagglutinin glycoprotein. Cell 40, 431-9 (1985).
38. Thoennes, S. et al. Analysis of residues near the fusion peptide in the influenza hemagglutinin structure for roles in triggering membrane fusion. Virology 370, 403-14 (2008).
39. Earp, L. J., Delos, S. E., Park, H. E. & White, J. M. The many mechanisms of viral membrane fusion proteins. Curr Top Microbiol Immunol 285, 25-66 (2005).
40. Godley, L. et al. Introduction of intersubunit disulfide bonds in the membrane-distal region of the influenza hemagglutinin abolishes membrane fusion activity. Cell 68, 635-45 (1992).
41. Bullough, P. A., Hughson, F. M., Skehel, J. J. & Wiley, D. C. Structure of influenza haemagglutinin at the pH of membrane fusion. Nature 371, 37-43 (1994).
42. Ha, Y., Stevens, D. J., Skehel, J. J. & Wiley, D. C. X-ray structures of H5 avian and H9 swine influenza virus hemagglutinins bound to avian and human receptor analogs. Proc Natl Acad Sci USA 98, 11181-6 (2001).
43. Wilson, I. A., Skehel, J. J. & Wiley, D. C. Structure of the haemagglutinin membrane glycoprotein of influenza virus at 3 A resolution. Nature 289, 366-73 (1981).
44. Kashyap, A. K. et al. Combinatorial antibody libraries from survivors of the Turkish H5N1 avian influenza outbreak reveal virus neutralization strategies. Proc Natl Acad Sci USA Early edition (2008).
45. Huang, I. C. et al. Influenza A virus neuraminidase limits viral superinfection. J Virol (2008).
46. Glaser, L. et al. A single amino acid substitution in 1918 influenza virus hemagglutinin changes receptor binding specificity. J Virol 79, 11533-6 (2005).
47. Naldini, L., Blomer, U., Gage, F. H., Trono, D. & Verma, I. M. Efficient transfer, integration, and sustained long-term expression of the transgene in adult rat brains injected with a lentiviral vector. Proc Natl Acad Sci USA 93, 11382-8 (1996).
48. Rowe, T. et al. Detection of antibody to avian influenza A (H5N1) virus in human serum by using a combination of serologic assays. J Clin Microbiol 37, 937-43 (1999).

TABLE 3

Contact residues at the H5-F10 interface

| | FRH1 | CDRH1 | | | | CDRH2 | | | CDRH3 | | | | |
|---|---|---|---|---|---|---|---|---|---|---|---|---|---|
| F10 | S25 | V27 | T28 | S30 | S31 | M54 | F55 | T57 | P100 | S101 | Y102 | I103 | S105 |
| HA1 | S291 | S291 | | Q40 | | 38 | H10 | | | | | | |
| | | M292 | | | | | H38 | | | | | | |
| HA2 | | I56 | V52 | | I45 | W21 | V18 | V18 | Q42 | Q42 | D19 | D19 | K38 |
| | | | N53 | | T49 | I45 | D19 | | | | K3 | K38 | |
| | | | | | | | G20 | | | | T41 | | |
| | | | | | | | W21 | | | | Q42 | | |
| | | | | | | | | | | | I45 | | |

Contact residues defined by having a closest interatomic distance of <4.5 Å. The color scheme indicates contributions of individual residues to the binding free energy: very favorable (red(V27, T28, I45, D19, W21)), favorable (orange(S25, S291, M292, I56, V52, N53, T49, H18, V18, G20, T57, T41)), negligible (blue (S30, S31, Q40, H38), unfavorable (black), very unfavorable (bold black). Based on energy calculations using the server at http://structure.pitt.edu/servers/fastcontact¹.

TABLE 4

Data collection and refinement statistics.

| | H5-F10 |
|---|---|
| Data Collection | |
| Cell parameters | a = 205.3, b = 118.5, |
| | c = 338.9 |
| | β = 99.6° |
| Space group | C2 |
| Resolution (Å)* | 3.2 (3.28-3.20) |
| Total reflections | 509705 |
| Unique reflections | 112570 |
| Completeness (%)* | 85.0 (68.4) |
| Average I/σ(I)* | 9.5 (2.0) |
| $R_{MERGE}$ (%)* | 12.8 (81.0) |
| Redundancy* | 4.5 (4.5) |
| σ cutoff | −3 |
| Refinement | |
| Resolution | 50-3.2 (3.28-3.20) |
| $R_{WORK}$* | 0.23 (0.32) |
| $R_{FREE}$ (5% data)* | 0.29 (0.38) |
| RMSD bond distance (Å) | 0.01 |
| RMSD bond angle (°) | 1.31 |
| Average B value | 75.7 |
| Solvent atoms | 0 |
| σ cutoff | none |

TABLE 4-continued

Data collection and refinement statistics.

|  | H5-F10 |
|---|---|
| Ramachandran plot | |
| Residues in favored regions (%) | 90.0 |
| Residues in allowed regions (%) | 9.5 |
| Residues in outlier regions (%) | 0.5 |

*Numbers in parentheses correspond to the highest resolution shell.

TABLE 5*

Sequence comparison of F10 epitope among 16 HA subtypes.

| Group | Cluster | Subtype | # Full-length sequence | # Unique sequence | HA1 17 | 18 | 38 | 40 | 291 | HA2 18 |
|---|---|---|---|---|---|---|---|---|---|---|
| Group 1 | H1a | H2 | 100 | 95 | Y | H | H | (Q, E)/K (18)/77 | T | (I)/V (20)/75 |
| | | H5 | 1620 | 1178 | (S, T, F)/Y (4)/1174 | (Y, M)/H (2)/1176 | (Q, Y)/H (4)/1174 | (K)/Q (2)/1176 | (I, N, T, R)/S (6)/1172 | (I)/V (6)/1172 |
| | | H1 | 1211 | 701 | Y | H | H | (I)V (2)/699 | (S)/N (16)685 | (V, M)/I (137)/546 |
| | | H6 | 278 | 230 | Y | H | H | V | (I)N (1)229 | (V)/I (43)/187 |
| | H1b | H13 | 16 | 16 | Y | L | S | (V)/I (6)/16 | N | I |
| | | H16 | 8 | 6 | Y | L | S | (I)/V (2)/6 | N | I |
| | | H11 | 64 | 64 | Y | L | S | (I)/V (1)/64 | (T)/S (1)/63 | (L)/I (1)/63 |
| | H9 | H8 | 10 | 10 | Y | Q | Q | M | S | I |
| | | H12 | 19 | 18 | Y | Q | Q | E | S | V |
| | | H9 | 252 | 234 | (H)/Y (33)/201 | (L)/Q (1)/233 | (D)/H (1)/233 | (R, E)/K (5)/229 | (I)/T (1)/233 | V |
| Group 2 | H3 | H4 | 105 | 90 | H | H | (A)/T (1)/89 | (R)/Q (1)/89 | (A, I, S, N)/T (10)/82 | I |
| | | H14 | 2 | 2 | H | H | S | K | D | I |
| | | H3 | 2302 | 1228 | H | H | N | (N)/T (1)/1227 | (H, Y, E, G)/D (35)/1193 | (M)/(V/I) (149)/(70%/30) |
| | H7 | H15 | 8 | 5 | H | H | N | T | P | I |
| | | H7 | 334 | 273 | H | H | N | T | (S, R, P)/N (131)/142 | (V)/I (41)232 |
| | | H10 | 31 | 28 | H | H | N | T | (E)/K (1)/27 | V |

| Group | Cluster | Subtype | HA2 19 | 20 | 21 | 38 | 41 | 42 | 45 |
|---|---|---|---|---|---|---|---|---|---|
| Group 1 | H1a | H2 | D | G | W | K | T | Q | (F, V)/I (39)/56 |
| | | H5 | (N, H, Y, X)/D (5)/1173 | G | (R)/W (1)/1177 | (Q, R, N)/K (23)/1155 | (S)/T (3)/1175 | P/Q (1)/1177 | (M, L, T)/I (8)/1170 |
| | | H1 | D | G | W | (K, R, L)/Q (60)/641 | T | Q | (V)/I (2)/699 |
| | | H6 | D | G | (R)/W (1)/229 | (R)/K (102)/128 | T | Q | (V)/I (78)/152 |
| | H1b | H13 | N | G | W | K | T | Q | I |
| | | H16 | N | G | W | K | T | Q | I |
| | | H11 | N | G | W | (R)/K (5)/59 | T | Q | (V)/I (3)/61 |
| | H9 | H8 | D | G | W | Q | T | Q | I |
| | | H12 | A | G | W | R | T | Q | I |
| | | H9 | (S)/A (1)/233 | G | (G)/W (1)/233 | (K, G)/R (14)/220 | T | Q | (V, F, M, R)/I (43)/191 |
| Group 2 | H3 | H4 | D | G | (G)/W (1)/91 | L | T | Q | I |
| | | H14 | D | G | W | L | T | Q | I |
| | | H3 | (N)/D (15)/1213 | G | W | (F)/L (1)/1227 | T | Q | (V, T, L)/I (5)/1223 |
| | H7 | H15 | D | G | W | Y | T | Q | I |
| | | H7 | (N)/D (57)/213 | G | W | (H)/Y (1)/272 | T | (P)/Q (2)/271 | (V)/I (3)/270 |
| | | H10 | (N, E)/D (2)/26 | (A)/G (1)/27 | W | Y | T | Q | I |

TABLE 5*-continued

Sequence comparison of F10 epitope among 16 HA subtypes.

| Group | Cluster | Subtype | HA2 | | | | |
|---|---|---|---|---|---|---|---|
| | | | 49 | 52 | 53 | 56 | 111 |
| Group 1 | H1a | H2 | T | (I)/V (1)/94 | N | I | H |
| | | H5 | (I)/T (1)/1177 | V | N | (F)/V (1)/1177 | H |
| | | H1 | (S, N, X)/T (19)/682 | (M, I)/V (2)/699 | N | (V)/I (1)/700 | H |
| | | H6 | (I)/T (1)/229 | (I)/V (3)/227 | N | I | H |
| | H1b | H13 | T | V | N | I | H |
| | | H16 | T | V | N | I | H |
| | | H11 | (I)/T (1)/63 | V | N | (I, A)/V (17)/47 | H |
| | H9 | H8 | T | (I)/V (1)/9 | N | I | H |
| | | H12 | Q | L | N | I | H |
| | | H9 | (I)/T (1)/233 | V | (S, T, D)/N (3)/231 | (I)/V (55)/179 | (C)/H 1/233 |
| Group 2 | H3 | H4 | (N)/T (2)/89 | L | N | I | (A)/T (2)/90 |
| | | H14 | N | L | N | I | T |
| | | H3 | (D, S, T, A)/N (22)/1206 | (M)/L (1)/1227 | (D)/N (1)/1227 | (V, T, F)/I (19)/1209 | (A)/T (7)/1221 |
| | H7 | H15 | T | L | N | I | A |
| | | H7 | T | L | N | I | (T)/A (35)/238 |
| | | H10 | T | L | N | (V)/I (1)/27 | A |

*This table represents sequences available in public influenza sequence databases (http://www.ncbi.nlm.nih.gov/genomes/FLU/FLU.html) as of Apr. 17, 2008. Light blue highlights: top '( )/', (amino acid variant(s))/amino acid consensus at the position; bottom '( )/', (number of amino acid variants)/number of consensus amino acids. Non-highlighted amino acids are '100% conserved or variants are observed ≤5 times at those positions for subtypes H4, H6, H9, H10, H11. Histidines H17 (HA1) and H111 (HA2) that may play a role in pH-trigger are highlighted in green. Table 5 discloses "INGW" as SEQ ID NO: 105, "IDGW" as SEQ ID NO: 106, and "VAGW" as SEQ ID NO: 107.

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. Other aspects, advantages, and modifications considered to be within the scope of the following claims. The claims presented are representative of the inventions disclosed herein. Other, unclaimed inventions are also contemplated. Applicants reserve the right to pursue such inventions in later claim.

We claim:

1. A fully human or humanized monoclonal antibody, or scFv fragment thereof, wherein the fully human or humanized monoclonal antibody or scFv fragment thereof, binds to the stem region of the HA protein of an influenza A virus and comprises (a) a heavy chain with a CDR1 comprising amino acid sequence EVTFSSFA (SEQ ID NO: 120);

(b) a heavy chain with a CDR2 comprising amino acid sequence ISPNIFGTP (SEQ ID NO: 128);

(c) a heavy chain with a CDR3 comprising amino acid sequence ARSPSYICSGGTCVFDH (SEQ ID NO: 134);

(d) a light chain with a CDR1 comprising amino acid sequence SNNVGNQG (SEQ ID NO: 142);

(e) a light chain with a CDR2 comprising amino acid sequence RNN (SEQ ID NO: 152); and (f) a light chain with a CDR3 comprising amino acid sequence STWDSSLSAVV (SEQ ID NO: 162).

2. The monoclonal antibody or scFv fragment thereof of claim 1, wherein the monoclonal antibody, or scFv fragment thereof, comprises a heavy chain variable domain comprising amino acid sequence SEQ ID NO: 112, and a light chain variable domain comprising amino acid sequence SEQ ID NO: 20.

3. The monoclonal antibody, or scFv fragment thereof, of claim 1, wherein said monoclonal antibody, or scFv fragment thereof, stabilizes the neutral pH conformation of the HA protein.

4. The monoclonal antibody, or scFv fragment thereof, of claim 1, wherein said influenza A virus is an H1a cluster influenza virus or an H1b cluster influenza virus.

5. The monoclonal antibody, or scFv fragment thereof, of claim 1, wherein said influenza A virus is an H1, H2, H5, H6, or H11 subtype.

6. The monoclonal antibody, or scFv fragment thereof, of claim 1, wherein said monoclonal antibody, or scFv fragment thereof, inhibits viral and cell membrane fusion.

7. The monoclonal antibody, or scFv fragment thereof, of claim 1, wherein said monoclonal antibody, or scFv fragment thereof, binds to HA with a Kd value of 1 pm-200 mM.

8. The monoclonal antibody, or scFv fragment thereof, of claim 1, wherein said monoclonal antibody, or scFv fragment thereof, binds to HA with a Kd value of about 100-200 pM.

9. An isolated nucleic acid molecule encoding the recombinant monoclonal antibody, or scFv fragment thereof, of claim 1.

* * * * *

SEQUENCE LISTING

```
<160> NUMBER OF SEQ ID NOS: 172

<210> SEQ ID NO 1
<211> LENGTH: 369
<212> TYPE: DNA
<213> ORGANISM: Homo sapiens

<400> SEQUENCE: 1
caggtgcagc tggtgcagtc tggggctgag gtgaagaagc ctgggtcctc ggtgaaggtc        60
tcctgcaagg cttctggagg caccttcagt gacaatgcta tcagctgggt gcgacaggcc       120
ccaggacaag ggcttgagtg gatgggtggc atcattccta tctttggaaa accaaactac       180
gcacagaagt tccagggcag agtcacgatt actgcggacg aatccacgag cacagcctac       240
atggacctga ggagcctgag atctgaggac acggccgttt attactgtgc gagagattca       300
gacgcgtatt actatggttc gggggtatg gacgtctggg gccaaggcac cctggtcacc       360
gtctcctca                                                              369

<210> SEQ ID NO 2
```

```
<211> LENGTH: 123
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Asn
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Asp Leu Arg Ser Leu Arg Ser Glu Asp Thr Ala Val Tyr Tyr Cys
                85                  90                  95

Ala Arg Asp Ser Asp Ala Tyr Tyr Tyr Gly Ser Gly Met Asp Val
            100                 105                 110

Trp Gly Gln Gly Thr Leu Val Thr Val Ser Ser
        115                 120

<210> SEQ ID NO 3
<211> LENGTH: 335
<212> TYPE: DNA
<213> ORGANISM: Homo sapiens

<400> SEQUENCE: 3
ctgcctgtgc tgactcaatc atcctctgcc tctgcttccc tgggatcctc ggtcaagctc      60
acctgcactc tgagcagtgg gcatagtaac tacatcatcg catggcatca acagcagcca     120
gggaaggccc ctcggtactt gatgaaggtt aatagtgatg cagccacac caaggggac       180
gggatccctg atcgcttctc aggctccagc tctggggctg accgctacct caccatctcc     240
aacctccagt ctgaggatga ggctagttat ttctgtgaga cctgggacac taagattcat     300
gtcttcggaa ctgggaccaa ggtctccgtc ctcag                                335

<210> SEQ ID NO 4
<211> LENGTH: 111
<212> TYPE: PRT
<213> ORGANISM: Homo sapiens

<400> SEQUENCE: 4

Leu Pro Val Leu Thr Gln Ser Ser Ser Ala Ser Ala Ser Leu Gly Ser
1               5                   10                  15

Ser Val Lys Leu Thr Cys Thr Leu Ser Ser Gly His Ser Asn Tyr Ile
            20                  25                  30

Ile Ala Trp His Gln Gln Gln Pro Gly Lys Ala Pro Arg Tyr Leu Met
        35                  40                  45

Lys Val Asn Ser Asp Gly Ser His Thr Lys Gly Asp Gly Ile Pro Asp
    50                  55                  60

Arg Phe Ser Gly Ser Ser Ser Gly Ala Asp Arg Tyr Leu Thr Ile Ser
65                  70                  75                  80

Asn Leu Gln Ser Glu Asp Glu Ala Ser Tyr Phe Cys Glu Thr Trp Asp
                85                  90                  95

Thr Lys Ile His Val Phe Gly Thr Gly Thr Lys Val Ser Val Leu
            100                 105                 110
```

<210> SEQ ID NO 5
<211> LENGTH: 363
<212> TYPE: DNA
<213> ORGANISM: Homo sapiens

<400> SEQUENCE: 5

```
caggtgcagc tggtgcagtc tggggctgag gtgaagaagc ctgggtcctc ggtgaaggtc      60
tcctgcaagg ctcctggagg tatcttcaac accaatgctt tcagctgggt ccgacaggcc     120
cctggacaag gtcttgagtg gtgggaggg gtcatccctt tgtttcgaac agcaagctac     180
gcacagaacg tccagggcag agtcaccatt accgcggacg aatccacgaa cacagcctac     240
atggagctta ccagcctgag atctgcggac acggccgtgt attactgtgc gagaagtagt     300
ggttaccatt ttaggagtca ctttgactcc tggggcctgg aaccctggt caccgtctcc     360 tca                                                                   363
```

<210> SEQ ID NO 6
<211> LENGTH: 121
<212> TYPE: PRT
<213> ORGANISM: Homo sapiens

<400> SEQUENCE: 6

```
Gln Val Gln Leu Val Gln Ser Gly Ala Glu Val Lys Lys Pro Gly Ser
1               5                   10                  15

Ser Val Lys Val Ser Cys Lys Ala Pro Gly Gly Ile Phe Asn Thr Asn
            20                  25                  30

Ala Phe Ser Trp Val Arg Gln Ala Pro Gly Gln Gly Leu Glu Trp Val
        35                  40                  45

Gly Gly Val Ile Pro Leu Phe Arg Thr Ala Ser Tyr Ala Gln Asn Val
    50                  55                  60

Gln Gly Arg Val Thr Ile Thr Ala Asp Glu Ser Thr Asn Thr Ala Tyr
65                  70                  75                  80

Met Glu Leu Thr Ser Leu Arg Ser Ala Asp Thr Ala Val Tyr Tyr Cys
                85                  90                  95

Ala Arg Ser Ser Gly Tyr His Phe Arg Ser His Phe Asp Ser Trp Gly
            100                 105                 110

Leu Gly Thr Leu Val Thr Val Ser Ser
        115                 120
```

<210> SEQ ID NO 7
<211> LENGTH: 363
<212> TYPE: DNA
<213> ORGANISM: Homo sapiens

<400> SEQUENCE: 7

```
caggtgcagc tggtgcaatc tggggctgag gtgaagaagc ctgggtcctc ggtgaaggtc      60
tcctgcaagg ctcctggagg tatcttcaac accaatgctt tcagctgggt ccgacaggcc     120
cctggacaag gtcttgagtg gtgggaggg gtcatccctt tgtttcgaac agcaagctac     180
gcacagaacg tccagggcag agtcaccatt accgcggacg aatccacgaa cacagcctac     240
atggagctta ccagcctgag atctgcggac acggccgtgt attactgtgc gagaagtagt     300
ggttaccatt ttaggagtca ctttgactcc tggggcctgg aaccctggt caccgtctcc     360 tca                                                                   363
```

<210> SEQ ID NO 8
<211> LENGTH: 111

```
<212> TYPE: PRT
<213> ORGANISM: Homo sapiens

<400> SEQUENCE: 8

Asn Phe Met Leu Thr Gln Pro His Ser Val Ser Ala Ser Pro Gly Lys
1               5                   10                  15

Thr Val Thr Ile Ser Cys Thr Gly Ser Ser Gly Asn Ile Ala Ala Asn
            20                  25                  30

Tyr Val Gln Trp Tyr Gln Gln Arg Pro Gly Ser Ala Pro Thr Thr Val
        35                  40                  45

Ile Tyr Glu Asp Asp Arg Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Thr
                85                  90                  95

Asn Asn His Ala Val Phe Gly Gly Gly Thr His Leu Thr Val Leu
            100                 105                 110

<210> SEQ ID NO 9
<211> LENGTH: 333
<212> TYPE: DNA
<213> ORGANISM: Homo sapiens

<400> SEQUENCE: 9
aattttatgc tgactcagcc ccactctgtg tcggcgtctc cggggaagac ggtgaccatc      60
tcctgcaccg gcagcagtgg caacattgcc gccaactatg tgcagtggta ccaacaacgt    120
ccgggcagtg cccccactac tgtgatctat gaggatgacc gaagaccctc tggggtccct    180
gatcggttct ctggctccat cgacaggtcc tccaactctg cctccctcac catctcagga    240
ctgaagactg aggacgaggc tgactactac tgtcagactt atgataccaa caatcatgct    300
gtgttcggag gaggcaccca cctgaccgtc ctc                                 333

<210> SEQ ID NO 10
<211> LENGTH: 110
<212> TYPE: PRT
<213> ORGANISM: Homo sapiens

<400> SEQUENCE: 10

Ser Tyr Glu Leu Thr Gln Pro Pro Ser Ala Ser Gly Lys His Gly Gln
1               5                   10                  15

Arg Val Thr Ile Ser Cys Ser Gly Gly Thr Ser Asn Ile Gly Arg Asn
            20                  25                  30

His Val Asn Trp Tyr Gln Gln Leu Pro Gly Thr Ala Pro Lys Leu Leu
        35                  40                  45

Ile Tyr Ser Asn Glu Gln Arg Pro Ser Gly Val Pro Asp Arg Phe Ser
    50                  55                  60

Gly Ser Lys Ser Gly Thr Ser Ala Ser Leu Ala Val Ser Gly Leu Gln
65                  70                  75                  80

Ser Glu Asp Glu Ala Asp Tyr Tyr Cys Ala Ser Trp Asp Asp Asn Leu
                85                  90                  95

Ser Gly Trp Val Phe Gly Gly Gly Thr Lys Leu Thr Val Leu
            100                 105                 110

<210> SEQ ID NO 11
<211> LENGTH: 330
<212> TYPE: DNA
```

<213> ORGANISM: Homo sapiens

<400> SEQUENCE: 11

```
tcctatgagc tgactcagcc accctcagcg tctgggaaac acgggcagag ggtcaccatc    60
tcttgttctg gaggcacctc aacatcgga cgtaatcatg ttaactggta ccagcaactc   120
ccaggaacgg cccccaaact cctcatctat agtaatgaac agcggccctc agggtccct   180
gaccgattct ctggctccaa atctggcacc tccgcctccc tggccgtgag tgggctccag   240
tctgaggatg aggctgatta ttactgtgca tcatgggatg acaacttgag tggttgggtg   300
ttcggcggag ggaccaagct gaccgtccta                                    330
```

<210> SEQ ID NO 12
<211> LENGTH: 120
<212> TYPE: PRT
<213> ORGANISM: Homo sapiens

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Ala Phe Thr Trp Val Arg Gln Ala Pro Gly Gln Gly Leu Glu Trp Met
        35                  40                  45

Gly Gly Ile Thr Gly Met Phe Gly Thr Ala Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Thr Ser Glu Asp Thr Ala Leu Tyr Tyr Cys
                85                  90                  95

Ala Arg Gly Leu Tyr Tyr Tyr Glu Ser Ser Leu Asp Tyr Trp Gly Gln
            100                 105                 110

Gly Thr Leu Val Thr Val Ser Ser
        115                 120

<210> SEQ ID NO 13
<211> LENGTH: 361
<212> TYPE: DNA
<213> ORGANISM: Homo sapiens

<400> SEQUENCE: 13

```
caggtgcagc tggtgcagtc tggggctgag gtgaagaagc ctgggtcctc ggtgaaggtc    60
tcctgcaagg cttctggagg caccttcagc gcttatgctt tcacctgggt gcggcaggcc   120
cctggacaag gcttgagtg gatgggaggc atcaccggaa tgtttggcac agcaaactac   180
gcacagaagt tccagggcag agtcacgatt accgcggacg aactcacgag cacagcctac   240
atggagttga gctccctgac atctgaagac acggcccttt attattgtgc gagaggattg   300
tattactatg agagtagtct tgactattgg ggccaggaa ccctggtcac cgtctcctca   360
g                                                                  361
```

<210> SEQ ID NO 14
<211> LENGTH: 110
<212> TYPE: PRT
<213> ORGANISM: Homo sapiens

<400> SEQUENCE: 14

Gln Ser Val Leu Thr Gln Pro Pro Ser Ala Ser Gly Ser Pro Gly Gln

```
1               5                   10                  15
Ser Val Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
                35                  40                  45

Met Ile Tyr Glu Val Thr Lys Arg Pro Ser Gly Val Pro Asp Arg Phe
            50                  55                  60

Ser Ala Ser Lys Ser Gly Asn Thr Ala Ser Leu Thr Val Ser Gly Leu
65                  70                  75                  80

Gln Ala Glu Asp Glu Ala Asp Tyr Phe Cys Cys Ser Tyr Ala Gly His
                    85                  90                  95

Ser Ala Tyr Val Phe Gly Thr Gly Thr Lys Val Thr Val Leu
                100                 105                 110
```

<210> SEQ ID NO 15
<211> LENGTH: 361
<212> TYPE: DNA
<213> ORGANISM: Homo sapiens

<400> SEQUENCE: 15

```
caggtgcagc tggtgcagtc tggggctgag gtgaagaagc ctgggtcctc ggtgaaggtc      60
tcctgcaggg cttctggagg caccttcagc gcttatgctt tcacctgggt gcggcaggcc     120
cctggacaag gcttgagtg gatgggaggc atcaccggaa tgtttggcac agcaaactac     180
gcacagaagt tccagggcag agtcacgatt accgcggacg aactcacgag cacagcctac     240
atggagttga gctccctgac atctgaagac acggcccttt attattgtgc gagaggattg     300
tattactatg agagtagtct tgactattgg ggccagggaa ccctggtcac cgtctcctca     360
g                                                                    361
```

<210> SEQ ID NO 16
<211> LENGTH: 108
<212> TYPE: PRT
<213> ORGANISM: Homo sapiens

<400> SEQUENCE: 16

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Ser Ser Lys
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Ser Cys Gln Gln Tyr Asp Gly Val Pro
                85                  90                  95

Arg Thr Phe Gly Gln Gly Thr Thr Val Glu Ile Lys
                100                 105
```

<210> SEQ ID NO 17
<211> LENGTH: 330
<212> TYPE: DNA
<213> ORGANISM: Homo sapiens

<400> SEQUENCE: 17
cagtctgtgc tgactcagcc accctccgcg tccgggtctc ctggacagtc agtcaccatc    60
tcctgcactg gaaccagcag tgacgttggt ggttataact ctgtctcctg gtaccaacag   120
cacccaggca aagcccccaa actcatgatt tatgaggtca ctaagcggcc ctcaggggtc   180
cctgatcgct tctctgcctc caagtctggc aacacggcct ccctgaccgt ctctgggctc   240
caggctgagg atgaggctga ttatttctgc tgctcatatg caggccacag tgcttatgtc   300
ttcggaactg ggaccaaggt caccgtcctg                                    330

<210> SEQ ID NO 18
<211> LENGTH: 124
<212> TYPE: PRT
<213> ORGANISM: Homo sapiens

<400> SEQUENCE: 18

Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
            20                  25                  30

Ala Ile Ser Trp Val Arg Gln Ala Pro Gly Gln Gly Leu Glu Trp Leu
        35                  40                  45

Gly Gly Ile Ser Pro Met Phe Gly Thr Pro Asn Tyr Ala Gln Lys Phe
    50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
        115                 120

<210> SEQ ID NO 19
<211> LENGTH: 324
<212> TYPE: DNA
<213> ORGANISM: Homo sapiens

<400> SEQUENCE: 19
gaaattgtgc tgactcagtc tccaggcacc ctgtctttgt ctccagggga aagagccacc    60
ctctcctgca gggccagtca gagtcttagc agcaagtact tagcctggta tcagcagaaa   120
cctggccagg ctcccaggct cctcatctat ggtgcatcca gcagggccac tggcatccca   180
gacaggttca gtggcagtgg gtctgggaca gacttcaccc tcaccatcag tagactggag   240
cctgaagatt ttgcagtgta ttcctgtcag cagtatgatg gcgtacctcg gacgttcggc   300
caagggacca cggtggaaat caaa                                          324

<210> SEQ ID NO 20
<211> LENGTH: 110
<212> TYPE: PRT
<213> ORGANISM: Homo sapiens

<400> SEQUENCE: 20

Gln Pro Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu

```
                35                  40                  45
Ser Tyr Arg Asn Asn Asp Arg Pro Ser Gly Ile Ser Glu Arg Phe Ser
 50                  55                  60

Ala Ser Arg Ser Gly Asn Thr Ala Ser Leu Thr Ile Thr Gly Leu Gln
 65                  70                  75                  80

Pro Glu Asp Glu Ala Asp Tyr Tyr Cys Ser Thr Trp Asp Ser Ser Leu
                 85                  90                  95

Ser Ala Val Val Phe Gly Gly Gly Thr Lys Leu Thr Val Leu
                100                 105                 110

<210> SEQ ID NO 21
<211> LENGTH: 372
<212> TYPE: DNA
<213> ORGANISM: Homo sapiens

<400> SEQUENCE: 21
caggtgcagc tggtgcagtc aggggctgag gtgaagaagc ctgggtcctc ggtgaaggtc      60
tcctgcacgt cctctgaagt caccttcagt agttttgcta tcagctgggt gcgacaggcc    120
cctggacaag ggcttgagtg gctgggaggg atcagcccta tgtttggaac acctaattac    180
gcgcagaagt tccaaggcag agtcaccatt accgcggacc agtccacgag acagcctac     240 atggacctga ggagcctgag atctgaggac acggccgtgt attattgtgc gagatctcct    300
tcttacattt gttctggtgg aacctgcgtc tttgaccatt ggggccaggg aaccctggtc    360
accgtctcct ca                                                        372

<210> SEQ ID NO 22
<211> LENGTH: 107
<212> TYPE: PRT
<213> ORGANISM: Homo sapiens

<400> SEQUENCE: 22

Asp Ile Gln Met Thr Gln Ser Pro Ser Ser Leu Ser Ala Ser Val Gly
  1                5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
                 35                  40                  45

Tyr Ala Ala Ser Ser Leu Gln Arg Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Tyr Asp Ser Ser Pro Tyr
                 85                  90                  95

Thr Phe Gly Gln Gly Thr Lys Val Glu Ile Lys
                100                 105

<210> SEQ ID NO 23
<211> LENGTH: 372
<212> TYPE: DNA
<213> ORGANISM: Homo sapiens

<400> SEQUENCE: 23
caggtacagc tgcagcagtc aggggctgag gtgaagaagc ctgggtcctc ggtgaaggtc      60
tcctgcacgt cctctgaagt caccttcagt agttttgcta tcagctgggt gcgacaggcc    120
cctggacaag ggcttgagtg gctgggaggg atcagcccta tgtttggaac acctaattac    180
```

```
gcgcagaagt tccaaggcag agtcaccatt accgcggacc agtccacgag acagcctac      240 atggacctga ggagcctgag atctgaggac acggccgtgt attattgtgc gagatctcct     300
tcttacattt gttctggtgg aacctgcgtc tttgaccatt ggggccaggg aaccctggtc     360
accgtctcct ca                                                         372
```

<210> SEQ ID NO 24
<211> LENGTH: 122
<212> TYPE: PRT
<213> ORGANISM: Homo sapiens

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Thr Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Gly Val Phe Gly Val Pro Lys Tyr Ala Gln Asn Phe
    50                  55                  60

Gln Gly Arg Val Thr Ile Thr Ala Asp Lys Pro Thr Ser Thr Val Tyr
65                  70                  75                  80

Met Glu Leu Asn Ser Leu Arg Ala Glu Asp Thr Ala Val Tyr Tyr Cys
                85                  90                  95

Ala Arg Glu Pro Gly Tyr Tyr Val Gly Lys Asn Gly Phe Asp Val Trp
            100                 105                 110

Gly Gln Gly Thr Met Val Thr Val Ser Ser
        115                 120
```

<210> SEQ ID NO 25
<211> LENGTH: 330
<212> TYPE: DNA
<213> ORGANISM: Homo sapiens

<400> SEQUENCE: 25

```
cagcctgggc tgactcagcc accctcggtg tccaagggct tgagacagac cgccacactc     60
acctgcactg ggaacagcaa caatgttggc aaccaaggag cagcttggct gcagcagcac     120
cagggccacc ctcccaaact cctatcctac aggaataatg accggccctc agggatctca    180
gagagattct ctgcatccag gtcaggaaac acagcctccc tgaccattac tggactccag    240
cctgaggacg aggctgacta ttactgctca acatgggaca gcagcctcag tgctgtggta    300
ttcggcggag ggaccaagct gaccgtccta                                      330
```

<210> SEQ ID NO 26
<211> LENGTH: 110
<212> TYPE: PRT
<213> ORGANISM: Homo sapiens

<400> SEQUENCE: 26

```
Ser Tyr Glu Leu Thr Gln Pro Pro Ser Val Ser Lys Gly Leu Arg Gln
1               5                   10                  15

Thr Ala Ile Leu Thr Cys Thr Gly Asp Ser Asn Asn Val Gly His Gln
            20                  25                  30

Gly Thr Ala Trp Leu Gln Gln His Gln Gly His Pro Pro Lys Leu Leu
        35                  40                  45

Ser Tyr Arg Asn Gly Asn Arg Pro Ser Gly Ile Ser Glu Arg Phe Ser
    50                  55                  60
```

Ala Ser Arg Ser Gly Asn Thr Ala Ser Leu Thr Ile Ile Gly Leu Gln
65                  70                  75                  80

Pro Glu Asp Glu Ala Asp Tyr Tyr Cys Ser Val Trp Asp Ser Ser Leu
                85                  90                  95

Ser Ala Trp Val Phe Gly Gly Gly Thr Lys Leu Thr Val Leu
            100                 105                 110

<210> SEQ ID NO 27
<211> LENGTH: 321
<212> TYPE: DNA
<213> ORGANISM: Homo sapiens

<400> SEQUENCE: 27
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagagg gtcccatca   180 aggttcagtg gcagtggatc tgggacagac ttcactctca ccattagcag cctgcagcct   240
gaagattttg cagtgtatta ctgtcagcag tatgatagtt caccgtacac ttttggccag   300
gggaccaagg tagagatcaa a                                             321

<210> SEQ ID NO 28
<211> LENGTH: 126
<212> TYPE: PRT
<213> ORGANISM: Homo sapiens

<400> SEQUENCE: 28

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Met Thr Gly Gly Thr Asn Tyr Ala Gln Lys Phe
    50                  55                  60

Gln Val Trp Val Thr Met Thr Arg Asp Thr Ser Ile Asn Thr Ala Tyr
65                  70                  75                  80

Met Glu Val Ser Arg Leu Thr Ser Asp Asp Thr Ala Val Tyr Tyr Cys
                85                  90                  95

Ala Arg Gly Ala Ser Val Leu Arg Tyr Phe Asp Trp Gln Pro Glu Ala
            100                 105                 110

Leu Asp Ile Trp Gly Leu Gly Thr Thr Val Thr Val Ser Ser
        115                 120                 125

<210> SEQ ID NO 29
<211> LENGTH: 366
<212> TYPE: DNA
<213> ORGANISM: Homo sapiens

<400> SEQUENCE: 29
caggtgcagc tggtgcaatc tggggctgaa gtgaagaagc ctggggcctc agtgaaggtc    60
tcctgcaaga cttctggagt caccttcagc agctatgcta tcagttgggt gcgacaggcc   120
cctggacaag gcttgagtg gatgggaggg atcatcggtg tctttggtgt accaaagtac   180
gcgcagaact ccagggcag agtcacaatt accgcggaca aaccgacgag tacagtctac   240
atggagctga acagcctgag agctgaggac acggccgtgt attactgtgc gagagagccc   300

```
gggtactacg taggaaagaa tggttttgat gtctggggcc aagggacaat ggtcaccgtc    360
tcttca                                                               366

<210> SEQ ID NO 30
<211> LENGTH: 108
<212> TYPE: PRT
<213> ORGANISM: Homo sapiens

<400> SEQUENCE: 30

Gln Pro Val Leu Thr Gln Pro Ser Val Ser Val Ala Pro Gly Gln
1               5                   10                  15

Thr Ala Ser Ile Pro Cys Gly Gly Asn Asn Ile Gly Gly Tyr Ser Val
                20                  25                  30

His Trp Tyr Gln Gln Lys Pro Gly Gln Ala Pro Leu Leu Val Ile Tyr
            35                  40                  45

Asp Asp Lys Asp Arg Pro Ser Gly Ile Pro Glu Arg Phe Ser Gly Ala
        50                  55                  60

Asn Ser Gly Ser Thr Ala Thr Leu Thr Ile Ser Arg Val Glu Ala Gly
65                  70                  75                  80

Asp Glu Gly Asp Tyr Tyr Cys Gln Val Trp Asp Ser Gly Asn Asp Arg
                85                  90                  95

Pro Leu Phe Gly Gly Gly Thr Lys Leu Thr Val Leu
            100                 105

<210> SEQ ID NO 31
<211> LENGTH: 330
<212> TYPE: DNA
<213> ORGANISM: Homo sapiens

<400> SEQUENCE: 31
tcctatgagc tgactcagcc accctcggtg tccaagggct tgagacagac cgccatactc    60
acctgcactg gagacagcaa caatgttggc caccaaggta cagcttggct gcaacaacac   120
cagggccacc ctcccaaact cctatcctac aggaatggca accggccctc agggatctca   180
gagagattct ctgcatccag gtcaggaaat acagcctccc tgaccattat tggactccag   240
cctgaggacg aggctgacta ctactgctca gtatgggaca gcagcctcag tgcctgggtg   300
ttcggcggag ggaccaagct gaccgtccta                                    330

<210> SEQ ID NO 32
<211> LENGTH: 123
<212> TYPE: PRT
<213> ORGANISM: Homo sapiens

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Met Thr
                20                  25                  30

Ala Phe Thr Trp Leu Arg Gln Ala Pro Gly Gln Gly Leu Glu Trp Met
            35                  40                  45

Gly Gly Ile Ser Pro Ile Phe Arg Thr Pro Lys Tyr Ala Gln Lys Phe
        50                  55                  60

Gln Gly Arg Val Thr Ile Thr Ala Asp Glu Ser Thr Asn Thr Ala Asn
65                  70                  75                  80

Met Glu Leu Thr Ser Leu Lys Ser Glu Asp Thr Ala Val Tyr Tyr Cys
                85                  90                  95
```

Ala Arg Thr Leu Ser Ser Tyr Gln Pro Asn Asn Asp Ala Phe Ala Ile
            100                 105                 110

Trp Gly Gln Gly Thr Met Val Thr Val Ser Ser
        115                 120

<210> SEQ ID NO 33
<211> LENGTH: 378
<212> TYPE: DNA
<213> ORGANISM: Homo sapiens

<400> SEQUENCE: 33
caggtgcagc tggtgcagtc tggggctgag gtgaggaagc ctggggcctc agtgaaggtc      60
tcatgtaagg cttctggata caccttcacc ggttattata ttcactgggt gcgacaggcc     120
cctggacaag gacttgagtg gatgggttgg atcaaccctc tgactggtgg cacaaactat     180
gcacagaagt ttcaggtctg gtcaccatg acccgggaca cgtccatcaa cacagcctac      240
atggaggtga gcaggctgac atctgacgac acggccgtgt attactgtgc gagggggct      300 tccgtattac gatattttga ctggcagccc gaggctcttg atatctgggg cctcgggacc     360
acggtcaccg tctcctca                                                   378

<210> SEQ ID NO 34
<211> LENGTH: 106
<212> TYPE: PRT
<213> ORGANISM: Homo sapiens

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Phe Cys Gln Gln Tyr Gly Ser Ser Pro Gln
                85                  90                  95

Phe Gly Gln Gly Thr Arg Leu Glu Ile Lys
            100                 105

<210> SEQ ID NO 35
<211> LENGTH: 324
<212> TYPE: DNA
<213> ORGANISM: Homo sapiens

<400> SEQUENCE: 35
cagcctgtgc tgactcagcc accctcggtg tcagtggccc caggacagac ggccagcatt      60
ccctgtgggg gaaacaacat tggaggctac agtgtacact ggtaccaaca aaagccgggc     120
caggcccccc tcttggtcat ttatgacgat aaagaccggc cctcagggat ccctgagcga     180
ttctctggcg ccaactctgg gagcacggcc accctgacaa tcagcagggt cgaagccggg     240
gatgagggcg actactactg tcaggtgtgg gatagtggta atgatcgtcc gctgttcggc     300
ggagggacca agctgaccgt ccta                                             324

<210> SEQ ID NO 36
<211> LENGTH: 123
<212> TYPE: PRT
<213> ORGANISM: Homo sapiens

<400> SEQUENCE: 36

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Ser Met Thr
            20                  25                  30

Ala Phe Thr Trp Leu Arg Gln Ala Pro Gly Gln Gly Leu Glu Trp Met
        35                  40                  45

Gly Gly Ile Ser Pro Ile Phe Arg Thr Pro Lys Tyr Ala Gln Lys Phe
    50                  55                  60

Gln Gly Arg Val Thr Ile Thr Ala Asp Glu Ser Thr Asn Thr Ala Asn
65                  70                  75                  80

Met Glu Leu Thr Ser Leu Lys Ser Glu Asp Thr Ala Val Tyr Tyr Cys
                85                  90                  95

Ala Arg Thr Leu Ser Ser Tyr Gln Pro Asn Asn Asp Ala Phe Ala Ile
            100                 105                 110

Trp Gly Gln Gly Thr Met Val Thr Val Ser Ser
        115                 120
```

<210> SEQ ID NO 37
<211> LENGTH: 369
<212> TYPE: DNA
<213> ORGANISM: Homo sapiens

<400> SEQUENCE: 37

```
caggtgcagc tggtgcagtc tggggctgaa gtgaagaagc ctggctcctc ggtgaaggtt    60
tcctgcaagg cttctggagg ccccttcagc atgactgctt tcacctggct gcgacaggcc   120
cctggacaag gcttgagtg gatgggtggg atcagcccta tctttcgtac accgaagtac   180
gcacagaagt tccagggcag agtcacgatt accgcggacg aatccacgaa cacagccaac   240
atggagctga ccagcctgaa atctgaggac acggccgtgt attactgtgc gagaaccctt   300
tcctcctacc aaccgaataa tgatgctttt gctatctggg gccaagggac aatggtcacc   360
gtctcttca                                                           369
```

<210> SEQ ID NO 38
<211> LENGTH: 110
<212> TYPE: PRT
<213> ORGANISM: Homo sapiens

<400> SEQUENCE: 38

```
Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Arg Ser Gly Thr Ser Ala Ser Leu Ala Ile Ile Gly Leu Arg
65                  70                  75                  80

Pro Glu Asp Glu Ala Asp Tyr Tyr Cys Gln Ser Tyr Asp Ser Arg Leu
                85                  90                  95
```

Ser Ala Ser Leu Phe Gly Thr Gly Thr Thr Val Thr Val Leu
            100                 105                 110

<210> SEQ ID NO 39
<211> LENGTH: 318
<212> TYPE: DNA
<213> ORGANISM: Homo sapiens

<400> SEQUENCE: 39
gaaattgtgt tgacgcagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag actggagcct   240
gaagattttg cagtctattt ctgtcagcag tatggtagct cacctcaatt cggccaaggg   300
acacgactgg agattaaa                                                 318

<210> SEQ ID NO 40
<211> LENGTH: 369
<212> TYPE: DNA
<213> ORGANISM: Homo sapiens

<400> SEQUENCE: 40
caggtgcagc tggtgcagtc tggggctgaa gtgaagaagc ctggctcctc ggtgaaggtt    60
tcctgcaagg cttctggagg ccccttcagc atgactgctt tcacctggct gcgacaggcc   120
cctggacaag gcttgagtg gatgggtggg atcagcccta tctttcgtac accgaagtac   180
gcacagaagt tccagggcag agtcacgatt accgcggacg aatccacgaa cacagccaac   240
atggagctga ccagcctgaa atctgaggac acggccgtgt attactgtgc gagaaccctt   300
tcctcctacc aaccgaataa tgatgctttt gctatctggg gccaagggac aatggtcacc   360
gtctcttca                                                          369

<210> SEQ ID NO 41

<400> SEQUENCE: 41

000

<210> SEQ ID NO 42
<211> LENGTH: 330
<212> TYPE: DNA
<213> ORGANISM: Homo sapiens

<400> SEQUENCE: 42
ctgcctgtgc tgactcagcc accctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc agggtccct   180 gaccgattct ctggctccag gtcaggcacc tcagcctccc tggccatcat ggactccgg   240 cctgaggatg aagctgatta ttactgtcag tcgtatgaca gcaggctcag tgcttctctc   300
ttcggaactg ggaccacggt caccgtcctc                                   330

<210> SEQ ID NO 43
<211> LENGTH: 5
<212> TYPE: PRT
<213> ORGANISM: Artificial Sequence
<220> FEATURE:
<223> OTHER INFORMATION: Consensus Sequence

<400> SEQUENCE: 43

Ser Tyr Ala Phe Ser
1               5

<210> SEQ ID NO 44
<211> LENGTH: 5
<212> TYPE: PRT
<213> ORGANISM: Homo sapiens

<400> SEQUENCE: 44

Thr Asn Ala Phe Ser
1               5

<210> SEQ ID NO 45
<211> LENGTH: 5
<212> TYPE: PRT
<213> ORGANISM: Homo sapiens

<400> SEQUENCE: 45

Ala Tyr Ala Phe Thr
1               5

<210> SEQ ID NO 46
<211> LENGTH: 5
<212> TYPE: PRT
<213> ORGANISM: Homo sapiens

<400> SEQUENCE: 46

Ser Phe Ala Ile Ser
1               5

<210> SEQ ID NO 47
<211> LENGTH: 5
<212> TYPE: PRT
<213> ORGANISM: Homo sapiens

<400> SEQUENCE: 47

Ser Tyr Ala Ile Ser
1               5

<210> SEQ ID NO 48
<211> LENGTH: 5
<212> TYPE: PRT
<213> ORGANISM: Homo sapiens

<400> SEQUENCE: 48

Gly Tyr Tyr Ile His
1               5

<210> SEQ ID NO 49
<211> LENGTH: 5
<212> TYPE: PRT
<213> ORGANISM: Homo sapiens

<400> SEQUENCE: 49

Met Thr Ala Phe Thr
1               5

<210> SEQ ID NO 50
<211> LENGTH: 5
<212> TYPE: PRT
<213> ORGANISM: Homo sapiens

<400> SEQUENCE: 50

Asp Asn Ala Ile Ser
1               5

<210> SEQ ID NO 51
<211> LENGTH: 17
<212> TYPE: PRT
<213> ORGANISM: Artificial Sequence
<220> FEATURE:
<223> OTHER INFORMATION: Consensus Sequence

<400> SEQUENCE: 51

Gly Ile Ile Pro Met Phe Gly Thr Pro Asn Tyr Ala Gln Lys Phe Gln
1               5                   10                  15

Gly

<210> SEQ ID NO 52
<211> LENGTH: 17
<212> TYPE: PRT
<213> ORGANISM: Homo sapiens

<400> SEQUENCE: 52

Gly Val Ile Pro Leu Phe Arg Thr Ala Ser Tyr Ala Gln Asn Val Gln
1               5                   10                  15

Gly

<210> SEQ ID NO 53
<211> LENGTH: 17
<212> TYPE: PRT
<213> ORGANISM: Homo sapiens

<400> SEQUENCE: 53

Gly Ile Ile Gly Met Phe Gly Thr Ala Asn Tyr Ala Gln Lys Phe Gln
1               5                   10                  15

Gly

<210> SEQ ID NO 54
<211> LENGTH: 17
<212> TYPE: PRT
<213> ORGANISM: Homo sapiens

<400> SEQUENCE: 54

Gly Ile Ser Pro Met Phe Gly Thr Pro Asn Tyr Ala Gln Lys Phe Gln
1               5                   10                  15

Gly

<210> SEQ ID NO 55
<211> LENGTH: 17
<212> TYPE: PRT
<213> ORGANISM: Homo sapiens

<400> SEQUENCE: 55

Gly Ile Ile Gly Val Phe Gly Val Pro Lys Tyr Ala Gln Lys Phe Gln
1               5                   10                  15

Gly

<210> SEQ ID NO 56
<211> LENGTH: 17
<212> TYPE: PRT
<213> ORGANISM: Homo sapiens

<400> SEQUENCE: 56

```
Trp Ile Asn Pro Met Thr Gly Gly Thr Asn Tyr Ala Gln Lys Phe Gln
1               5                   10                  15
Val

<210> SEQ ID NO 57
<211> LENGTH: 17
<212> TYPE: PRT
<213> ORGANISM: Homo sapiens

<400> SEQUENCE: 57

Gly Ile Ser Pro Ile Phe Arg Thr Pro Lys Tyr Ala Gln Lys Phe Gln
1               5                   10                  15
Gly

<210> SEQ ID NO 58
<211> LENGTH: 17
<212> TYPE: PRT
<213> ORGANISM: Homo sapiens

<400> SEQUENCE: 58

Gly Ile Ile Pro Ile Phe Gly Lys Pro Asn Tyr Ala Gln Lys Phe Gln
1               5                   10                  15
Gly

<210> SEQ ID NO 59
<211> LENGTH: 12
<212> TYPE: PRT
<213> ORGANISM: Artificial Sequence
<220> FEATURE:
<223> OTHER INFORMATION: Consensus Sequence

<400> SEQUENCE: 59

Ser Ser Gly Tyr Tyr Tyr Gly Gly Gly Phe Asp Val
1               5                   10

<210> SEQ ID NO 60
<211> LENGTH: 13
<212> TYPE: PRT
<213> ORGANISM: Homo sapiens

<400> SEQUENCE: 60

Ser Ser Gly Tyr His Phe Gly Arg Ser His Phe Asp Ser
1               5                   10

<210> SEQ ID NO 61
<211> LENGTH: 11
<212> TYPE: PRT
<213> ORGANISM: Homo sapiens

<400> SEQUENCE: 61

Gly Leu Tyr Tyr Tyr Glu Ser Ser Leu Asp Tyr
1               5                   10

<210> SEQ ID NO 62
<211> LENGTH: 15
<212> TYPE: PRT
<213> ORGANISM: Homo sapiens

<400> SEQUENCE: 62

Ser Pro Ser Tyr Ile Cys Ser Gly Gly Thr Cys Val Phe Asp His
1               5                   10                  15

<210> SEQ ID NO 63
```

```
<211> LENGTH: 13
<212> TYPE: PRT
<213> ORGANISM: Homo sapiens

<400> SEQUENCE: 63

Glu Pro Gly Tyr Tyr Val Gly Lys Asn Gly Phe Asp Val
1               5                   10

<210> SEQ ID NO 64
<211> LENGTH: 17
<212> TYPE: PRT
<213> ORGANISM: Homo sapiens

<400> SEQUENCE: 64

Gly Ala Ser Val Leu Arg Tyr Phe Asp Trp Gln Pro Glu Ala Leu Asp
1               5                   10                  15

Ile

<210> SEQ ID NO 65
<211> LENGTH: 14
<212> TYPE: PRT
<213> ORGANISM: Homo sapiens

<400> SEQUENCE: 65

Thr Leu Ser Ser Tyr Gln Pro Asn Asn Asp Ala Phe Ala Ile
1               5                   10

<210> SEQ ID NO 66
<211> LENGTH: 14
<212> TYPE: PRT
<213> ORGANISM: Homo sapiens

<400> SEQUENCE: 66

Asp Ser Asp Ala Tyr Tyr Tyr Gly Ser Gly Gly Met Asp Val
1               5                   10

<210> SEQ ID NO 67
<211> LENGTH: 12
<212> TYPE: PRT
<213> ORGANISM: Homo sapiens

<400> SEQUENCE: 67

Thr Gly Ser Ser Ser Asn Ile Gly Asn Tyr Val Ala
1               5                   10

<210> SEQ ID NO 68
<211> LENGTH: 13
<212> TYPE: PRT
<213> ORGANISM: Homo sapiens

<400> SEQUENCE: 68

Thr Gly Ser Ser Ser Asn Ile Ala Ala Asn Tyr Val Gln
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Consensus Sequence

<400> SEQUENCE: 69

Thr Gly Thr Ser Ser Asp Val Gly Gly Tyr Asn Ser Val Ser
1               5                   10
```

```
<210> SEQ ID NO 70
<211> LENGTH: 13
<212> TYPE: PRT
<213> ORGANISM: Homo sapiens

<400> SEQUENCE: 70

Thr Gly Asn Ser Asn Asn Val Gly Asn Gln Gly Ala Ala
1               5                   10

<210> SEQ ID NO 71
<211> LENGTH: 13
<212> TYPE: PRT
<213> ORGANISM: Homo sapiens

<400> SEQUENCE: 71

Thr Gly Asp Ser Asn Asn Val Gly His Gln Gly Thr Ala
1               5                   10

<210> SEQ ID NO 72
<211> LENGTH: 11
<212> TYPE: PRT
<213> ORGANISM: Homo sapiens

<400> SEQUENCE: 72

Gly Gly Asn Asn Ile Gly Gly Tyr Ser Val His
1               5                   10

<210> SEQ ID NO 73
<211> LENGTH: 11
<212> TYPE: PRT
<213> ORGANISM: Homo sapiens

<400> SEQUENCE: 73

Arg Ala Ser Gln Ser Val Ser Ser Tyr Leu Ala
1               5                   10

<210> SEQ ID NO 74
<211> LENGTH: 12
<212> TYPE: PRT
<213> ORGANISM: Homo sapiens

<400> SEQUENCE: 74

Arg Ala Ser Gln Ser Leu Ser Ser Lys Tyr Leu Ala
1               5                   10

<210> SEQ ID NO 75
<211> LENGTH: 12
<212> TYPE: PRT
<213> ORGANISM: Homo sapiens

<400> SEQUENCE: 75

Thr Gly Ser Ser Ser Asn Ile Gly Asn Tyr Val Ala
1               5                   10

<210> SEQ ID NO 76
<211> LENGTH: 13
<212> TYPE: PRT
<213> ORGANISM: Homo sapiens

<400> SEQUENCE: 76

Ser Gly Ser Ser Ser Asn Ile Gly Ser Asn Thr Val Asn
1               5                   10

<210> SEQ ID NO 77
```

```
<211> LENGTH: 11
<212> TYPE: PRT
<213> ORGANISM: Homo sapiens

<400> SEQUENCE: 77

Arg Ala Ser Gln Ser Ile Ser Ser Tyr Leu Asn
1               5                   10

<210> SEQ ID NO 78
<211> LENGTH: 12
<212> TYPE: PRT
<213> ORGANISM: Homo sapiens

<400> SEQUENCE: 78

Thr Leu Ser Ser Gly His Ser Asn Tyr Ile Ile Ala
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Consensus Sequence

<400> SEQUENCE: 79

Ser Asn Ser Asp Arg Pro Ser
1               5

<210> SEQ ID NO 80
<211> LENGTH: 7
<212> TYPE: PRT
<213> ORGANISM: Homo sapiens

<400> SEQUENCE: 80

Glu Asp Asp Arg Arg Pro Ser
1               5

<210> SEQ ID NO 81
<211> LENGTH: 7
<212> TYPE: PRT
<213> ORGANISM: Homo sapiens

<400> SEQUENCE: 81

Glu Val Thr Lys Arg Pro Ser
1               5

<210> SEQ ID NO 82
<211> LENGTH: 7
<212> TYPE: PRT
<213> ORGANISM: Homo sapiens

<400> SEQUENCE: 82

Arg Asn Asn Asp Arg Pro Ser
1               5

<210> SEQ ID NO 83
<211> LENGTH: 7
<212> TYPE: PRT
<213> ORGANISM: Homo sapiens

<400> SEQUENCE: 83

Arg Asn Gly Asn Arg Pro Ser
1               5

<210> SEQ ID NO 84
```

```
<211> LENGTH: 7
<212> TYPE: PRT
<213> ORGANISM: Homo sapiens

<400> SEQUENCE: 84

Asp Asp Lys Asp Arg Pro Ser
1               5

<210> SEQ ID NO 85
<211> LENGTH: 7
<212> TYPE: PRT
<213> ORGANISM: Homo sapiens

<400> SEQUENCE: 85

Asp Ala Ser Asn Arg Ala Thr
1               5

<210> SEQ ID NO 86
<211> LENGTH: 7
<212> TYPE: PRT
<213> ORGANISM: Homo sapiens

<400> SEQUENCE: 86

Gly Ala Ser Ser Arg Ala Thr
1               5

<210> SEQ ID NO 87
<211> LENGTH: 7
<212> TYPE: PRT
<213> ORGANISM: Homo sapiens

<400> SEQUENCE: 87

Ser Asn Asn Gln Arg Pro Ser
1               5

<210> SEQ ID NO 88
<211> LENGTH: 7
<212> TYPE: PRT
<213> ORGANISM: Homo sapiens

<400> SEQUENCE: 88

Ala Ala Ser Ser Leu Gln Arg
1               5

<210> SEQ ID NO 89
<211> LENGTH: 7
<212> TYPE: PRT
<213> ORGANISM: Homo sapiens

<400> SEQUENCE: 89

Ser Asn Glu Gln Arg Pro Ser
1               5

<210> SEQ ID NO 90
<211> LENGTH: 11
<212> TYPE: PRT
<213> ORGANISM: Homo sapiens

<400> SEQUENCE: 90

Val Asn Ser Asp Gly Ser His Thr Lys Gly Asp
1               5                   10

<210> SEQ ID NO 91
<211> LENGTH: 10
<212> TYPE: PRT
```

<213> ORGANISM: Artificial Sequence
<220> FEATURE:
<223> OTHER INFORMATION: Consensus Sequence

<400> SEQUENCE: 91

Gln Ser Tyr Asp Ser Leu Ser Ala Tyr Val
1               5                   10

<210> SEQ ID NO 92
<211> LENGTH: 10
<212> TYPE: PRT
<213> ORGANISM: Homo sapiens

<400> SEQUENCE: 92

Gln Ser Tyr Asp Thr Asn Asn His Ala Val
1               5                   10

<210> SEQ ID NO 93
<211> LENGTH: 10
<212> TYPE: PRT
<213> ORGANISM: Homo sapiens

<400> SEQUENCE: 93

Cys Ser Tyr Ala Gly His Ser Ala Tyr Val
1               5                   10

<210> SEQ ID NO 94
<211> LENGTH: 11
<212> TYPE: PRT
<213> ORGANISM: Homo sapiens

<400> SEQUENCE: 94

Ser Thr Trp Asp Ser Ser Leu Ser Ala Val Val
1               5                   10

<210> SEQ ID NO 95
<211> LENGTH: 11
<212> TYPE: PRT
<213> ORGANISM: Homo sapiens

<400> SEQUENCE: 95

Ser Val Trp Asp Ser Ser Leu Ser Ala Trp Val
1               5                   10

<210> SEQ ID NO 96
<211> LENGTH: 11
<212> TYPE: PRT
<213> ORGANISM: Homo sapiens

<400> SEQUENCE: 96

Gln Val Trp Asp Ser Gly Asn Asp Arg Pro Leu
1               5                   10

<210> SEQ ID NO 97
<211> LENGTH: 9
<212> TYPE: PRT
<213> ORGANISM: Homo sapiens

<400> SEQUENCE: 97

Gln Gln Tyr Gly Ser Ser Pro Gln Val
1               5

<210> SEQ ID NO 98
<211> LENGTH: 9
<212> TYPE: PRT

```
<213> ORGANISM: Homo sapiens

<400> SEQUENCE: 98

Gln Gln Tyr Asp Gly Val Pro Arg Thr
1               5

<210> SEQ ID NO 99
<211> LENGTH: 11
<212> TYPE: PRT
<213> ORGANISM: Homo sapiens

<400> SEQUENCE: 99

Gln Ser Tyr Asp Ser Arg Leu Ser Ala Ser Leu
1               5                   10

<210> SEQ ID NO 100
<211> LENGTH: 9
<212> TYPE: PRT
<213> ORGANISM: Homo sapiens

<400> SEQUENCE: 100

Gln Gln Tyr Asp Ser Ser Pro Tyr Thr
1               5

<210> SEQ ID NO 101
<211> LENGTH: 11
<212> TYPE: PRT
<213> ORGANISM: Homo sapiens

<400> SEQUENCE: 101

Ala Ser Trp Asp Asp Asn Leu Ser Gly Trp Val
1               5                   10

<210> SEQ ID NO 102
<211> LENGTH: 9
<212> TYPE: PRT
<213> ORGANISM: Homo sapiens

<400> SEQUENCE: 102

Glu Thr Trp Asp Thr Lys Ile His Val
1               5

<210> SEQ ID NO 103
<211> LENGTH: 10
<212> TYPE: PRT
<213> ORGANISM: Artificial Sequence
<220> FEATURE:
<223> OTHER INFORMATION: Synthetic peptide

<400> SEQUENCE: 103

Gly Thr Glu Thr Ser Gln Val Ala Pro Ala
1               5                   10

<210> SEQ ID NO 104
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 104

His His His His His His
1               5

<210> SEQ ID NO 105
```

```
<211> LENGTH: 4
<212> TYPE: PRT
<213> ORGANISM: Influenza A virus

<400> SEQUENCE: 105

Ile Asn Gly Trp
1

<210> SEQ ID NO 106
<211> LENGTH: 4
<212> TYPE: PRT
<213> ORGANISM: Influenza A virus

<400> SEQUENCE: 106

Ile Asp Gly Trp
1

<210> SEQ ID NO 107
<211> LENGTH: 4
<212> TYPE: PRT
<213> ORGANISM: Influenza A virus

<400> SEQUENCE: 107

Val Ala Gly Trp
1

<210> SEQ ID NO 108
<211> LENGTH: 4
<212> TYPE: PRT
<213> ORGANISM: Influenza A virus

<400> SEQUENCE: 108

Val Asp Gly Trp
1

<210> SEQ ID NO 109
<211> LENGTH: 4
<212> TYPE: PRT
<213> ORGANISM: Influenza A virus

<400> SEQUENCE: 109

Ile Ala Gly Trp
1

<210> SEQ ID NO 110
<211> LENGTH: 87
<212> TYPE: PRT
<213> ORGANISM: Homo sapiens

<400> SEQUENCE: 110

Lys Lys Pro Gly Ser Ser Val Lys Val Ser Cys Lys Ala Ser Gly Gly
1               5                   10                  15

Thr Phe Ser Ser Tyr Ala Ile Ser Trp Val Arg Gln Ala Pro Gly Gln
            20                  25                  30

Gly Leu Glu Trp Met Gly Gly Ile Ile Pro Met Phe Gly Thr Pro Asn
        35                  40                  45

Tyr Ala Gln Lys Phe Gln Gly Arg Val Thr Ile Thr Ala Asp Glu Ser
    50                  55                  60

Thr Ser Thr Ala Tyr Met Glu Leu Ser Ser Leu Arg Ser Glu Asp Thr
65                  70                  75                  80

Ala Val Tyr Tyr Cys Ala Arg
                85
```

<210> SEQ ID NO 111
<211> LENGTH: 87
<212> TYPE: PRT
<213> ORGANISM: Homo sapiens

<400> SEQUENCE: 111

Lys Lys Pro Gly Ser Ser Val Lys Val Ser Cys Lys Ala Ser Gly Gly
1               5                   10                  15

Thr Phe Ser Ser Tyr Ala Ile Ser Trp Val Arg Gln Ala Pro Gly Gln
            20                  25                  30

Gly Leu Glu Trp Met Gly Gly Ile Ile Pro Ile Phe Gly Thr Pro Asn
        35                  40                  45

Tyr Ala Gln Lys Phe Gln Gly Arg Val Thr Ile Thr Ala Asp Glu Ser
    50                  55                  60

Thr Ser Thr Ala Tyr Met Glu Leu Ser Ser Leu Arg Ser Glu Asp Thr
65                  70                  75                  80

Ala Val Tyr Tyr Cys Ala Arg
            85

<210> SEQ ID NO 112
<211> LENGTH: 108
<212> TYPE: PRT
<213> ORGANISM: Homo sapiens

<400> SEQUENCE: 112

Lys Lys Pro Gly Ser Ser Val Lys Val Ser Cys Thr Ser Ser Glu Val
1               5                   10                  15

Thr Phe Ser Ser Phe Ala Ile Ser Trp Val Arg Gln Ala Pro Gly Gln
            20                  25                  30

Gly Leu Glu Trp Leu Gly Gly Ile Ser Pro Met Phe Gly Thr Pro Asn
        35                  40                  45

Tyr Ala Gln Lys Phe Gln Gly Arg Val Thr Ile Thr Ala Asp Gln Ser
    50                  55                  60

Thr Arg Thr Ala Tyr Met Asp Leu Arg Ser Leu Arg Ser Glu Asp Thr
65                  70                  75                  80

Ala Val Tyr Tyr Cys Ala Arg Ser Pro Ser Tyr Ile Cys Ser Gly Gly
            85                  90                  95

Thr Cys Val Phe Asp His Trp Gly Gln Gly Thr Leu
        100                 105

<210> SEQ ID NO 113
<211> LENGTH: 104
<212> TYPE: PRT
<213> ORGANISM: Homo sapiens

<400> SEQUENCE: 113

Lys Lys Pro Gly Ser Ser Val Lys Val Ser Cys Lys Ala Ser Gly Gly
1               5                   10                  15

Thr Phe Ser Ala Tyr Ala Phe Thr Trp Val Arg Gln Ala Pro Gly Gln
            20                  25                  30

Gly Leu Glu Trp Met Gly Gly Ile Ile Gly Met Phe Gly Thr Ala Asn
        35                  40                  45

Tyr Ala Gln Lys Phe Gln Gly Arg Val Thr Ile Thr Ala Asp Glu Leu
    50                  55                  60

Thr Ser Thr Ala Tyr Met Glu Leu Ser Ser Leu Thr Ser Glu Asp Thr
65                  70                  75                  80

Ala Leu Tyr Tyr Cys Ala Arg Gly Leu Tyr Tyr Tyr Glu Ser Ser Phe 85                  90                  95

Asp Tyr Trp Gly Gln Gly Thr Leu
            100

<210> SEQ ID NO 114
<211> LENGTH: 107
<212> TYPE: PRT
<213> ORGANISM: Homo sapiens

<400> SEQUENCE: 114

Lys Lys Pro Gly Ser Ser Val Lys Val Ser Cys Lys Ala Ser Gly Gly
1               5                   10                  15

Pro Phe Ser Met Thr Ala Phe Thr Trp Leu Arg Gln Ala Pro Gly Gln
            20                  25                  30

Gly Leu Glu Trp Met Gly Gly Ile Ser Pro Ile Phe Arg Thr Pro Lys
        35                  40                  45

Tyr Ala Gln Lys Phe Gln Gly Arg Val Thr Ile Thr Ala Asp Glu Ser
    50                  55                  60

Thr Asn Thr Ala Asn Met Glu Leu Thr Ser Leu Lys Ser Glu Asp Thr
65                  70                  75                  80

Ala Val Tyr Tyr Cys Ala Arg Thr Leu Ser Ser Tyr Gln Pro Asn Asn
                85                  90                  95

Asp Ala Phe Ala Ile Trp Gly Gln Gly Thr Met
            100                 105

<210> SEQ ID NO 115
<211> LENGTH: 106
<212> TYPE: PRT
<213> ORGANISM: Homo sapiens

<400> SEQUENCE: 115

Lys Lys Pro Gly Ala Ser Val Lys Val Ser Cys Lys Thr Ser Gly Val
1               5                   10                  15

Thr Phe Ser Ser Tyr Ala Ile Ser Trp Val Arg Gln Ala Pro Gly Gln
            20                  25                  30

Gly Leu Glu Trp Met Gly Gly Ile Ile Gly Val Phe Gly Val Pro Lys
        35                  40                  45

Tyr Ala Gln Lys Phe Gln Gly Arg Val Thr Ile Thr Ala Asp Lys Pro
    50                  55                  60

Thr Ser Thr Val Tyr Met Glu Leu Asn Ser Leu Arg Ala Glu Asp Thr
65                  70                  75                  80

Ala Val Tyr Tyr Cys Ala Arg Glu Pro Gly Tyr Tyr Val Gly Lys Asn
                85                  90                  95

Gly Phe Asp Val Trp Gly Gln Gly Thr Met
            100                 105

<210> SEQ ID NO 116
<211> LENGTH: 105
<212> TYPE: PRT
<213> ORGANISM: Homo sapiens

<400> SEQUENCE: 116

Lys Lys Pro Gly Ser Ser Val Lys Val Ser Cys Lys Ala Pro Gly Gly
1               5                   10                  15

Ile Phe Asn Thr Asn Ala Phe Ser Trp Val Arg Gln Ala Pro Gly Gln
            20                  25                  30

Gly Leu Glu Trp Val Gly Gly Val Ile Pro Leu Phe Arg Thr Ala Ser
        35                  40                  45

-continued

```
Tyr Ala Gln Asn Val Gln Gly Arg Val Thr Ile Thr Ala Asp Glu Ser
             50                  55                  60

Thr Asn Thr Ala Tyr Met Glu Leu Thr Ser Leu Arg Ser Ala Asp Thr
 65                  70                  75                  80

Ala Val Tyr Tyr Cys Ala Arg Ser Ser Gly Tyr His Phe Arg Ser His
                 85                  90                  95

Phe Asp Ser Trp Gly Leu Gly Thr Leu
            100                 105

<210> SEQ ID NO 117
<211> LENGTH: 110
<212> TYPE: PRT
<213> ORGANISM: Homo sapiens

<400> SEQUENCE: 117

Arg Lys Pro Gly Ala Ser Val Lys Val Ser Cys Lys Ala Ser Gly Tyr
 1               5                  10                  15

Thr Phe Thr Gly Tyr Tyr Ile His Trp Val Arg Gln Ala Pro Gly Gln
             20                  25                  30

Gly Leu Glu Trp Met Gly Trp Ile Asn Pro Met Thr Gly Gly Thr Asn
         35                  40                  45

Tyr Ala Gln Lys Phe Gln Val Trp Val Thr Met Thr Arg Asp Thr Ser
     50                  55                  60

Ile Asn Thr Ala Tyr Met Glu Val Thr Arg Leu Thr Ser Asp Asp Thr
 65                  70                  75                  80

Ala Val Tyr Tyr Cys Ala Arg Gly Ala Ser Val Leu Arg Tyr Phe Asp
                 85                  90                  95

Trp Gln Pro Glu Ala Leu Asp Ile Trp Gly Leu Gly Thr Thr
            100                 105                 110

<210> SEQ ID NO 118
<211> LENGTH: 8
<212> TYPE: PRT
<213> ORGANISM: Homo sapiens

<400> SEQUENCE: 118

Gly Gly Thr Phe Ser Ser Tyr Ala
 1               5

<210> SEQ ID NO 119
<211> LENGTH: 8
<212> TYPE: PRT
<213> ORGANISM: Homo sapiens

<400> SEQUENCE: 119

Gly Gly Thr Phe Ser Ser Tyr Ala
 1               5

<210> SEQ ID NO 120
<211> LENGTH: 8
<212> TYPE: PRT
<213> ORGANISM: Homo sapiens

<400> SEQUENCE: 120

Glu Val Thr Phe Ser Ser Phe Ala
 1               5

<210> SEQ ID NO 121
<211> LENGTH: 8
<212> TYPE: PRT
```

<213> ORGANISM: Homo sapiens

<400> SEQUENCE: 121

Gly Gly Thr Phe Ser Ala Tyr Ala
1               5

<210> SEQ ID NO 122
<211> LENGTH: 8
<212> TYPE: PRT
<213> ORGANISM: Homo sapiens

<400> SEQUENCE: 122

Gly Gly Pro Phe Ser Met Thr Ala
1               5

<210> SEQ ID NO 123
<211> LENGTH: 8
<212> TYPE: PRT
<213> ORGANISM: Homo sapiens

<400> SEQUENCE: 123

Gly Val Thr Phe Ser Ser Tyr Ala
1               5

<210> SEQ ID NO 124
<211> LENGTH: 8
<212> TYPE: PRT
<213> ORGANISM: Homo sapiens

<400> SEQUENCE: 124

Gly Gly Ile Phe Asn Thr Asn Ala
1               5

<210> SEQ ID NO 125
<211> LENGTH: 8
<212> TYPE: PRT
<213> ORGANISM: Homo sapiens

<400> SEQUENCE: 125

Gly Tyr Thr Phe Thr Gly Tyr Tyr
1               5

<210> SEQ ID NO 126
<211> LENGTH: 8
<212> TYPE: PRT
<213> ORGANISM: Homo sapiens

<400> SEQUENCE: 126

Ile Ile Pro Met Phe Gly Thr Pro
1               5

<210> SEQ ID NO 127
<211> LENGTH: 8
<212> TYPE: PRT
<213> ORGANISM: Homo sapiens

<400> SEQUENCE: 127

Ile Ile Pro Ile Phe Gly Thr Pro
1               5

<210> SEQ ID NO 128
<211> LENGTH: 8
<212> TYPE: PRT
<213> ORGANISM: Homo sapiens

```
<400> SEQUENCE: 128

Ile Ser Pro Met Phe Gly Thr Pro
1               5

<210> SEQ ID NO 129
<211> LENGTH: 8
<212> TYPE: PRT
<213> ORGANISM: Homo sapiens

<400> SEQUENCE: 129

Ile Ile Gly Met Phe Gly Thr Ala
1               5

<210> SEQ ID NO 130
<211> LENGTH: 8
<212> TYPE: PRT
<213> ORGANISM: Homo sapiens

<400> SEQUENCE: 130

Ile Ser Pro Ile Phe Arg Thr Pro
1               5

<210> SEQ ID NO 131
<211> LENGTH: 8
<212> TYPE: PRT
<213> ORGANISM: Homo sapiens

<400> SEQUENCE: 131

Ile Ile Gly Val Phe Gly Val Pro
1               5

<210> SEQ ID NO 132
<211> LENGTH: 8
<212> TYPE: PRT
<213> ORGANISM: Homo sapiens

<400> SEQUENCE: 132

Val Ile Pro Leu Phe Arg Thr Ala
1               5

<210> SEQ ID NO 133
<211> LENGTH: 8
<212> TYPE: PRT
<213> ORGANISM: Homo sapiens

<400> SEQUENCE: 133

Ile Asn Pro Met Thr Gly Gly Thr
1               5

<210> SEQ ID NO 134
<211> LENGTH: 17
<212> TYPE: PRT
<213> ORGANISM: Homo sapiens

<400> SEQUENCE: 134

Ala Arg Ser Pro Ser Tyr Ile Cys Ser Gly Gly Thr Cys Val Phe Asp
1               5                   10                  15

His

<210> SEQ ID NO 135
<211> LENGTH: 13
<212> TYPE: PRT
<213> ORGANISM: Homo sapiens
```

```
<400> SEQUENCE: 135

Ala Arg Gly Leu Tyr Tyr Tyr Glu Ser Ser Phe Asp Tyr
1               5                   10

<210> SEQ ID NO 136
<211> LENGTH: 16
<212> TYPE: PRT
<213> ORGANISM: Homo sapiens

<400> SEQUENCE: 136

Ala Arg Thr Leu Ser Ser Tyr Gln Pro Asn Asn Asp Ala Phe Ala Ile
1               5                   10                  15

<210> SEQ ID NO 137
<211> LENGTH: 15
<212> TYPE: PRT
<213> ORGANISM: Homo sapiens

<400> SEQUENCE: 137

Ala Arg Glu Pro Gly Tyr Tyr Val Gly Lys Asn Gly Phe Asp Val
1               5                   10                  15

<210> SEQ ID NO 138
<211> LENGTH: 14
<212> TYPE: PRT
<213> ORGANISM: Homo sapiens

<400> SEQUENCE: 138

Ala Arg Ser Ser Gly Tyr His Phe Arg Ser His Phe Asp Ser
1               5                   10

<210> SEQ ID NO 139
<211> LENGTH: 19
<212> TYPE: PRT
<213> ORGANISM: Homo sapiens

<400> SEQUENCE: 139

Ala Arg Gly Ala Ser Val Leu Arg Tyr Phe Asp Trp Gln Pro Glu Ala
1               5                   10                  15

Leu Asp Ile

<210> SEQ ID NO 140
<211> LENGTH: 8
<212> TYPE: PRT
<213> ORGANISM: Homo sapiens

<400> SEQUENCE: 140

Ser Gly Asn Ile Ala Ala Asn Tyr
1               5

<210> SEQ ID NO 141
<211> LENGTH: 9
<212> TYPE: PRT
<213> ORGANISM: Homo sapiens

<400> SEQUENCE: 141

Ser Ser Asp Val Gly Gly Tyr Asn Ser
1               5

<210> SEQ ID NO 142
<211> LENGTH: 8
<212> TYPE: PRT
<213> ORGANISM: Homo sapiens
```

```
<400> SEQUENCE: 142

Ser Asn Asn Val Gly Asn Gln Gly
1               5

<210> SEQ ID NO 143
<211> LENGTH: 8
<212> TYPE: PRT
<213> ORGANISM: Homo sapiens

<400> SEQUENCE: 143

Ser Asn Asn Val Gly His Gln Gly
1               5

<210> SEQ ID NO 144
<211> LENGTH: 6
<212> TYPE: PRT
<213> ORGANISM: Homo sapiens

<400> SEQUENCE: 144

Asn Ile Gly Gly Tyr Ser
1               5

<210> SEQ ID NO 145
<211> LENGTH: 7
<212> TYPE: PRT
<213> ORGANISM: Homo sapiens

<400> SEQUENCE: 145

Gln Ser Ser Val Ser Ser Tyr
1               5

<210> SEQ ID NO 146
<211> LENGTH: 7
<212> TYPE: PRT
<213> ORGANISM: Homo sapiens

<400> SEQUENCE: 146

Gln Ser Leu Ser Ser Lys Tyr
1               5

<210> SEQ ID NO 147
<211> LENGTH: 8
<212> TYPE: PRT
<213> ORGANISM: Homo sapiens

<400> SEQUENCE: 147

Ser Ser Asn Ile Gly Ser Asn Thr
1               5

<210> SEQ ID NO 148
<211> LENGTH: 6
<212> TYPE: PRT
<213> ORGANISM: Homo sapiens

<400> SEQUENCE: 148

Gln Ser Ile Ser Ser Tyr
1               5

<210> SEQ ID NO 149
<211> LENGTH: 8
<212> TYPE: PRT
<213> ORGANISM: Homo sapiens

<400> SEQUENCE: 149
```

```
Thr Ser Asn Ile Gly Arg Asn His
1               5

<210> SEQ ID NO 150
<211> LENGTH: 3
<212> TYPE: PRT
<213> ORGANISM: Homo sapiens

<400> SEQUENCE: 150

Glu Asp Asp
1

<210> SEQ ID NO 151
<211> LENGTH: 3
<212> TYPE: PRT
<213> ORGANISM: Homo sapiens

<400> SEQUENCE: 151

Glu Val Thr
1

<210> SEQ ID NO 152
<211> LENGTH: 3
<212> TYPE: PRT
<213> ORGANISM: Homo sapiens

<400> SEQUENCE: 152

Arg Asn Asn
1

<210> SEQ ID NO 153
<211> LENGTH: 3
<212> TYPE: PRT
<213> ORGANISM: Homo sapiens

<400> SEQUENCE: 153

Arg Asn Gly
1

<210> SEQ ID NO 154
<211> LENGTH: 3
<212> TYPE: PRT
<213> ORGANISM: Homo sapiens

<400> SEQUENCE: 154

Asp Asp Lys
1

<210> SEQ ID NO 155
<211> LENGTH: 3
<212> TYPE: PRT
<213> ORGANISM: Homo sapiens

<400> SEQUENCE: 155

Asp Ala Ser
1

<210> SEQ ID NO 156
<211> LENGTH: 3
<212> TYPE: PRT
<213> ORGANISM: Homo sapiens

<400> SEQUENCE: 156

Gly Ala Ser
1
```

<210> SEQ ID NO 157
<211> LENGTH: 3
<212> TYPE: PRT
<213> ORGANISM: Homo sapiens

<400> SEQUENCE: 157

Ser Asn Asn
1

<210> SEQ ID NO 158
<211> LENGTH: 3
<212> TYPE: PRT
<213> ORGANISM: Homo sapiens

<400> SEQUENCE: 158

Ala Ala Ser
1

<210> SEQ ID NO 159
<211> LENGTH: 3
<212> TYPE: PRT
<213> ORGANISM: Homo sapiens

<400> SEQUENCE: 159

Ser Asn Glu
1

<210> SEQ ID NO 160
<211> LENGTH: 10
<212> TYPE: PRT
<213> ORGANISM: Homo sapiens

<400> SEQUENCE: 160

Gln Thr Tyr Asp Thr Asn Asn His Ala Val
1               5                   10

<210> SEQ ID NO 161
<211> LENGTH: 10
<212> TYPE: PRT
<213> ORGANISM: Homo sapiens

<400> SEQUENCE: 161

Cys Ser Tyr Ala Gly His Ser Ala Tyr Val
1               5                   10

<210> SEQ ID NO 162
<211> LENGTH: 11
<212> TYPE: PRT
<213> ORGANISM: Homo sapiens

<400> SEQUENCE: 162

Ser Thr Trp Asp Ser Ser Leu Ser Ala Val Val
1               5                   10

<210> SEQ ID NO 163
<211> LENGTH: 11
<212> TYPE: PRT
<213> ORGANISM: Homo sapiens

<400> SEQUENCE: 163

Ser Val Trp Asp Ser Ser Leu Ser Ala Trp Val
1               5                   10

-continued

```
<210> SEQ ID NO 164
<211> LENGTH: 11
<212> TYPE: PRT
<213> ORGANISM: Homo sapiens

<400> SEQUENCE: 164

Gln Val Trp Asp Ser Gly Asn Asp Arg Pro Leu
1               5                   10

<210> SEQ ID NO 165
<211> LENGTH: 8
<212> TYPE: PRT
<213> ORGANISM: Homo sapiens

<400> SEQUENCE: 165

Gln Gln Tyr Gly Ser Ser Pro Gln
1               5

<210> SEQ ID NO 166
<211> LENGTH: 9
<212> TYPE: PRT
<213> ORGANISM: Homo sapiens

<400> SEQUENCE: 166

Gln Gln Tyr Asp Gly Val Pro Arg Thr
1               5

<210> SEQ ID NO 167
<211> LENGTH: 11
<212> TYPE: PRT
<213> ORGANISM: Homo sapiens

<400> SEQUENCE: 167

Gln Ser Tyr Asp Ser Arg Leu Ser Ala Ser Leu
1               5                   10

<210> SEQ ID NO 168
<211> LENGTH: 9
<212> TYPE: PRT
<213> ORGANISM: Homo sapiens

<400> SEQUENCE: 168

Gln Gln Tyr Asp Ser Ser Pro Tyr Thr
1               5

<210> SEQ ID NO 169
<211> LENGTH: 11
<212> TYPE: PRT
<213> ORGANISM: Homo sapiens

<400> SEQUENCE: 169

Ala Ser Trp Asp Asp Asn Leu Ser Gly Trp Val
1               5                   10

<210> SEQ ID NO 170
<211> LENGTH: 2
<212> TYPE: PRT
<213> ORGANISM: Homo sapiens

<400> SEQUENCE: 170

Ala Arg
1

<210> SEQ ID NO 171
<211> LENGTH: 10
```

-continued

```
<212> TYPE: PRT
<213> ORGANISM: Homo sapiens

<400> SEQUENCE: 171

Gln Val Gln Leu Val Gln Gly Ala Glu Val
1               5                   10

<210> SEQ ID NO 172
<211> LENGTH: 5
<212> TYPE: PRT
<213> ORGANISM: Homo sapiens

<400> SEQUENCE: 172

Val Thr Val Ser Ser
1               5
```

UNITED STATES PATENT AND TRADEMARK OFFICE
CERTIFICATE OF CORRECTION

PATENT NO. : 9,951,122 B2
APPLICATION NO. : 13/965092
DATED : April 24, 2018
INVENTOR(S) : Wayne A. Marasco, Jianhua Sui and Robert C. Liddington Page 1 of 1

It is certified that error appears in the above-identified patent and that said Letters Patent is hereby corrected as shown below:

In the Specification

At Column 1, Line numbers 19-22, change:
"This invention was made with United States Government support under National Institutes of Health Grants U01 AI074518-01. The United States Government has certain rights in the invention."

To:
--This invention was made with government support under grant number AI074518 awarded by The National Institutes of Health. The government has certain rights in the invention.--

Signed and Sealed this
Twenty-fourth Day of September, 2019

Andrei Iancu
*Director of the United States Patent and Trademark Office*